United States Patent
Zettl

(10) Patent No.: US 12,178,797 B2
(45) Date of Patent: *Dec. 31, 2024

(54) FORMULATION FOR PAIN MANAGEMENT

(71) Applicant: Zyus Life Sciences Inc., Saskatoon (CA)

(72) Inventor: Brenton Harold Zettl, Saskatoon (CA)

(*) Notice: Subject to any disclaimer, the term of this patent is extended or adjusted under 35 U.S.C. 154(b) by 816 days.

This patent is subject to a terminal disclaimer.

(21) Appl. No.: 17/218,329

(22) Filed: Mar. 31, 2021

(65) Prior Publication Data

US 2021/0236457 A1 Aug. 5, 2021

Related U.S. Application Data

(63) Continuation-in-part of application No. 17/162,903, filed on Jan. 29, 2021, now Pat. No. 11,963,943, which is a continuation-in-part of application No. PCT/CA2020/050588, filed on May 1, 2020.

(60) Provisional application No. 63/011,508, filed on Apr. 17, 2020, provisional application No. 62/842,696, filed on May 3, 2019.

(51) Int. Cl.
| | |
|---|---|
| A61K 31/352 | (2006.01) |
| A61K 31/05 | (2006.01) |
| A61P 25/02 | (2006.01) |
| A61P 29/00 | (2006.01) |

(52) U.S. Cl.
CPC ........... *A61K 31/352* (2013.01); *A61K 31/05* (2013.01); *A61P 25/02* (2018.01); *A61P 29/00* (2018.01)

(58) Field of Classification Search
CPC ....... A61K 31/352; A61K 31/05; A61P 25/02; A61P 29/00
USPC ........................................................ 514/454
See application file for complete search history.

(56) References Cited

U.S. PATENT DOCUMENTS

| | | |
|---|---|---|
| 2010/0239693 A1 | 9/2010 | Guy et al. |
| 2014/0107192 A1 | 4/2014 | Maione et al. |
| 2015/0126754 A1 | 5/2015 | Fernandez Cid et al. |
| 2016/0106705 A1 | 4/2016 | Verzura et al. |
| 2016/0360721 A1 | 12/2016 | De Meijer |
| 2017/0027978 A1 | 2/2017 | Mukunda et al. |
| 2017/0266153 A1 | 9/2017 | Levy et al. |
| 2018/0193304 A1 | 7/2018 | Cranford et al. |
| 2019/0117617 A1 | 4/2019 | Kariman |
| 2020/0246404 A1 | 8/2020 | Yucel et al. |
| 2021/0236458 A1 | 8/2021 | Zettl |
| 2023/0321121 A1 | 10/2023 | Zettl |

FOREIGN PATENT DOCUMENTS

| | | |
|---|---|---|
| CN | 107095302 A | 8/2017 |
| GB | 2381194 A | 4/2003 |
| IL | 264210 | 2/2019 |
| JP | 2014513715 A | 6/2014 |
| JP | 2018529736 A1 | 10/2018 |
| JP | 2019521189 A | 7/2019 |
| JP | 2019525921 A | 9/2019 |
| KR | 20050042157 A | 5/2005 |
| KR | 20130067248 A | 6/2013 |
| KR | 20140037124 A | 3/2014 |
| WO | 2006095124 A1 | 9/2006 |
| WO | 2007052013 A1 | 5/2007 |
| WO | 2007083098 A1 | 7/2007 |
| WO | 2008052013 A2 | 5/2008 |
| WO | 2012144892 A1 | 10/2012 |
| WO | 2012160358 A1 | 11/2012 |
| WO | 2013165251 A1 | 11/2013 |
| WO | 2016044370 A1 | 3/2016 |
| WO | 2017059088 A1 | 4/2017 |
| WO | 2018009717 A1 | 1/2018 |
| WO | 2018015411 A1 | 1/2018 |
| WO | 2019002926 A1 | 1/2019 |
| WO | 2020006599 A1 | 1/2020 |

OTHER PUBLICATIONS

Indian Patent Application No. 202117051745, Office Action dated Mar. 31, 2022.
Israel Patent Application No. 287772, Office Action dated Apr. 5, 2022.
Japanese Patent Application No. 2021-576431, Office Action dated Apr. 18, 2022—English Translation available.
Korean Patent Application No. 10-2021-7039671, Korean Office Action dated Mar. 18, 2022—English Translation Available.
Australian Patent Application No. AU2020268218, Office Action dated Dec. 22, 2021.
Japanese Patent Application No. 2021576431, Office Action dated Aug. 08, 2022—English Translation not available.
Korean Patent Application No. 10-2021-7039671, Office Action dated Aug. 12, 2022—English Translation Not Available.
Abid et al., "Exploring Patterns Enriched in a Dataset With Contrastive Principal Component Analysis," Nature Communications, May 2018, vol. 9, pp. 1-7.
Bates et al., "Fitting Linear Mixed-Effects Models Using lme4," Journal of Statistical Software, Oct. 2015, vol. 67(1), pp. 1-48. doi: 10.18637/jss.v067.i01.
Bouhassira et al., "Prevalence of Chronic Pain With Neuropathic Characteristics in the General Population," Pain, Jun. 2008, vol. 136(3), pp. 380-387.

(Continued)

*Primary Examiner* — Kristin A Vajda
(74) *Attorney, Agent, or Firm* — Borden Ladner Gervais LLP; Kathleen E. Marsman

(57) ABSTRACT

A method of pain management is described, for use by individuals experiencing pain, comprising administration of a formulation comprising a plurality of cannabinoids. Primary cannabinoids are present in the formulation in amounts according to a weight ratio of THC:CBC:CBD ranging from 5:5:5 to 5:1:5. Methods of using the formulation, doses and dosage forms are described, including a formulation pairing in which a first formulation comprising CBC:CBD at 1:5 to 5:5 is utilized at certain times of day when psychoactive effects of THC are not desired, and a second formulation comprising THC:CBC:CBD is used at other times of day, typically evening or bedtime.

6 Claims, 37 Drawing Sheets

(56) References Cited

OTHER PUBLICATIONS

Bove et al., "Weight Bearing as a Measure of Disease Progression and Efficacy of Anti-inflammatory Compounds in a Model of Monosodium Iodoacetate-induced Osteoarthritis," Osteoarthritis and Cartilage, Nov. 2003, vol. 11(11), pp. 821-830.
Crippa et al., "Δ9-THC Intoxication by Cannabidiol-Enriched Cannabis Extract in Two Children with Refractory Epilepsy: Full Remission after Switching to Purified Cannabidiol," Frontiers in Pharmacology, Sep. 2016, vol. 7, pp. 359.
Crippa et al., "Translational Investigation of the Therapeutic Potential of Cannabidiol (CBD): Toward a New Age," Frontiers in Pharmacology, 2018, vol. 9, pp. 2009.
Cudalbu et al., "The C57BL/6J Mouse Exhibits Sporadic Congenital Portosystemic Shunts," Plos One, Jul. 2013, vol. 8(7), e69782.
Deyo and Musty "A Cannabichromene (CBC) Extract Alters Behavioural Despair on the Mouse Tail Suspension Test of Depression," Symposium on the Cannabinoids, Burlington, Vermont, International Cannabinoid Research Society, 2003, p. 146.
Elsohly and Gul., "Constituents of Cannabis Sativa," Handbook of Cannabis, 2014, pp. 28. DOI : 10.1093/acprof:oso/9780199662685. 001.0001.
Guimarhes et al., "Antianxiety Effect of Cannabidiol in the Elevated Plus-maze," Psychopharmacology, 1990, vol. 100(4), pp. 558-559.
Jou et al., "Treatment of Chemotherapy-Induced Peripheral Neuropathy Systematic Review and Recommendations," Pain Physician, Nov. 2018, vol. 21(6), pp. 571-592.
International Patent Application No. PCT/CA2020/050588, International Search Report and Written Opinion dated Jul. 29, 2020.
Izzo et al., "Inhibitory Effect of Cannabichromene, a Major Non-Psychotropic Cannabinoid Extracted From Cannabis Sativa, on Inflammation-Induced Hypermotility in Mice," British Journal of Pharmacology, 2012, vol. 166, pp. 1444-1460.
Izzo et al., "Non-Psychotropic Plant Cannabinoids: New Therapeutic Opportunities From an Ancient Herb," Trends in Pharmacological Sciences, Sep. 2009, vol. 30(10), pp. 515-557.
Kim and Hung., "An Experimental Model for Peripheral Neuropathy Produced by Segmental Spinal Nerve Ligation in the Rat," Pain, 1992, vol. 50, pp. 355-363.
Lewis et al., "Pharmacological Foundations of Cannabis Chemovars," Planta Medica, 2018, vol. 84, pp. 225-233.
Maione et al., "Non-Psychoactive Cannabinoids Modulate the Descending Pathway of Antinociception in Anaesthetized Rats Through Several Mechanisms of Action," British Journal of Pharmacology, 2011, vol. 162, pp. 584-596.
Mandolini et al., "Pharmacological Properties of Cannabidiol in the Treatment of Psychiatric Disorders: A Critical Overview," Epidemiology and Psychiatric Sciences, 2018, vol. 27(4), pp. 327-335.
Morales et al., "Molecular Targets of the Phytocannabinoids: A Complex Picture," Progress in the Chemistry of Organic Natural Products, 2017, vol. 103, pp. 103-131.
Patel et al., "The Endocannabinoid System as a Target for Novel Anxiolytic Drugs," Neuroscience & Biobehavioral Reviews, May 2017, vol. 76, pp. 56-66.
Petrocellis et al., "Effects of Cannabinoids and Cannabinoid-Enriched Cannabis Extracts on TRP Channels and Endocannabinoid Metabolic Enzymes," British Journal of Pharmacology, 2011, vol. 163, pp. 1479-1494.
R Core Team., "R: A Language and Environment for Statistical Computing," R Foundation for Statistical Computing, Vienna, Austria, 2020. URL https://www.R-project.org/.
Rao et al., "Effect of Myrcene on Nociception in Mice," Journal of Pharmacy and Pharmacology, Dec. 1990, vol. 42(12), pp. 877-878.
Reithmeier et al., "The Protocol for the Cannabidiol in Children With Refractory Epileptic Encephalopathy (CARE-E) Study a Phase 1 Dosage Escalation Study," BMC Pediatrics, Jul. 2018, vol. 18(1):221.
Russell., "Emmeans Estimated Marginal Means, Aka Least-Squares Means. R," Package Version 1.4.5. https://CRAN.R-project.org/package=emmeans, 2021.
Russo "Taming THC: Potential Cannabis Synergy and Phytocannabinoid-Terpenoid Entourage Effects," British Journal of Pharmacology, Aug. 2011, vol. 163(7), pp. 1344-1364.
Shinjyo and Marzo., "The Effect of Cannabichromene on Adult Neural Stem/Progenitor Cells," Neurochemistry International, 2013, vol. 63(5), pp. 432-437.
Wolf et al., "Cannabinoid Receptor Cb1 Mediates Baseline and Activity-induced Survival of New Neurons in Adult Hippocampal Neurogenesis," Cell Communication and Signaling, 2010, vol. 8, pp. 12.
European Patent Application No. 20200801549, Extended European Search Report dated Dec. 23, 2022.
U.S. Appl. No. 17/162,903, Non-Final office action dated Nov. 28, 2023.
European Patent Application No. 208015495, Office Action dated Feb. 19, 2024.
U.S. Appl. No. 17/162,903, Notice of Allowance dated Feb. 23, 2024.
U.S. Appl. No. 17/162,903, Notice of Allowance dated Mar. 13, 2024.
U.S. Appl. No. 17/225,968, Non-Final office action dated Apr. 10, 2024.
U.S. Appl. No. 17/225,968, Restriction Requirement dated Jan. 29, 2024.

FORMULATION FOR PAIN MANAGEMENT

CROSS REFERENCE TO RELATED APPLICATIONS

This application is a Continuation-in-Part of U.S. Ser. No. 17/162,903, filed on Jan. 29, 2021 which is the U.S. National Phase of International Patent Application PCT/CA2020/050588 filed May 1, 2020 and which is also a Continuation-in-Part thereof. This application claims the benefit of and priority to U.S. patent application Ser. No. 17/162,903, filed Jan. 29, 2021; International Patent Application PCT/CA2020/050588 filed May 1, 2020; U.S. Provisional Patent Application No. 62/842,696; filed on May 3, 2019; and U.S. Provisional Patent Application No. 63/011,508, filed Apr. 17, 2020, the contents of which are hereby incorporated by reference.

FIELD

The present disclosure relates generally to formulations for medicinal use. More particularly, the present disclosure relates to cannabinoid formulations for use in pain management.

BACKGROUND

Individuals managing pain often turn to medicinal options that offer pain alleviation, but are accompanied by unintended side-effects such as stomach upset, constipation, and risk of addiction. Alternatives to opiate drugs are urgently needed.

Cannabinoids are a group of structurally similar compounds isolated from *cannabis* plants, which activate cannabinoid receptors and ion channels in cells. Cannabinoids may be synthesized or may be isolated from *cannabis* plants or plant extracts (herein: a cannabinoid-containing plant extract). Cannabinoids can be isolated from plants or extracts to the extent that they are obtained in nearly pure, or essentially pure form, free of significant amounts of other naturally occurring compounds, such as other cannabinoids or plant-derived molecules such as terpenes. Known cannabinoids include but are not limited to tetrahydrocannabinol (THC); cannabidiol (CBD); cannabichromene (CBC); tetrahydrocannabidivarin (THCV); tetrahydrocannabinolic acid (THCA); cannabigerol (CBG); cannabidivarin (CBDV), cannabinol (CBN), and cannabidiolic acid (CBDA). *Cannabis* plants may be bred to have different amounts of a certain cannabinoid, as may be desirable for different purposes. THC and CBD have, to date, been considered as the predominant cannabinoids of interest.

CBD has been widely studied medicinal effects. CBD is regarded as having an effect on 5HT1A receptor-mediated neurotransmission, as well as on anandamide metabolism and activation of TRPV1 receptor channels that facilitate CB1- and CB2-mediated responses (Crippa J S 2018).

$\Delta^9$-THC exerts partial agonistic activity on CB1 and CB2 receptors with high binding affinity with CB1 receptor leading to its psychoactive activity.

Cannabichromene (CBC) is a major non-psychotropic cannabinoid naturally found in the *Cannabis sativa* plant.

The proportion of each of these cannabinoids in the *cannabis* plant is, however, dependent on environmental growth conditions, geographical location, genetics, and chemotype (Lewis M A 2017).

CBC has moderate affinity (Ki~100 nanomolar) only for CB2 receptors and binds to CB1 receptors only at concentrations higher than 1 micromolar (Shinjyo & De Marxo, 2013). The major CBC activity in brain has been suggested to be partly dependent on indirect activation of CB1 receptor by inhibition of cellular uptake of anandamide (De Petrocellis et al., 2011) and activation of TRPA1 (Transient Receptor potential A1) channels (Izzo et al., 2012). In fact, CBC is found to be the most potent agonist of all the phytocannabinoids at TRPA1 channels (Maione et al., 2011). CBC has also shown anti-inflammatory effects (Izzo et al., 2012).

It has been demonstrated that CBD can act synergistically with $\Delta^9$-THC and contribute to the analgesic effect of medicinal-based *cannabis* extract (Russo 2011).

The agonistic activity of CBC with CB1 and CB2 receptors can offer a promising approach to potentiate the effect of other cannabinoids that exert their activities via binding and activation of CB1 an CB2 receptors.

Medicinal uses of cannabinoids are known, and formulations specifically to treat pain have been described. WO2007/083098 A1 (GW Pharma Ltd) describes cannabinoid-containing plant extracts for treatment of neural degeneration. U.S. Patent Publication No. US2016/0106705 (United *Cannabis* Corp.) describes *cannabis* extracts having at least four cannabinoids and a terpene or flavonoid for use in relieving anxiety, pain, and related disorders. WO2016/044370 A1 (India Globalization Capital Inc.) teaches a topical pain-relieving formulation containing a combination of THC, CBD and cobalamin. WO2013/165251 A1 (ECHO Pharmaceuticals BV) describes a thin film evaporation method for obtaining THC-containing isolates, which may have trace only amounts of CBN or CBD. In WO2012/144892 A1 (Fytagoras BV), the use of acidic cannabinoids such as THC, CBD, and other cannabinoids for enhancing an animal's natural cellular resistance to disease is described. Further, in WO2012/160358 A1 (GW Pharma Ltd.), the use of at least one of CBG, CBC, CBDV and THCV as a treatment of neuropathic pain is described.

The potential of cannabinoid combinations for medicinal uses has not been fully explored. It is desirable to provide a cannabinoid formulation with beneficial properties for use in the management of pain.

SUMMARY

It is an object of the present disclosure to obviate or mitigate at least one disadvantage of previous formulations for the management and treatment of pain.

A method for pain management in a subject in need of managing pain, such as neuropathic pain, is described. The method comprises administering to the subject an effective amount of a formulation comprising tetrahydrocannabinol (THC), cannabichromene (CBC), and cannabidiol (CBD) as primary cannabinoids, and an excipient; wherein the primary cannabinoids comprise or consist of, on a weight % basis: 30%-45% THC; 9%-35% CBC; and 30%-45% CBD.

The formulation includes cannabidiol (CBD), (−)-trans-delta-9-tetrahydrocannabinol ($\Delta^9$-THC, or "THC" herein), and cannabichromene (CBC) in amounts aimed at managing or treating pain in individuals in need thereof. The formulation comprises THC, CBC, and CBD as primary cannabinoids, together with one or more excipient, diluent or carrier. The primary cannabinoids comprise or consist of, on a weight % basis of the total primary cannabinoids: 30%-45% THC; 9%-35% CBC; and 30%-45% CBD. The types of pain to be managed with the formulation include but are not limited to the treatment of pain due to cancer, injury, accident, surgery, inflammation, tissue damage, arthritis (including rheumatoid arthritis), joint pain, pain from infection, gastrointestinal pain, diabetes, diabetes neuropathy, post-shingles neuralgia, neuropathic pain, peripheral neuropathy or multiple sclerosis. An exemplary ratio of the primary cannabinoids may be, for example: 5:1:5 or 5:5:5 of THC:CBC:CBD.

There is described herein a method of pain management for a subject in need thereof. The method comprises administering to the subject a first formulation and a second formulation at different times of a multi-dose daily regime. The first formulation comprises cannabichromene (CBC) and cannabidiol (CBD) as primary cannabinoids, and an excipient. The primary cannabinoids in the first formulation comprise or consist of, on a weight % basis: 17%-54% CBC; and 46%-83% CBD. The second formulation comprises tetrahydrocannabinol (THC), cannabichromene (CBC), and cannabidiol (CBD) as primary cannabinoids, and an excipient. The primary cannabinoids in the second formulation comprise or consist of, on a weight % basis: 30%-45% THC; 9%-35% CBC; and 30%-45% CBD. The first and second formulation may be provided together as a formulation pairing, for example in the form of a kit with instructions for pain management.

Other aspects and features of the present disclosure will become apparent to those ordinarily skilled in the art upon review of the following description of specific embodiments.

BRIEF DESCRIPTION OF THE FIGURES

Embodiments of the present disclosure will now be described, by way of example only, with reference to the attached Figures.

DETAILED DESCRIPTION

Figure 1:
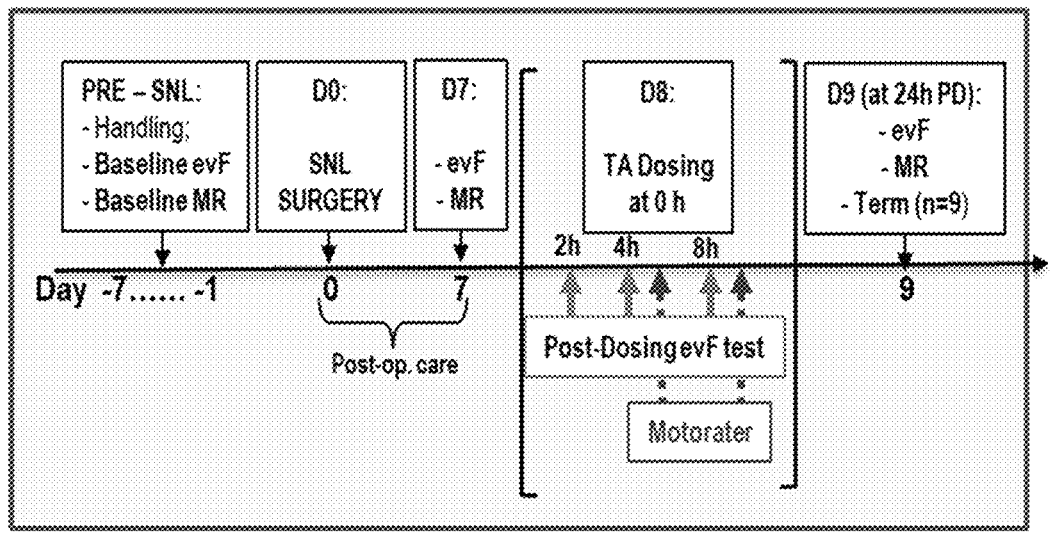
FIG. 1 depicts the study schematic for the behavioral phase described in Example 4.

Generally, the present disclosure provides a formulation for pain management, and method for managing pain.

The formulation contains three primary cannabinoid ingredients, although other cannabinoids may be present as well. For the three primary cannabinoid ingredients, the ratios of the three to one another has been optimized relative to one another. The following primary cannabinoid ingredients are present in the formulation: (–)-trans-delta-9-tetrahydrocannabinol ($\Delta^9$-THC), which is herein referred to as "THC", cannabichromene (CBC), and cannabidiol (CBD). The amount (percent wt/wt basis) of THC:CBC:CBD present in the formulation, expressed relative to each other as a percentage of these primary cannabinoid ingredients can be from 30%-45% THC; 9%-35% CBC; and 30%-45% CBD.

When such ranges are expressed as ratios, the exemplary ratios may be used. THC, CBC, and CBD, in a ratio ranging from approximately 5:1:5 to 5:5:5.

Dosages within these ratios, in mg amount, may be, for example: 5 mg THC, 1-5 mg CBC, and 5 mg CBD per dose. A higher amount per dose, but in similar ratios may be amount 8 mg THC, 1.6-8 mg CBC, and 8 mg CBD per dose. A smaller amount per dose, but in similar ratios may be 3 mg THC, 2 mg CBC, and 3 mg CBD. A wide variety of other ratios are possible.

It is the cannabichromene (CBC) content that primarily varies in this formulation, while the THC and CBD content is provided in similar amounts that are generally equal to or greater than the amount of CBC. Thus, for example, CBC could be present in an amount that is less than (as low as about one fifth of) the THC and CBD amounts, alternatively, all three primary cannabinoid ingredients could be present in roughly similar quantities.

Accordingly, there is provided herein a formulation for use in a method of pain management by a subject in need thereof, said formulation comprising tetrahydrocannabinol (THC), cannabichromene (CBC), and cannabidiol (CBD) as primary cannabinoids, and an excipient; wherein the primary cannabinoids comprise or consist of, on a weight % basis:

30%-45% THC;
9%-35% CBC; and
30%-45% CBD.

The formulation so used may be employed for management of pain due to cancer, injury, accident, surgery, inflammation, tissue damage, arthritis, joint pain, pain from infection, gastrointestinal pain, diabetes, diabetes neuropathy, post-shingles neuralgia, neuropathic pain, peripheral neuropathy or multiple sclerosis.

The primary cannabinoids may be present in the formulation in amounts according to a ratio of THC:CBC:CBD ranging from 5:5:5 to 5:1:5.

The formulation may be prepared in a dosage form selected from the group consisting of a pill, tablet, gel capsule, syrup, oil-based spray, and liquid oil form.

The formulation may provide a total amount of from about 1 mg to about 25 mg of primary cannabinoid per dose, preferably from about 5 mg to about 20 mg. For example, the formulation can provide the subject with THC:CBC:CBD in amounts of up to 20:20:20 mg per dose, preferably in the range of from 5:5:5 to 10:10:10 mg per dose.

A method for pain management in a subject in need thereof is provided, comprising administering to the subject an effective amount of a formulation comprising tetrahydrocannabinol (THC), cannabichromene (CBC), and cannabidiol (CBD) as primary cannabinoids, and an excipient; wherein the primary cannabinoids comprise or consist of, on a weight % basis:

30%-45% THC;
9%-35% CBC; and
and 30%-45% CBD.

According to the method, the pain to be managed may be pain due to cancer, injury, accident, surgery, inflammation, tissue damage, arthritis, joint pain, pain from infection, gastrointestinal pain, diabetes, diabetes neuropathy, post-shingles neuralgia, neuropathic pain, peripheral neuropathy or multiple sclerosis.

The formulation used in the methods may be one in which the primary cannabinoids are present in amounts according to a ratio of THC:CBC:CBD ranging from 5:5:5 to 5:1:5. In the method, the formulation may be administered in a dosage form selected from the group consisting of a pill, tablet, gel capsule, syrup, oil-based spray, or liquid oil form. The method may involve administration of a total amount of from about 1 mg to about 25 mg of primary cannabinoid per dose, preferably from about 5 mg to about 20 mg per dose. The formulation may be administered in amounts to provide the subject with THC:CBC:CBD in amounts of up to 20:20:20 mg per dose, preferably in the range of from 5:5:5 to 10:10:10 mg per dose.

A method of pain management in a subject in need thereof is described, which comprises, administering to the subject a first formulation and a second formulation at different times of a multi-dose daily regime. The first formulation comprises cannabichromene (CBC) and cannabidiol (CBD) as primary cannabinoids, and an excipient. The primary cannabinoids in the first formulation comprise or consist of, on a weight % basis: 17%-54% CBC; and 46%-83% CBD. The second formulation comprises tetrahydrocannabinol (THC), cannabichromene (CBC), and cannabidiol (CBD) as primary cannabinoids, and an excipient. The primary cannabinoids in the second formulation comprise or consist of, on a weight % basis: 30%-45% THC; 9%-35% CBC; and 30%-45% CBD.

The method may be used for treatment of pain due to cancer, injury, accident, surgery, inflammation, tissue damage, arthritis, joint pain, pain from infection, gastrointestinal pain, diabetes, diabetes neuropathy, post-shingles neuralgia, neuropathic pain, peripheral neuropathy or multiple sclerosis.

Exemplary ratios of the primary cannabinoids may be present in the first formulation in amounts of CBC:CBD ranging from 1:5 to 5:5. Exemplary ratios of primary cannabinoids in the second formulation may range from THC:CBC:CBD from 5:5:5 to 5:1:5.

In the described method, the first and second formulations may be prepared in a dosage form independently selected from the group consisting of a pill, tablet, gel capsule, syrup, oil-based spray, and liquid oil form.

The method may provide from about 1 mg to about 25 mg of primary cannabinoid per dose, for example from about 5 mg to about 20 mg of primary cannabinoid per dose.

A formulation pairing is described for use in a method of pain management by a subject in need thereof. The formulation pairing comprises a first formulation and a second formulation for use at different times of a multi-dose daily regime. The first formulation comprises CBC and CBD as primary cannabinoids on a weight % basis of: 17%-54% CBC; and 46%-83% CBD, together with an excipient. The second formulation comprises THC, CBC, CBD as primary cannabinoids, on a weight % basis of: 30%-45% THC; 9%-35% CBC; and 30%-45% CBD, together with an excipient.

The formulation pairing may be used by individuals who may wish to defer psychoactive effects of THC to certain times of day, when managing pain due to cancer, injury, accident, surgery, inflammation, tissue damage, arthritis, joint pain, pain from infection, gastrointestinal pain, diabetes, diabetes neuropathy, post-shingles neuralgia, neuropathic pain, peripheral neuropathy or multiple sclerosis.

The formulation pairing may comprise primary cannabinoids present in the first formulation in amounts according to a ratio of CBC:CBD ranging from 1:5 to 5:5, and primary cannabinoids in the second formulation in amounts of THC:CBC:CBD ranging from 5:5:5 to 5:1:5. The ratio of CBC:CBD within the first and second formulations may be the same or different within the formulation pairing. For example, when the same, the CBC:CBD ratio may be consistently 5:5 in both the first and the second formulation. When different between the first and second formulations, the ratio may be from 1:5 to 5:5, such as 1:5 in the first formulation and 3:5 in the second formulation (which also contains THC), for a three-component ratio of 5:3:5 of THC:CBC:CBD.

The first and second formulations of the pairing need not be in the same dosage form, and may differ depending on a subject's preference. The first and second formulations can be in a form independently selected from the group consisting of a pill, tablet, gel capsule, syrup, oil-based spray, and liquid oil form.

The formulation pairing may provide a total amount of from about 1 mg to about 25 mg of primary cannabinoid per dose, for example from about 5 mg to about 20 mg of primary cannabinoid per dose. With regard to the amount of CBC in the first and second formulations, these may provide the subject with CBC in amounts of up to 20 mg per dose, such from 5 to 10 mg per dose.

The formulation pairing may be packaged together, for example provided a kit together with instructions for use in a multi-dose daily regime.

Exemplary multi-dose daily regimes may include a periodic or timed multi-dose regime of every 4 to 6 hours, or may be associated with daily events such as waking, meal time, and bed time. The first formulation from which THC is absent may be administered in the earlier part of the day when an individual may wish to avoid any psychoactive effect of THC for typical daytime activities and interaction, whereas the second formulation containing THC may be administered in the later part of the day, when the same individual may find the effect of THC desirable. For example, the second formulation may be utilized in the evening or at bed time. The desired time of day may depend on when an individual sleeps or naps, which may be influenced by a working schedule, such as for individuals who may work night shifts.

Primary Cannabinoids. The term "primary" is meant to indicate the cannabinoids that are primarily responsible for the intended effect of pain management, as described herein. THC, CBC, and CBD are primary cannabinoids in this context. If another cannabinoid is present in the formulation in a lower, an approximately similar, or even a higher amount, the quantity present would not mean that the cannabinoid is a "primary" component of the formulation, although such additional cannabinoids may be present.

Cannabinoid Sources. The primary cannabinoids THC, CBC, and CBD may be present in the formulation from natural sources, such as from one or more *cannabis* plants, an in particular extracts thereof. Or the cannabinoids may be obtained from one or more isolated sources, or from a synthetic source where one or more of the desired cannabinoids is synthesized. A blend of natural and synthetic cannabinoids may be used so that a natural source with a variable content (due to growing conditions or other reasons), may be standardized to pre-determined amounts using adjustment with synthetic or isolated sources.

An extract may be obtained from a plant that is specially modified or grown under conditions conducive to production of a cannabinoid ratio particularly suited to the desired primary cannabinoid ratio, without needing to dramatically alter or supplement the amount of any of the primary cannabinoids present.

If purification of cannabinoids is desired extraction methods such as an ethanolic extraction, or a $CO_2$ based extraction may be used.

Plants may be bred or cultured, or growth conditions can be optimized to reflect the requisite ratio of THC:CBC:CBD. Further, two or more plants or extracts bearing ratios differing from the intended ratio may be combined in amounts that result in the desired pre-determined ratio.

Other cannabinoids may be incidentally present in the formulation, and if present, the quantities of such additional cannabinoid ingredients would not reduce the pain management features of the formulation.

Pain Management. The intended use of this formulation for pain management may include cancer-related pain as well as non-cancer-related pain, such as acute pain from injury, accident, surgery, inflammation, or from tissue-damaging conditions such as arthritis and joint pain, pain from infection, gastrointestinal pain, diabetes, diabetes neuropathy, post-shingles neuralgia, neuropathic pain, peripheral neuropathy, multiple sclerosis or from other sources of pain. Inflammatory pain, neuropathic pain, or pain in which inflammation is a contributing underlying cause, that may be attributed to increased excitability of peripheral nociceptive sensory fibres can be addressed by the present formulation. The altered activity of ion channels in sensory neurons, causing pain, can be lessened. This can address a number of conditions associated with chronic inflammation.

Subjects and Populations. The formulation may be used by humans or by pets (companion animals such as dogs or cats), as well as for working animals such as horses.

Subjects in need of a therapeutic effect for pain management in the intended indications may use the formulation prior to, during, or after the medical event or need arises. Cancer pain can be debilitating for a number of reasons, and cancer treatments can also lead to painful episodes. Management with the formulation described herein can avoid problems inherent with opiate use, such as constipation and addiction. Addition can lead to overuse, and eventually illegal sourcing of formulations that are unpredictable in composition, which may lead to overdose.

Regarding non-cancer pain, for example, prior to undergoing surgery where the pain can generally be anticipated, the formulation may be used prophylactically to lessen the pain that is anticipated. For the pain of an injury or unexpected damage from an accident, the formulation may be used acutely or on an ongoing basis in place or harsher or more damaging analgesic drugs such as opioids or NSAID pain killers.

Mode and Forms of Delivery. The formulation is amenable to oral delivery, such as in a pill, tablet, gel capsules, syrup, oil-based spray, or liquid oil form. The oral form may be provided in a food or as a food supplement, which may be added to a food to be more palatable or readily consumed by a subject. Topical or nasal absorption is possible. A fat-soluble carrier, or nano- or micro-particles or emulsions may be used so that the highly fat-soluble cannabinoids can be more readily absorbed. The formulation may be prepared as an injectable, for intravenous, intramuscular, or intraocular delivery. The formulation may be delivered in a vapor, such as by vaping, in a vaporizer or puffer, or may be heated to cause volatilization and inhalation which could be considered as "smoking".

Administration. It is understood that administration encompasses self-administration, as well as all other forms of provision. Administration by a medical practitioner such as by recommendation and/or by prescription is encompassed.

Dosages. The formulation can be delivered in relative amounts ranging from about 5:1:5 to 5:5:5 (ie—1:1:1) on a weight basis of THC, CBC, to CBD. Other cannabinoids may be present in these formulations. On a per dosage basis, the total amount of primary cannabinoids may range from 0.1 mg-50 mg, for example 1 mg-25 mg, or 5 mg-20 mg per dose. If delivered in a liquid such as an oil, amounts may be expressed on a mg/mL basis, such as from 0.1 mg/mL-50 mg/mL per dose, for example 1 mg/mL-25 mg/mL, or 5 mg/mL-20 mg/mL per dose. Dosages may be used as needed depending on the severity of the pain experienced, but an individual may wish to use the formulation on an as-needed basis, ranging from once per day (or less, if not needed) to more frequently such as taking 6 doses per day, with a frequency of every 4 hours.

An exemplary formulation may be a solid dosage form such as a pill, tablet, or granule-containing capsule. Alternatively, the formulation may be liquid-based, and may contain isolated or synthetic primary cannabinoids, or may be an oil-based extract of *cannabis* with about 5 mg/mL $\Delta^9$-THC, about 1-5 mg/mL CBC and about 5 mg/mL of CBD in liquid forms such as oil, and oil-based spray, or a liquid-containing gel capsule (soft-gel capsule). If liquid-containing or gel-containing capsules are used, these may be limited in volume, for example an approximate volume of 200 μL. The milligram quantity stated above as a dosage range may be included in each such capsule, or the capsules may be formulated so as to be less concentrated in units of mg/mL. When less concentrated capsules are used, then the appropriate dosage is delivered by increasing the number of capsules consumed per dose.

Excipients and Formulation Ingredients. The formulation may incorporate any acceptable excipients known in formulating drugs or cannabinoids. Such ingredients may include starch, cellulose, alginates, colloidal silicon, lubricants such as stearates, salts, aqueous and non-aqueous (fat soluble) ingredients. The usual formulation considerations would be brought to bear, as one of skill in the art would understand.

Example 1

Formulation for Use in Cancer Pain Management

The pain that accompanies cancer is highly variable depending on the type of cancer, the treatment involved, and whether tumors themselves are causing the subject discomfort.

An individual experiencing the pain of a stage 4 carcinoma may use the formulation to manage this pain. Then individual may consume orally, on a regular basis such as every 6-hours, a dose of the following oil-based cannabinoid formulation.

The formulation comprises 5 mg/mL THC, 1 mg/mL CBC, and 5 mg/mL CBD, in an oil-based liquid. At the appropriate interval, the individual may take 1 mL orally.

Initially, the individual may begin by consuming 1 mL of the formulation at a frequency of twice per day. The dose may be titrated to a higher amount over time as the individual becomes accustomed to the formulation, until a dose of 1 to 2 mL, taken from 4 to 6 times per day is reached.

Example 2

Managing Pain as a Result of Surgery

The pain of recovering from surgery can, at times, be anticipated in advance of the surgical procedure.

Prior to a surgery, and individual may wish to mitigate stress or worry by knowing effective pain relief is available. Following a surgery, or when a surgery does not require general anesthetic or extensive fasting, such as an oral surgery (fillings or root canal procedures), the individual may consume orally, in advance if possible, or following the surgery, a dose of the following pill-based cannabinoid formulation.

The formulation comprises 5 mg THC, 3 mg CBC and 5 mg CBD, in an pill, tablet, or soft-gel capsule form. The individual may take 1 or 2 of such a pill, tablet, or capsule orally. Optionally, a high-fat food may be simultaneously consumed to assist in efficiency of intestinal absorption, but only at a time when food consumption is permitted according to the surgical regime.

Example 3

Formulation for Use in Pain Management Following Injury

The pain that accompanies an acute and unexpected accident or injury can be debilitating to the individual as their recovery and healing proceeds.

An individual experiencing the acute pain brought on by such an unexpected event may use the formulation to manage this pain. Then individual may consume orally, on a regular or as-needed basis, a dose of the following encapsulated oil-based cannabinoid formulation until the pain subsides to a tolerable level.

The formulation is present in soft-gel capsules having an approximate volume of 200 μL per capsule. Each capsule comprises 5 mg THC, 2 mg CBC, and 5 mg CBD, in an oil-based liquid. The soft-gel capsule encapsulates the oil-based liquid with a gelatin-based shell that may incorporate other commonly known gel capsule ingredients, such as glycerin or sorbitol, so as to permit ease of swallowing. At the appropriate interval, the individual may take 1 capsule orally.

Initially, the individual may begin by consuming 1 capsule at a frequency of twice per day. The dose may be increased to a higher amount if the initial dose is well tolerated, and as the individual becomes accustomed to the formulation. A dose of 1 to 2 capsules, taken from 4 to 6 times per day may be used when the pain is most acute. Over time, as the individual recovers and heals, the frequency of use may be titrated down to a dose of 1 capsule twice per day, or even less frequently is used on an as-needed basis.

Example 4

Formulation for Pain Management

Introduction. Globally, up to 10% of the population are affected by neuropathic pain (Bouhassira D, 2008; Colloca L, 2017) as a comorbidity with chemotherapy, diabetes, inflammatory and infectious disorders (Colloca L, 2017). Yet, an effective and safe treatment remains unfound. Several cannabinoids have been shown to possess efficacy as antinociceptives. In this example, a unique formulation is described for treatment of chronic pain. Neuropathic pain is characterized with burning and electrical-life sensations, pain causing by non-painful stimulants, and upon having persist symptoms, leads to sleep disturbance, anxiety and depression and impairment in quality of life (Colloca L, 2017). The study was designed to focus on the phenotypic profile of neuropathic pain and address challenges for clinical translation.

This study provides a comprehensive behavioral phenotypic assessment of the impact of cannabinoid treatments on chronic neuropathic pain. Using two different measures of mechanical threshold testing, electronic von Frey and kinematic assay by Gait analysis, significant reduction of mechanical hyperalgesia and allodynia ipsilateral to the ligated nerve were observed upon treatment with cannabidiol (CBD), delta 9-tetrahydrocannabinol ($\Delta^9$-THC), Cannabichromene (CBC) at 1:1:1 ratio. CBD:THC:CBC at ratio of 5:5:5 mg/kg or 10:10:10 mg/Kg displayed a robust reduction in mechanical hypersensitivity and a strong reversion of tactile allodynia and effectively improved kinematic performance of SNL-induced neuropathic pain. Strikingly, this formulation was attributed to superior analgesic effect when compared to Pregabalin, a GABA analogue (Gamma aminobutyric acid) that is among the first-line treatment choices for neuropathic pain. This analgesic effect seems to be largely mediated by cannabichromene present in the formulation.

These results illustrate that the current formulation (CBD:THC:CBC at 1:1:1 ratio) potently reduces neuropathic pain and offers a new replacement for opioids as painkiller. Furthermore, addition of cannabichromene robustly mitigates the analgesic effect of CBD and Δ9-THC. This finding shows that adding CBC enables the possibility of a significant reduction in the daily dose and total intake of CBD and Δ9-THC in patients with chronic pain. Importantly, CBD:THC:CBC at 1:1:1 ratio offers a new solution where patients' quality of life is impaired because of poor outcome of opioids, risk of opioid dependency, increased drug intake and several visits to healthcare providers.

Purpose Of The Study. The objective of this study is to evaluate the effect of distinct doses of 3 cannabinoids on the intensity of SNL-induced mechanical hypersensitivity and altered kinematic performance as a validated model of chronic neuropathic pain. The studied cannabinoids are cannabidiol (CBD), cannabichromene (CBC), and delta 9-tetrahydrocannabinol ($\Delta^9$-THC). Spinal nerve ligation surgery causes partial denervation within the peripheral (sciatic) nerve, thereby evoking tactile hypersensitivity (allodynia) within the sciatic nerve innervation area. The SNL rat model was originally described in 1992 (Kim S H, 1992). Cannabinoids possess several functions according to their reactions with the endocannabinoid system. They are among the most promising candidates for studying different pain types.

The study in-life was conducted via the following steps:
N=7-10 Rats per group
Day-7 (OR Day −1 from Surgery):
    assessment of baseline tactile allodynia (mechanical sensitivity of the naïve rats) using the electronic von Frey test (evF);
    recording of baseline fine motor kinematics
D0: SNL-surgery;
D0-D6: Post-operative care period
D7: —evF to define the injury baseline allodynia and to obtain the pre-dosing test results;
    kinematic assay to define the injury baseline motor deficits and to obtain the pre-dosing test results
D8: —administration of CBD, CBC and THC on D8
    evF at 2 h, 4 h, and 8 h post-dosing
    Kinematic assay at 5 h and 9 h post-dosing (PD)
D9: —evF at 24 h PD
    Kinematic assay after the evF test
    Euthanization of 9 rats/group Materials and Methods Animals All animal experiments were performed as specified in the license authorized by the national Animal Experiment Board of Finland and according to the National Institutes of Health (Bethesda, Md., USA) guidelines for the care and use of laboratory animals.

In total, 180 male Sprague-Dawley male rats were purchased from Charles River Germany and subjected to the study procedures. The body weight of the rats was 200-300 g on the day of SNL surgery. Prior to SNL surgery, upon the handlings and baseline tests—the number of animals were approximately 5-10% larger, in purpose of anticipating the rare but possible situations which require animal replacements (e.g. innately oversensitive animals). Animals were housed at a standard temperature (22±1° C.) and in a light-controlled environment (lights on from 7 am to 8 pm) with ad libitum access to food and water.

All animals were operated by spinal nerve ligation; all groups comprised n=15. The treatment groups received the following test article administrations:
    Group 1: treated on D8 with vehicle (0.9% saline)
    Group 2: treated on D8 and on D9 with Pregabalin (50 mg/kg)
    Group 3: treated on D8 with CBD (5 mg/kg) and THC (5 mg/kg)
    Group 4: treated on D8 with CBD (5 mg/kg) and CBC (1 mg/kg) and THC (5 mg/kg)

Group 5: treated on D8 with CBD (5 mg/kg) and CBC (5 mg/kg) and THC (5 mg/kg)

Group 6: treated on D8 with CBD (10 mg/kg) and CBC (10 mg/kg)

Group 7 treated on D8 with CBC (10 mg/kg) and THC (10 mg/kg)

Group 8 treated on D8 with CBD (10 mg/kg) and THC (10 mg/kg)

Group 9 treated on D8 with CBD (10 mg/kg) and CBC (10 mg/kg) and THC (10 mg/kg)

Group 10 treated on D8 with CBD (10 mg/kg) and CBC (2 mg/kg) and THC (10 mg/kg)

All rats followed the same study design until completion of the D9 behavioral tests.

Table 1 shows the treatment details.

These results are presented for a 5 mg/kg treatment subset. The 10 mg/kg treatment subset results are presented below.

TABLE 1

Compound Doses and Treatment Group Information for the behavioral study phase (D0-D9)

| Group | n | Pregab. (mg/kg) | CBD (mg/kg) | CBC (mg/kg) | THC (mg/kg) | Dosing Vol. (mL/kg) | Vehicle | Doses/Rat | evF Test | MR Test |
|---|---|---|---|---|---|---|---|---|---|---|
| 1 | 15 | 0 | 0 | 0 | 0 | | | 1 | BL, | BL, |
| 2 | | 50 | 0 | 0 | 0 | | Saline | 2 | D7, | D7, |
| 3 | | 0 | 5 | 0 | 5 | | Corn | 1 | D8 | D8 |
| 4 | | 0 | 5 | 1 | 5 | | oil; | | (3 | (2 |
| 5 | | 0 | 5 | 5 | 5 | | 10% | | time- | time- |
| 6 | | 0 | 10 | 10 | 0 | | EtOH; | | points), | points), |
| 7 | | 0 | 0 | 10 | 10 | | 5% | | D9 | D9 |
| 8 | | 0 | 10 | 0 | 10 | | Kolliphor | | | |
| 9 | | 0 | 10 | 10 | 10 | | | | | |
| 10 | | 0 | 10 | 2 | 10 | | | | | |

FIG. 1 provides a schematic outline of the study paradigm. The outline is in the form of a schematic presenting the behavioral phase of the study, conducted to all study animals until D9 tests. Motorater test timepoints on D8 are not displayed, as the two test rounds took place first after finishing the 4 h evF, and second after finishing the 8 h evF.

Test Articles and Formulation. The Test Articles were handled and stored under standard operative procedures. The dose formulations were prepared according to detailed instructions provided by the vendor.

Drug Administration. Test articles, their vehicle, or Pregabalin (positive control drug) were administered according to table 1 on study day 8 to all study animals. The route of administration of Cannabinoids or vehicle was intragastric (p.o.), while Pregabalin was administered intraperitoneally (i.p.). In addition to D8, pregabalin was administered on D9, at 2 h prior to the evF test.

Spinal Nerve Ligation (SNL) Surgery. The animals were enrolled to SNL surgery in daily cohorts of n=6. The rats first received an intraperitoneal dose of 0.03 mg/kg buprenorphine (Temgesic), minimum of 30 minutes prior to the surgery, to alleviate the operative and postoperative pain unrelated to neuropathy. Prior to spinal nerve ligation (SNL) procedure, the rats were anesthetized with isoflurane in 70% N$_2$O and 30% O$_2$; with a flow rate of 300 ml/min. Anesthesia was inducted in a chamber with 5% isoflurane for 2-3 min, and maintained through a snout mask with 1-2% isoflurane thereafter. A homeothermic blanket system was used for the rectal temperature to be monitored and maintained at 37.0° C.±1.5° C. during the operation.

A dorsal incision extending from L3 to S2 was performed to the medial dorsal area of the rat using aseptic technique. The L6/S1 posterior interarticular process was exposed using a combination of blunt and sharp dissection. The L6 transverse process in the spinal column was visualized and partially removed without manipulating the nerves, followed by exposing the L4 and L5 spinal nerves distal to their emergence from the intervertebral foramina.

The L5 nerve was ligated tightly with 6-0 silk suture. The L6 nerve was then located caudal and medial to the sacroiliac junction and tightly ligated with 6-0 silk suture, similarly to L5. Both ligatures were performed as double knots.

After performing the ligatures, the muscle layers, connective tissue and skin were closed and animals allowed recovery from anesthesia in a homeothermic cage. Rats were monitored until fully awake and moving in the cage.

Postoperative care period occurred twice-daily for ad 7 days following surgery, and included the following procedures. Careful observation of the general condition and welfare along with monitoring the operated paw and gait of the animal. The surgical wound and sutures were checked—and disinfected properly when required—twice a day, until the wound was properly closed. 0.03 mg/kg buprenorphine s.c. was administered upon first two postoperative days, at approximately every 12 hours. Rehydration with 4 ml of sterile saline i.p. directly after the surgery, continuing twice a day ad 7 days, or until no further weight loss occur. Any clear signs of pain, motor deficits or health issues beyond model and surgery related were recorded and animals with any paralysis or other model-unrelated motor deficit were excluded from further testing.

Tactile Allodynia Test (evF) and Pre-Handling and Baseline evF. In this study, mechanical sensitivity to touch stimuli was defined at four timepoints by using electronic von Frey (evF) device along with the attached analysis software (Somedic®, Sweden).

Before subjecting the rats to the baseline evF, they were pre-handled for 2-3 min on two consecutive days, in purpose of decreasing oversensitivity in the test. Pre-handling was performed at a maximum of 3 days prior to baseline tests. Baseline evF took place at a minimum of 5 days after their arrival to CR animal facility, and at maximum of 5 days preceding the surgery day (d0).

Rats displaying inborn oversensitivity were disqualified from the study. Oversensitivity was defined as baseline paw withdrawal threshold (PWT) of <20 g with 1 mm probe. Following the baseline evF test, the rats were weighed, numbered, and distributed into treatment groups evenly regarding the baseline PWT and body weight.

Prior to any procedures (handling or tests), the animals were allowed for a 60-min habituation in the room where procedures performed.

To perform the evF test, the rats were placed in individual von Frey test chambers standing on an elevated steel mesh. The rats were then allowed to adapt in the chambers, and the test per se was emerged after they have settled down followed by investigating the chamber and grooming (approximately 15 min). Test was be performed while an animals were grooming, urinating, defecating or sleeping. Further description of test procedure is provided hereinbelow.

Conducting evF Test. Mechanical allodynia were assessed by evF test prior to SNL surgery (baseline), to define the individual sensitivity levels of the study animals. Next, the evF was performed on D7 post-SNL, to assess the hypersensitivity evoked by the SNL surgery, and to provide pre-dosing sensitivity values for comparing. On D8, the animals were subjected to the test at 2 h post-dosing (PD), at 4 h PD and at 8 h PD. Subsequently, the test was performed at 24 h PD, i.e. on D9. On D9, Group 2 received Pregabalin (i.p) at 2 h prior to testing.

On any test day, the rats were allowed to adapt in the test room for approximately 1 h prior to testing. Part of this time was used to test chamber adaptation, in order to reduce the stress and facilitate testing. The test may be commenced as the animals have explored the surroundings, groomed and calmed down. A rat is not tested in case it's urinating, defecating or sleeping.

The evF apparatus was used according to the manufacturer's instructions. Briefly, upon each measurement, the force is applied to mid-plantar surface of the hind paw in a linearly increasing rate.

The used evF probe diameter was 1 mm, and the chosen ascent rate of the force 10 q/s. The linearity of force application was monitored in real time. The applied force (in grams) causing paw withdrawal was recorded by the apparatus as the result for the trial.

Notes were taken during the test so, that possible sedative effects of the test articles was distinguished from the sensory effects.

Altogether, 5 repeated measurements were applied to each hind paw at each time-point leaving a minimum of 3-min interval between the repeats. Medians of the 5 measurement repeats were determined from each paw at any given time point. Both ipsi- and contralateral paws were also tested on each test day.

Figure 2:
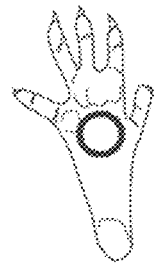
FIG. 2 depicts the test site used for the von Frey test on the plantar paw of the animals in Example 4.

FIG. 2 shows the von Frey test site on the plantar paw.

Fine Motor Kinematic Gait Analysis. The rats were subjected to gait analysis at the baseline and on study days 8, 9, 11, 14 and 17, at a minimum of 30 min after the evF test. The assay were carried out by MotoRater (TSE Systems, Homburg, Germany), with the walking mode. Prior to commencing the test, the essential body points (e.g. joints, limbs, nose, tail) were marked for tracking. The information of the gait performance was captured using a high speed camera (300 frames/second) from below and both sides. Next, the captured videos were converted to SimiMotion™ software. The raw data were obtained by tracking the marked points of the body from the videos recorded from all 3 dimensions. The raw data thus comprised correlation of the movements of different body points in coordinates related to the ground and each three dimensions.

Different gait patterns and movements were analyzed using a custom-made automated analysis system. Information about altogether over a hundred kinematic parameters were attained. These comprised e.g.:

General gait pattern parameters such as: stride time and—speed, step width, stance and swing time during a stride, and interlimb coordination.

Body posture and balance parameters, such as: toe clearance, iliac crest and hip height, hind limb protraction and retraction, tail position and movement.

Fine motor skills, including e.g. the swing speed during a stride, jerk metric during swing phase, angle ranges and deviations of different joints, and vertical plus horizontal head movements.

All Motorater data were analyzed for the distinct parameters, as well as for all combined parameters, using principal component analysis (PCA). The obtained results were produced the model phenotype in gait analysis, i.e., the difference between vehicle and cannabinoid-treated animals regarding both individual parameters and PCA.

In addition to the baseline test, the motorater tests were performed altogether four times over the course of behavioral study phase:
on D7, to assess the model-specific motor defects prior to dosing
on D8, after finishing the 4-h evF
on D8, after finishing the 8-h evF.
on D9, after finishing the 24-h evF The kinematic assay was not performed to the animals before a minimum of 30 min after evF test.

Figure 3A:
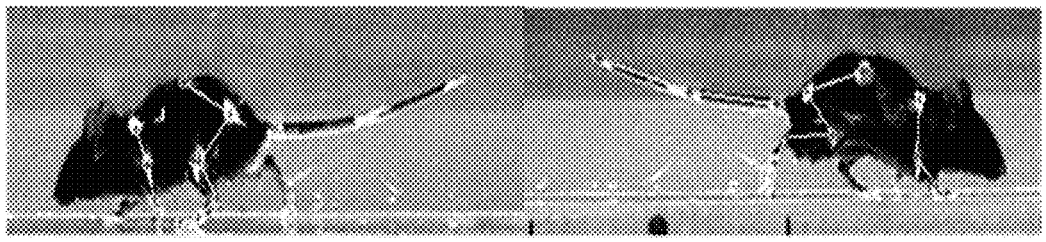
FIG. 3A depicts a photograph of animal body parts relevant to motion for MotoRater observations.
Figure 3B:
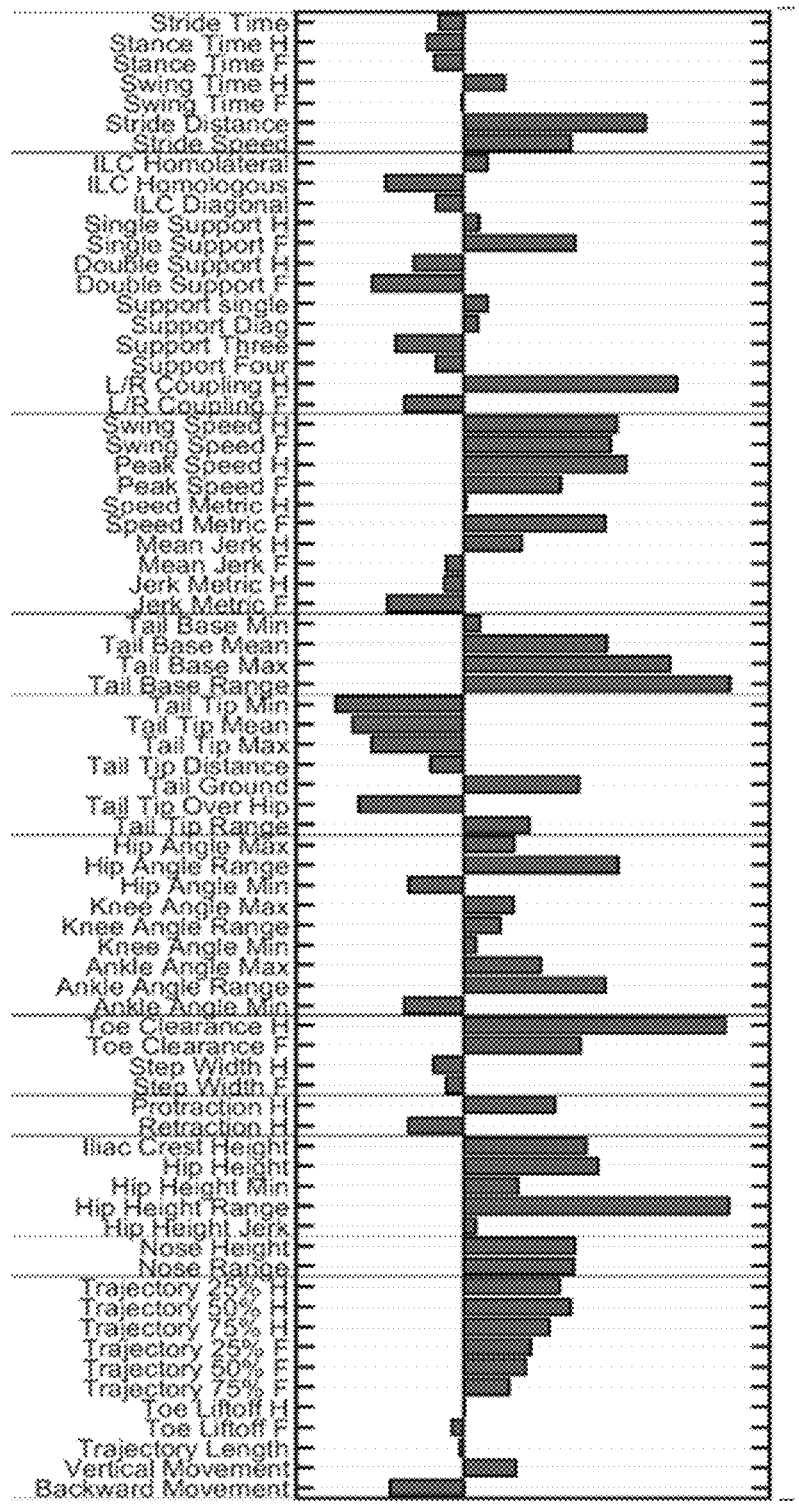
FIG. 3B is a bar graph showing changes from baseline in animal motion parameters following spinal nerve ligation (SNL) surgery in rats, as a model of neuropathic pain.

FIG. 3A and FIG. 3B show SNL induced motor phenotype, based on PCA of BL and D7 differences in all study groups.

FIG. 3A illustrates motion tracking and the kinematic model. Motion Tracking involves utilizing MotoRater to observe the animal from 3 sides simultaneously (ventral, left, right) and provides detailed readouts of ALL body parts relevant to motion, i.e. paws, ankles, joints, tail, head, hip, iliac crest etc. allowing reliable detection of subtle deviations, early symptom onset and treatment effects.

FIG. 3B illustrates the discriminant direction for "Distance from Baseline". The bar graphs illustrate which parameters changed after SNL (zero=BL or baseline). The bar length and direction indicate the weight how much each parameter is contributed in the overall score.

The motor phenotype of SNL model can be characterized and interpreted as the following combination of changes in the gait features:
The overall speed is increased which is mainly due to longer stride distance (increased step length).
The interlimb coordination is not dramatically changed, except the asymmetry in the hind limb left-right alternation rhythm is increased (L/R Coupling H)
The overall hip height and vertical range of hip movement are increased (Tail Base mean/max/range, hip height, hip height range, iliac crest height)
Tail tip position is lower (Tail tip min/mean/max)
Hip angle range is increased
Hind limb toe clearance is increased.

The overall gait scores presented on the following three slides reflect all these changes together (using the discriminant direction vector as a "yardstick"), and are presented in a way that the average score at baseline is equal to zero. The average score of all study groups at D7 is equal to 3.107 (z-score). The decrease of the overall score means that the gait performance has changed towards to the pre-SNL status (BL).

Figure 4:
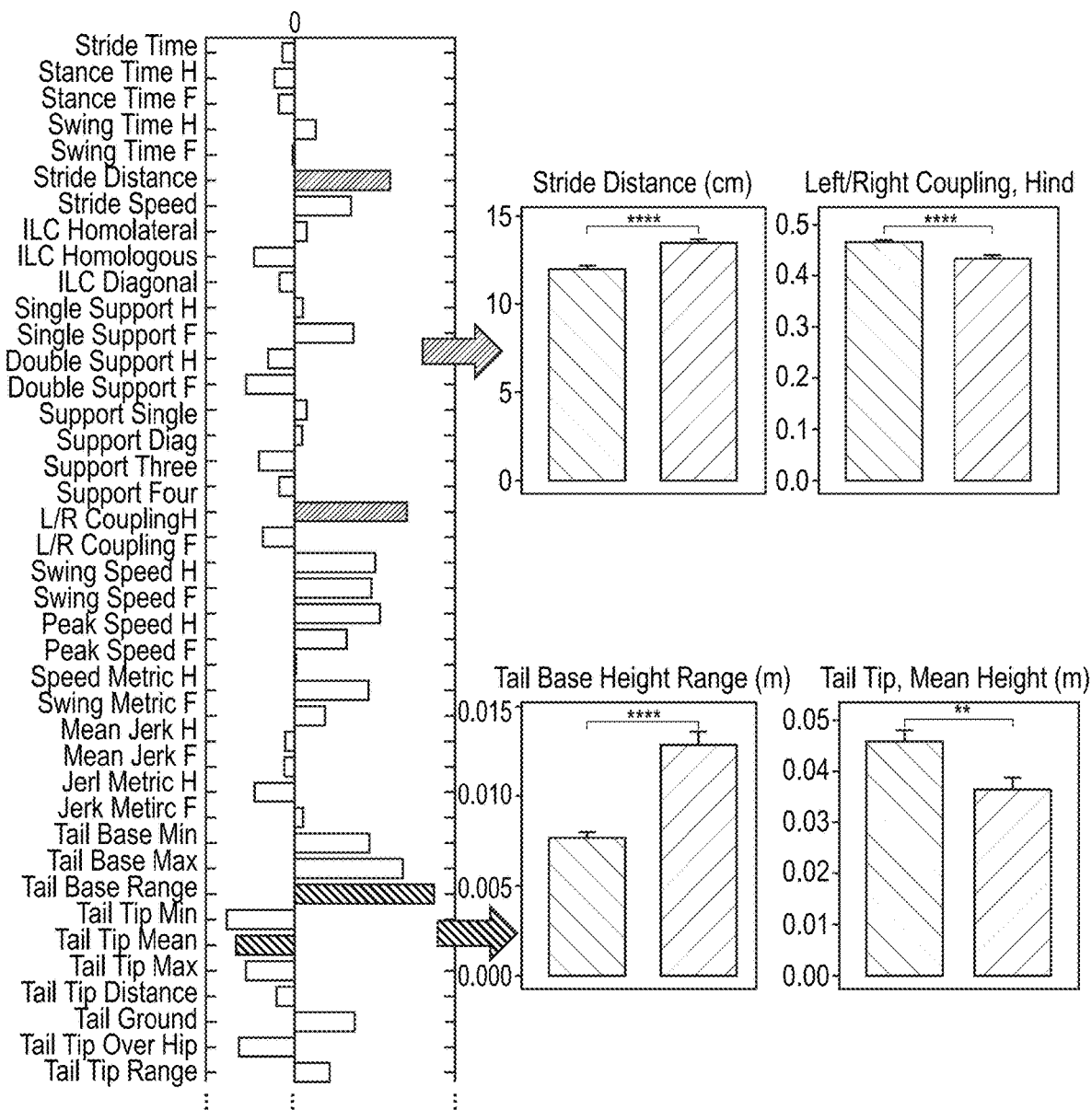
FIG. 4 provides a comparison of gait overall score changes from baseline for sham versus the SNL rat model.
Figure 4:
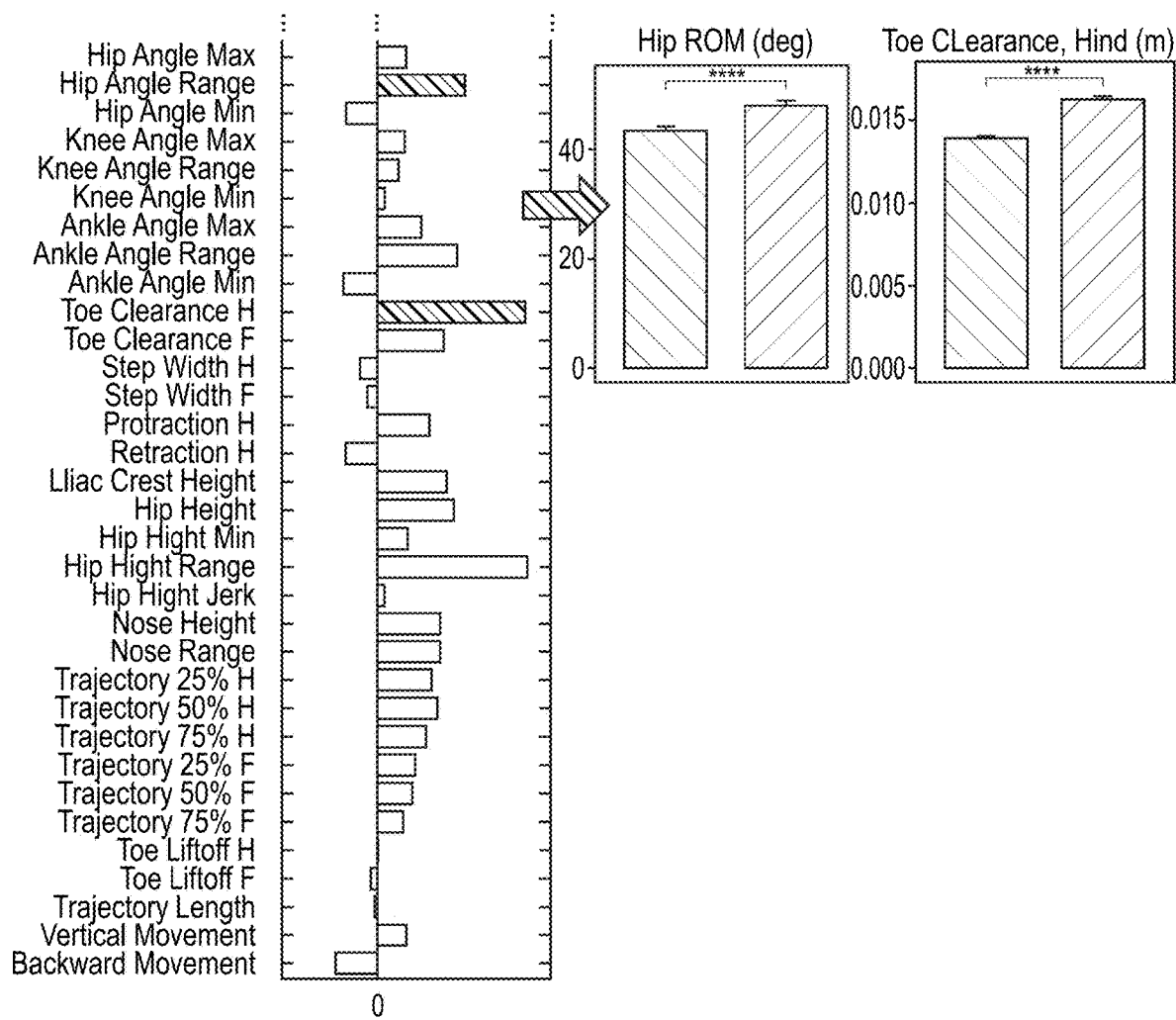

FIG. 4 illustrates gait overall score (distance from baseline), providing examples of individual gait parameters which are emphasized in the discriminant vector exhibited for sham (lighter bars on left side of pairings) versus SNL rat model (darker bars on right side of pairings). The Overall Gait score is driven by all those gait parameters together which are linked to the SNL model.

Body Weight Monitoring. The body weight of the animals was recorded at baseline evF testing, on the day of surgery (D0), and daily thereafter.

Endpoint, Blood Samples and Tissue Processing. On D9, after the last motorater test, the behavioural study phase were completed by choosing 6 rats per group to continue into the PK-phase. The rest of animals were euthanized by an overdose of $CO_2$, and decapitation.

Upon the endpoint day of the PK.-phase, on D11, the rats were terminally anesthetized with pentobarbital (60 mg/kg Mebunat). Blood samples were collected via cardiac punctures, and plasma isolated by centrifugation with 2000×g for 10 min. Separated plasma samples were transferred into clean tubes and stored in −80° C. until shipment.

Next, the animals were transcardially perfused first with PBS. Brains were detached from the skull and snap-frozen in liquid $N_2$. Thereafter, the brain samples were stored in −80° C. until shipment.

Lumbar DRGs were prepared to sight, and harvested from both sides. Lumbar DRGs L4-L6 from each side were pooled in a pre-labelled 2-ml tube (ipsilateral DRGs into one tube; contralateral DRGs to another), and post-fixation performed in 10% commercial formalin for 24 h (+4° C.). Finally, the DRG samples were briefly flushed with 0.1 M PBS, and stored in the buffer in +4° C. until and during the shipment.

General Health Status and Humane Endpoints. Animals were monitored daily by laboratory personnel. In the case that general health status of an animal has significantly worsened, it was sacrificed by an overdose of $CO_2$, and decapitated. Definitions of acceptable endpoints include: no spontaneous movements and inability to drink or eat in a 24-h observation period, massive bleeding, spontaneous inflammation, missing anatomy, swelling or tumors larger than 20 mm, and inability to right itself for a 30-s period.

In addition, model specific end-point criteria apply:
  The wound suture opens three times (at the first time new stitching was done; at the second time, tissue glue may be used in addition).
  Wound inflammation that worsens despite of 48 h treatment.
  Paralysis of any extent of either hindleg.
  Automutilation which is sometimes associated with neuropathic pain models.

Equipment And Reagents. The following materials and substances were used in the study:
  Steel mesh test plane: Ugo Basile, Germany
  Plexiglass test chambers: Ugo Basile, Germany
  Electronic von Frey test hard- and software: Somedic, Sweden.
  MotoRater: TSE Systems, Homburg, Germany
  Gas anesthesia equipment: Harvard Apparatus
  Isoflurane liquid: Attane Vet
  Light Microscope: Zeiss Stereomicroscope, Stemi DV4
  Homeothermic surgery blanket thermostat and probe: Harvard Apparatus
  Silk Suture for the ligatures: 6-0 Ethicon
  Polyamide suture (5-0): Ethicon
  Buprenorphine Temgesic®: Oriola Finland
  0.9% NaCl (Saline): Braun Statistical Analysis. All values are presented as the mean±standard error of the mean. All statistical analyses were conducted with a significance level of $\alpha=0.05$, using GraphPad Prism (Version 8, GraphPad Software, Inc., San Diego, Calif.). Depending on the features of the data, the statistical tests were selected from the following parameters.

Simple comparisons between two groups was performed by either unpaired Student's t-test or, where the assumption of normality was rejected by the D'Agostino-Pearson or Shapiro-Wilk test, by the Mann-Whitney U-test. Welch's t-test was used for pairwise comparisons if data was assumed to be normally distributed, otherwise with unequal variances. For comparisons between two measurements done on the same set of subjects, either paired Student's t-test or Wilcoxon signed-rank test was used as appropriate.

Comparisons involving more than three independent groups was carried out by one-way analysis of variance (ANOVA), or, if data are not normally distributed, by the Kruskal-Wallis test. If group/treatment factor was significant, post hoc multiple comparisons was performed. For comparing all means with all other means, either Tukey or Holm-Šídák test was used. Comparisons to control group mean was done by the Dunnett's test. In case of the Kruskal-Wallis test, post hoc multiple comparisons were done by using the Dunn's test.

For repeated observations on the same group, matched values were analyzed by repeated-measures ANOVA (for normally distributed data) or the Friedman test (for groups where the assumption of normality was rejected). Comparisons between two and more groups done at different points was analyzed by two-way repeated measures ANOVA with group/treatment as "between" factor and time as "within" factor. Main effects of group and time was initially determined and in case of their significant interaction, relevant post hoc multiple comparisons were performed.

Results

No Significant Difference In Body Weight Of Various Groups Of Snl-Rats Throughout The Study. There was no statistical significance observed when comparing different treatment groups to vehicle treated animals.

Figure 5:
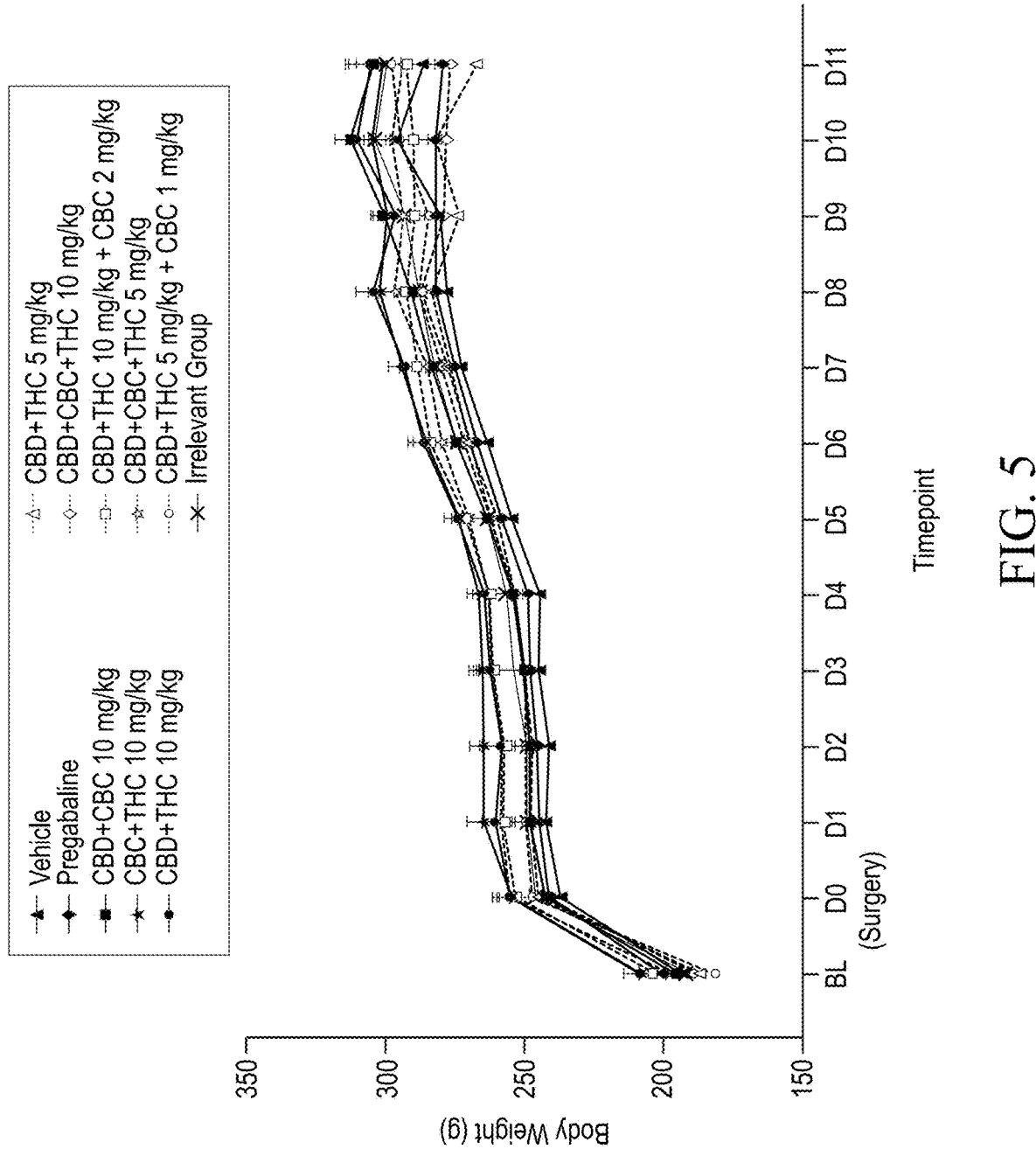
FIG. 5 depicts body weight changes over time illustrative of the effects of distinct doses of 1-3 cannabinoids on the body weight of SNL operated SD rats.

FIG. 5 shows the effects of distinct doses of 1-3 cannabinoids on the body weight of SNL operated SD rats. Data is presented as Mean+SEM. Group sizes: Vehicle, n=12; Pregabalin, n=12; CBD+CBC 10 mg/kg, n=9; CBC+THC 10 mg/kg, n=9; CBD+THC 10 mg/kg, n=9; CBD+THC 5 mg/kg, n=7; CBD+CBC+THC 5 mg/kg, n=9; CBD+THC 5 mg/kg+CBC 1 mg/kg, n=9; CBC 10 mg/kg, n=9. Two-way ANOVA, Tukey's post hoc.

CBD:THC:CBC at 5:5:5 mg/kg was found to reduce mechanical hypersensitivity due to chronic pain. This was an important finding.

To evaluate mechanical hypersensitivity, this study employed electronic von Frey (evF) 8 days post-surgery, as well as paw withdrawal threshold determined within 24 hours post-dosing in each treatment group. The results were graphed and compared with baseline (time 0).

Figure 6:
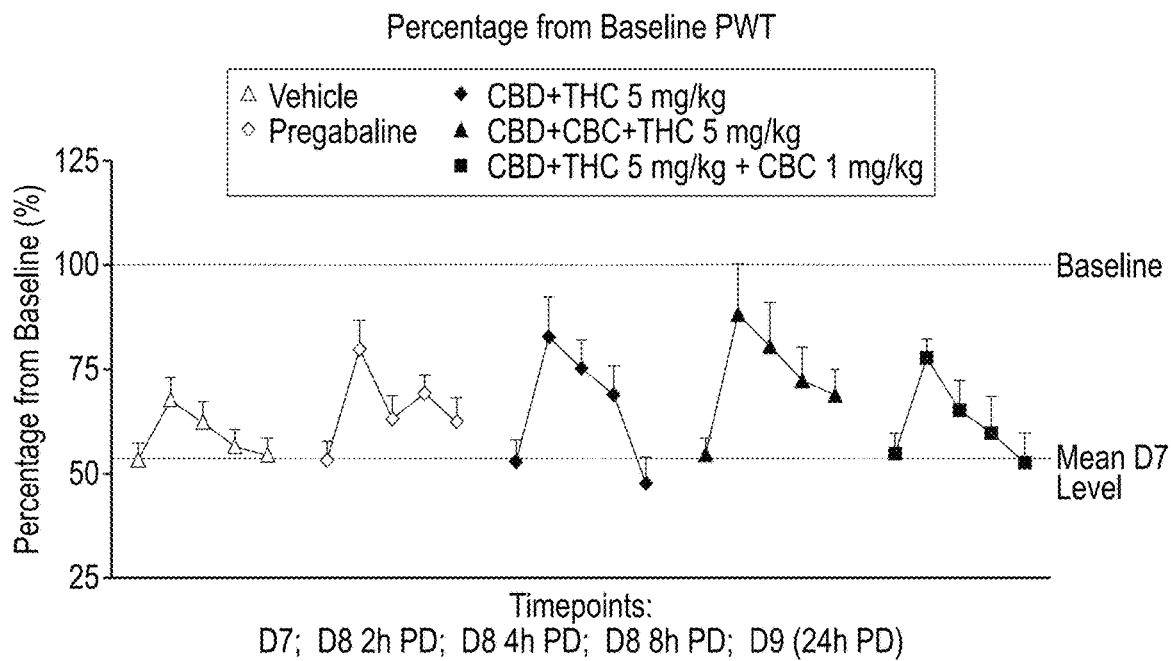
FIG. 6 depicts the effect of different cannabinoid formulations on the intensity of SNL-induced mechanical hypersensitivity in rats using paw withdrawal threshold (PWT).

FIG. 6 shows the effect of cannabinoids on the intensity of SNL-induced mechanical hypersensitivity in rats. The percentage from baseline PWT was evaluated after a variety of timepoints for different treatments. The effect of cannbinoids on the intensity of SNL-induced mechanical hypersensitivity was measured on Day 7 and then 2, 4, 8 and 24 hours after treatment. Data is presented as Mean+SEM for percentage-from-baseline values at the post-SNL timepoints. The curves in the graph were used to analyze the AUCs. The following abbreviations are defined as D7: Day 7; D8: Day 8; D9: Day 9. CBD: Cannabidiol; CBC: Cannabichromene; THC: Δ-9 Tetrahydrocannabinol. AUC: Area Under the Curve. CBD+THC+CBC 5 mg/kg: Treatment with CBD 5 mg/kg and THC 5 mg/kg and CBC 5 mg/kg.

Figure 7:
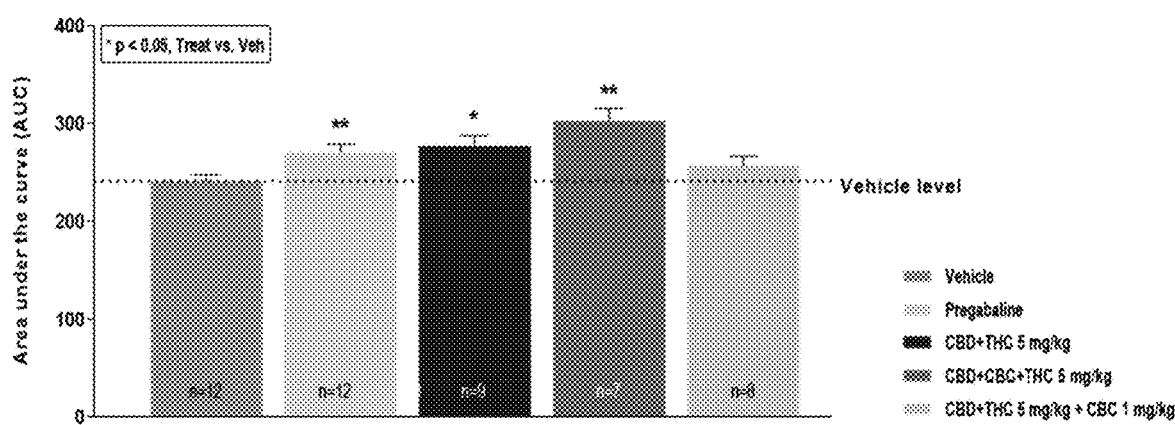
FIG. 7 depicts the Area Under the Curve (AUC) for FIG. 6 in a subset of animals taking 5 mg/Kg of different cannabinoids and statistical significance of treatment groups vs. vehicle for the electronic von Frey test.

FIG. 7 illustrates the area Under the Curve (AUC) representing statistical significance of treatment groups vs. vehicle measure by electronic von Frey test. The effect of cannabinoids on the intensity of SNL-induced mechanical hypersensitivity was measured at 2, 4, 8 and 24 hours and the curves were used to measure the area under the curve; Data is presented as Mean+SEM ant tested with unpaired Welch t-test; *p<0.05, p<0.01, *p<0.001****, p<0.0001.

Treatment of rats with CBD+THC+CBC at 5:5:5 mg/kg significantly reduced SNL-induced mechanical hypersensitivity when compared vehicle group in evF test (p<0.01). Interestingly, treatment with CBD+THC+CBC at 5:5:5 mg/kg caused a significantly higher reduction of mechanical hypersensitivity when compared to Pregabalin positive control (p=0.0186), as evidenced in FIG. 6 and FIG. 7, as well as in the data presented below in Tables 2A & 2B).

TABLE 2A

Multiple/Pairwise Comparison of Treatment Groups in Electronic von Frey Area

| Multiple Comparisons test | Mean Diff | 95% CI | Significance? (Tukey) | Summary (Tukey) | P Value Tukey | Significance? (Fisher LSD) | Summary (Fisher LSD) |
|---|---|---|---|---|---|---|---|
| Pregabalin vs. CBD + THC 5 mg/kg | −6.2 | −43.77 to 31.37 | No | ns | 0.9898 | No | ns |
| Pregabalin vs. CBD + THC + CBC 5:5:5 mg/kg | −31.2 | −67.50 to 5.100 | No | ns | 0.1228 | Yes | * |
| Pregabalin vs. CBD + THC + CBC 5:5:1 mg/kg | 13.8 | −22.50 to 50.10 | No | ns | 0.8157 | No | ns |
| Pregabalin vs. Vehicle | 29.8 | −3,808 to 63.41 | No | ns | 0.1042 | Yes | * |
| CBD + THC 5:5 mg/kg vs. CBD + THC + CBC 5:5:5 mg/kg | −25 | −65.00 to 15.00 | No | ns | 0.3999 | No | ns |
| CBD + THC 5:5 mg/kg vs. CBD + THC + CBC 5:5:1 mg/kg | 20 | −20.00 to 60.00 | No | ns | 0.6179 | No | ns |
| CBD + THC 5 mg/kg vs. Vehicle | 36 | −1,575 to 73.57 | No | ns | 0.0662 | Yes | ** |
| CBD + THC + CBC 5:5:5 mg/kg vs. CBD + THC + CBC 5:5:1 mg/kg | 45 | 6,193 to 83.81 | Yes | * | 0.0157 | Yes | ** |
| CBD + THC + CBC 5:5:5 mg/kg vs. Vehicle | 61 | 24.70 to 97.30 | Yes | *** | 0.0002 | Yes | **** |
| CBD + THC 5 mg/kg + CBC 1 mg/kg vs. Vehicle | 16 | −20.30 to 52.30 | No | ns | 0.721 | No | ns |

| Tukey's multiple comparison test | Mean Diff, | 95% CI | Significant (Tukey) | Summary (Tukey) | P Value Tukey | Significance? (Fisher LSD) | Summary (Fisher LSD) |
|---|---|---|---|---|---|---|---|
| Pregabalin vs. Vehicle | 29.8 | −2,223 to 61.82 | No | Ns | 0.0721 | Yes | * |

TABLE 2B

Multiple/Pairwise Comparison of Treatment Groups in Electronic von Frey Area

| | P Value Fisher LSD) | Mean 1 | Mean 2 | Mean Diff, | SE of diff, | n1 | n2 |
|---|---|---|---|---|---|---|---|
| Multiple Comparisons test | | | | | | | |
| Pregabalin vs. CBD + THC 5 mg/kg | 0.6414 | 271 | 277 | −6 | 13.22 | 12 | 8 |
| Pregabalin vs. CBD + THC + CBC 5:5:5 mg/kg | 0.0186 | 271 | 302 | −31 | 12.78 | 12 | 9 |
| Pregabalin vs. CBD + THC + CBC 5:5:1 mg/kg | 0.2858 | 271 | 257 | 14 | 12.78 | 12 | 9 |
| Pregabalin vs. Vehicle | 0.0154 | 271 | 241 | 30 | 11.83 | 12 | 12 |
| CBD + THC 5:5 mg/kg vs. CBD + THC + CBC 5:5:5 mg/kg | 0.0825 | 277 | 302 | −25 | 14.08 | 8 | 9 |
| CBD + THC 5:5 mg/kg vs. CBD + THC + CBC 5:5:1 mg/kg | 0.1623 | 277 | 257 | 20 | 14.08 | 8 | 9 |
| CBD + THC 5 mg/kg vs. Vehicle | 0.0092 | 277 | 241 | 36 | 13.22 | 8 | 12 |
| CBD + THC + CBC 5:5:5 mg/kg vs. CBD + THC + CBC 5:5:1 mg/kg | 0.0019 | 302 | 257 | 45 | 13.66 | 9 | 9 |

TABLE 2B-continued

Multiple/Pairwise Comparison of Treatment Groups in Electronic von Frey Area

|  | P Value Fisher LSD) | Mean 1 | Mean 2 | Mean Diff, | SE of diff, | n1 | n2 |
|---|---|---|---|---|---|---|---|
| CBD + THC + CBC 5:5:5 mg/kg vs. Vehicle | <0.0001 | 302 | 241 | 61 | 12.78 | 9 | 12 |
| CBD + THC 5 mg/kg + CBC 1 mg/kg vs. Vehicle Tukey's multiple comparison test | 0.2169 | 257 | 241 | 16 | 12.78 | 9 | 12 |
| Pregabalin vs. Vehicle | 0.029 | 271 | 241 | 30 | 12.99 | 12 | 12 |

Analysis of Area under the Curve (AUC) illustrated a marked increase of AUC in rats treated with CBD+THC+CBC at 5:5:5 mg/kg compared to rats treated CBD:THC:CBC at 5:5:1 mg/kg (FIG. 6 and FIG. 7) (p=0.0019). Thus, increasing Cannabichromene from 1 to 5 mg/kg markedly changed mechanical withdrawal thresholds over 24-hour timeframe.

Table 2A and Table 2B shows multiple/pairwise comparison of treatment groups in electronic von Frey Area Under the Curve (AUC). Light Grey background: p<0.05 by Tukey's multiple comparisons; Dark Grey background: p<0.05 by Fisher's LSD for pairwise comparisons. Diff: Difference. CI: Confidence Interval. SE: Standard Error.

Although, treatment of rats with CBD:THC at 5:5 mg/kg ratio was indicated to be effective in reducing the intensity of mechanical hypersensitivity in evF test compared to vehicle (p<0.05), addition of 5 mg/kg Cannabichromene to the compound, seemed to enhance the effect of CBD and THC (p<0.01). To support this notion, CBD+THC+CBC at 5:5:5 mg/kg also showed markedly greater efficacy than pregabalin (p=0.0186), while CBD+THC at 5:5 mg/kg (without CBC) was comparable to pregabalin in reducing mechanical hypersensitivity (p=0.6414) (Tables 2A & 2B). Additional group comparisons at each behavioral test timepoint would shed light on the impact of adding cannabichromene.

Figure 8:
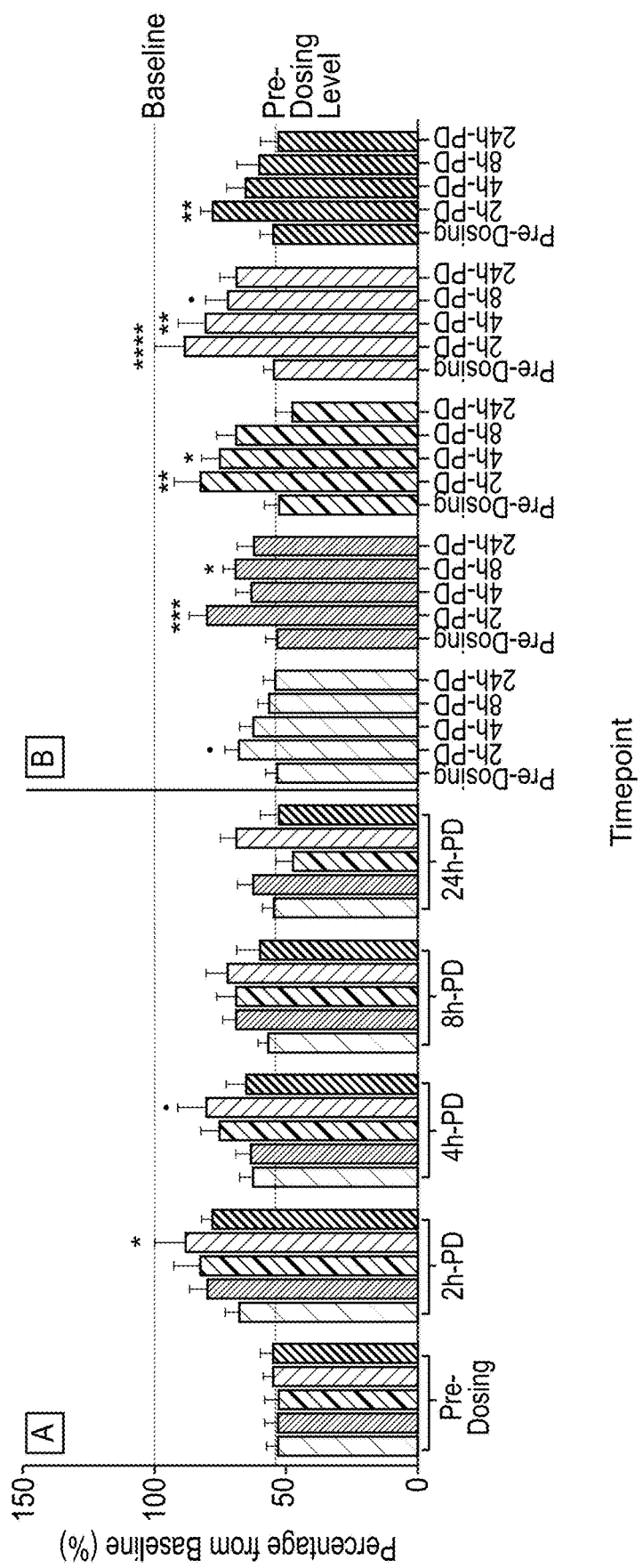
FIG. 8 depicts the effects of multiple distinct doses of cannabinoids on the intensity of SNL-induced mechanical hypersensitivity measured by the evF changes. Panel A compares different treatment groups at a common time period while Panel B shows compares within a treatment group over time.

FIG. 8 shows the effects of multiple distinct doses of cannabinoids on the intensity of SNL-induced mechanical hypersensitivity measured by the evF. Data is presented as percentage from baseline+SEM for each group. (Group sizes: Vehicle, n=12; Pregabalin, n=12; CBD+THC 5 mg/kg, n=8; [CBD+CBC+THC 5 mg/kg], n=9; [CBD+THC 5 mg/kg+CBC 1 mg/kg], n=9). Panel A)•p<0.1; *p<0.05, vs. Vehicle (pairwise post hoc comparisons merely between [CBD+CBC+THC 5 mg/kg] and [CBD+THC 5 mg/kg+CBC 1 mg/kg] vs Vehicle); Panel B)•p<0.1; *p<0.05, p<0.01, *p<0.001, ****p<0.0001, vs. D7 (two-way ANOVA, Dunnett's post hoc).

Group-wise differences were tested to narrow down pairwise post hoc comparison. In order to evaluate the effect of CBD+THC+CBC at 5:5:5 mg/Kg, between-group comparisons (FIG. 8, Panel A) and within-group comparisons were performed (FIG. 8, Panel B).

Between-group-comparisons revealed a significant difference when CBD+THC+CBC 5:5:5 mg/kg treatment was compared to vehicle at 2 hours post-dosing (p=0.0494, two-way ANOVA, Dunnett's post hoc) (FIG. 8, Panel A). This data show that an effect evoked by CBD+THC+CBC 5:5:5 mg/kg indicated by reduction of mechanical hypersensitivity in rats.

In addition, SNL rats treated with CBD+THC+CBC 5:5:5 mg/kg showed 33% increase in Paw Withdrawal Threshold (% PWT) from baseline at 2 hours post-doing (p<0.05). At 4 hours post-dosing, the significance level was not quite reached (p=0.086; two-way ANOVA, Dunnett's post hoc) (FIG. 8, Panel A). This observation might be due to low number of rats (n=9).

Within-group-comparisons conducted by two-way ANOVA, showed a highly significant time-bound effect present, as characterized by a dynamic response to administration, peaking at 2 hours post-dosing and gradually reverting to pre-dosing level.

Significant change from pre-dosing to 2 hours post-dosing was found in all cannabinoid groups in this subset, as well as in Pregabalin group (p<0.05, two-way ANOVA, Dunnett's post hoc) (FIG. 8, Panel B). Evidently, CBD+THC+CBC 5:5:5 mg/kg showed a highly significant difference as compared to pre-dosing level (p<0.0001) (FIG. 8, Panel B). At 4 hours post-doing, CBD+THC 5:5 mg/kg and CBD+THC+CBC 5:5:5 mg/kg were still on significantly higher level than upon pre-dosing (p<0.05 and p<0.01, respectively, two-way ANOVA, Dunnett's post hoc)(FIG. 8, Panel B). A slight rising trend, yet non-significant, was also visible in the vehicle group since the test occasionally produces non-significant but visible changes mostly due to the sensitivity of the test combined to variation in animals' surroundings.

Based upon eVF assay results, increasing CBC from 1 mg/kg to 5 mg/kg, seem to prolong the effect of CBD+THC. It is noteworthy that at 24 hours post-dosing, the result value of the group with highest CBC concentration was still above the pre-dosing level. The difference from pre-dosing level at this timepoint however remains non-significant. Furthermore, what is worth noticing here, is the shape of the dynamic response to administration peaking at 2 hours post dosing and gradually reverting back, close to SNL injury level. The response intensity change with time is clearly different in high CBC dose group, compared to low CBC dose groups.

The effect of adding cannabichromene to CBD and THC was also evaluated SNL rats treated with CBD:THC 10:10 mg/Kg subset and the results are reported in below.

Overall, results from electronic von Frey test confirm the efficacy of CBD:THC:CBC at 5:5:5 mg/kg ratio in reducing SNL-induced mechanical hypersensitivity and indicate the efficacy of this formulation for chronic pain management. Further evaluation of chronic pain and motor control via kinematic gait analysis below explains the enhanced efficacy of CBD+THC when combined with CBC.

Cannabichromene Prolongs the Effect of CBD and Δ⁹-THC and Markedly Improves the Overall Locomotor Activity in Animal Models of Neuropathic Pain.

Comprehensive kinematic analysis was performed by high sensitivity MotoRater that allows detection of any subtle to severe gait changes in SNL model. Three-dimensional observation and analyses were performed from ventral, lateral left and right to assess movements based on trajectories of join positions and angles with respective properties, such as velocity and acceleration. An overall score was reported based on distance from baseline for each treatment group compared to vehicle or within each treatment group. The fine motor capabilities and the gait of the animals were evaluated at the baseline and four times after the SNL surgery, 2 h, 5 h, 9 h and 24 hours post-dosing using the kinematic movement analysis of altogether 97 separate parameters that were recorded.

Figure 9:
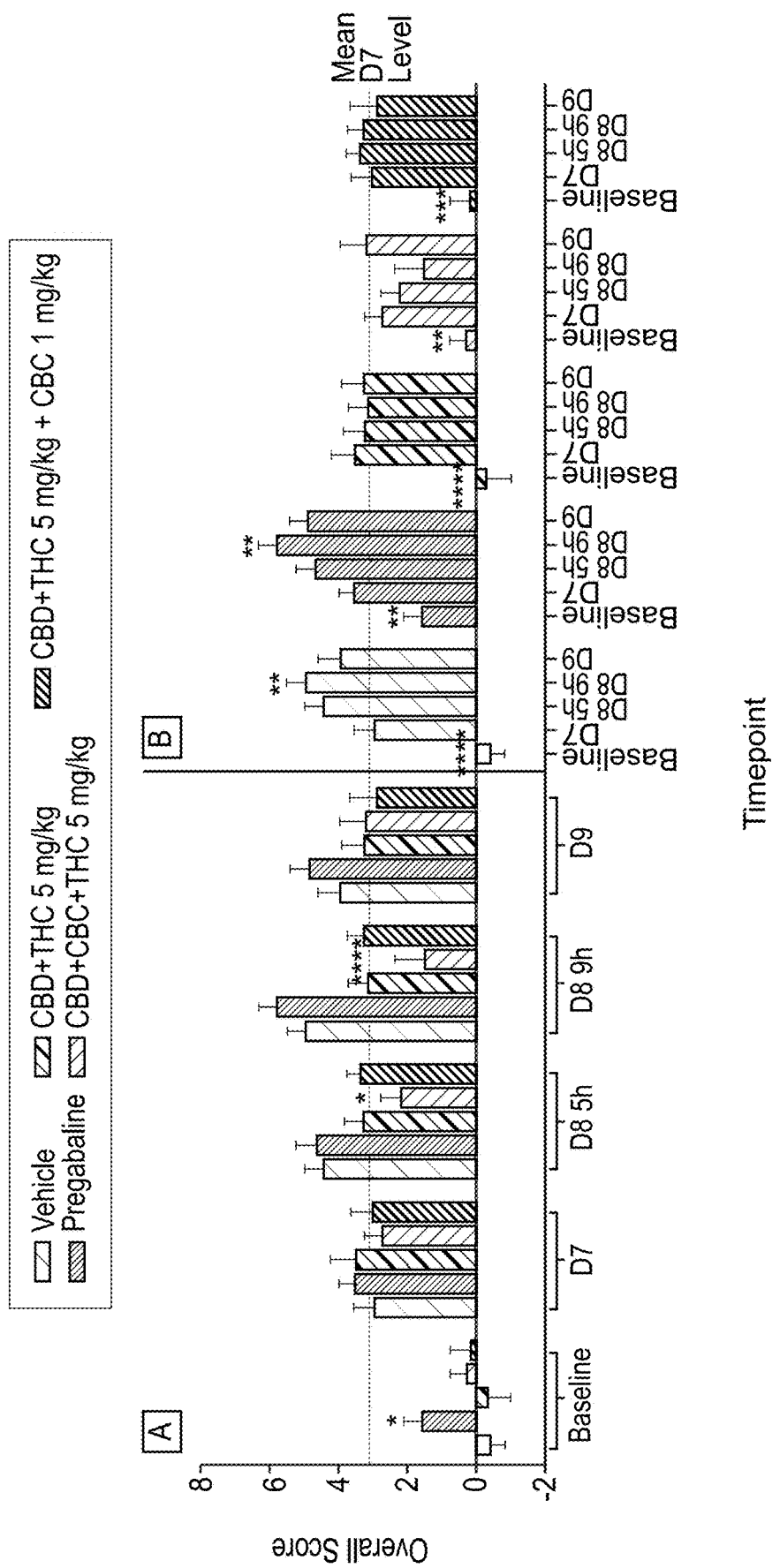
FIG. 9 depicts gait overall score at day 7 to day 9 after treatment in SNL rates. Panel A compares different treatment groups at a common time period while Panel B shows compares within a treatment group over time.

FIG. 9 shows gait overall score at Day 7 to Day 9 after treatment in SNL rats. Two-way Mixed ANOVA: Fixed effects (type Ill): Time $p<0.0001$, Group $p=0.0003$; Time× Group $p=0.0064$; Panel A. Statistically significant difference vs. Vehicle; Dunnett's test (5 families, 4 comparisons per family). Panel B. Within-group comparisons to D7; Dunnett's test (5 families, 4 comparisons per family).

Figure 10A:
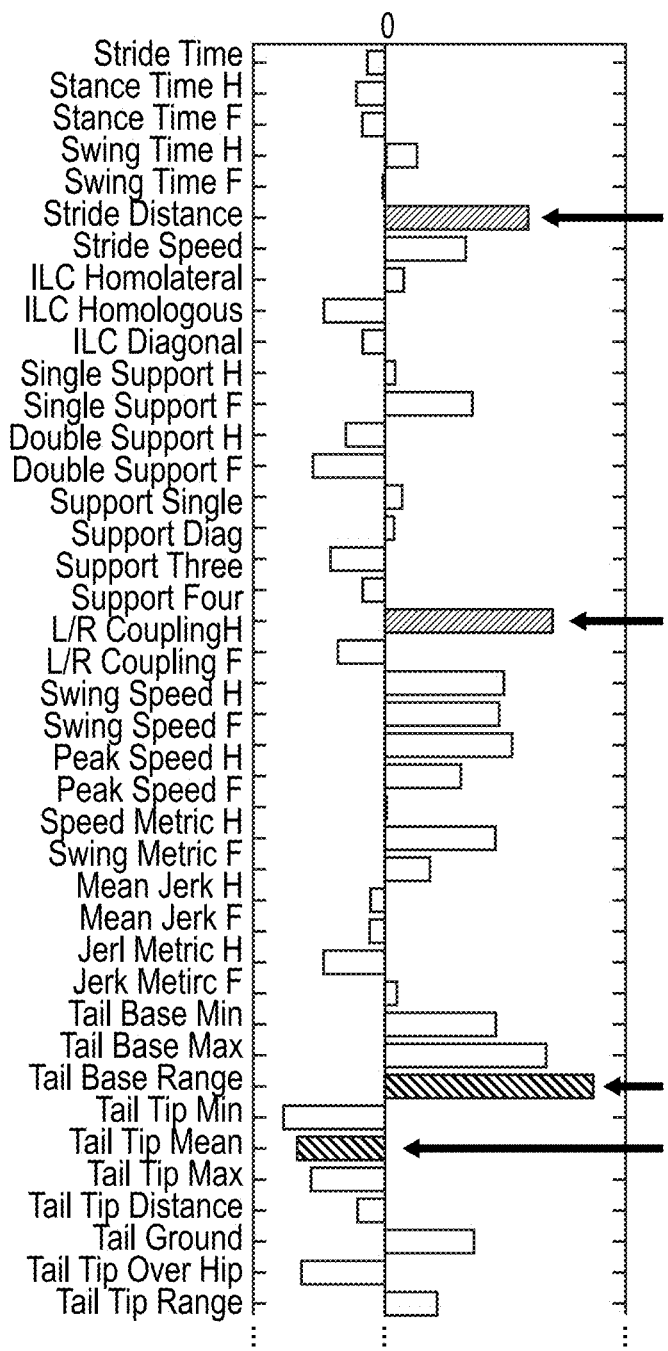
FIG. 10A depicts a discriminant vector bar graph presenting SNL induced motor phenotype, based on Principle component analysis (PCA) of baseline (BL) and D7 differences in all study groups.
Figure 10A:
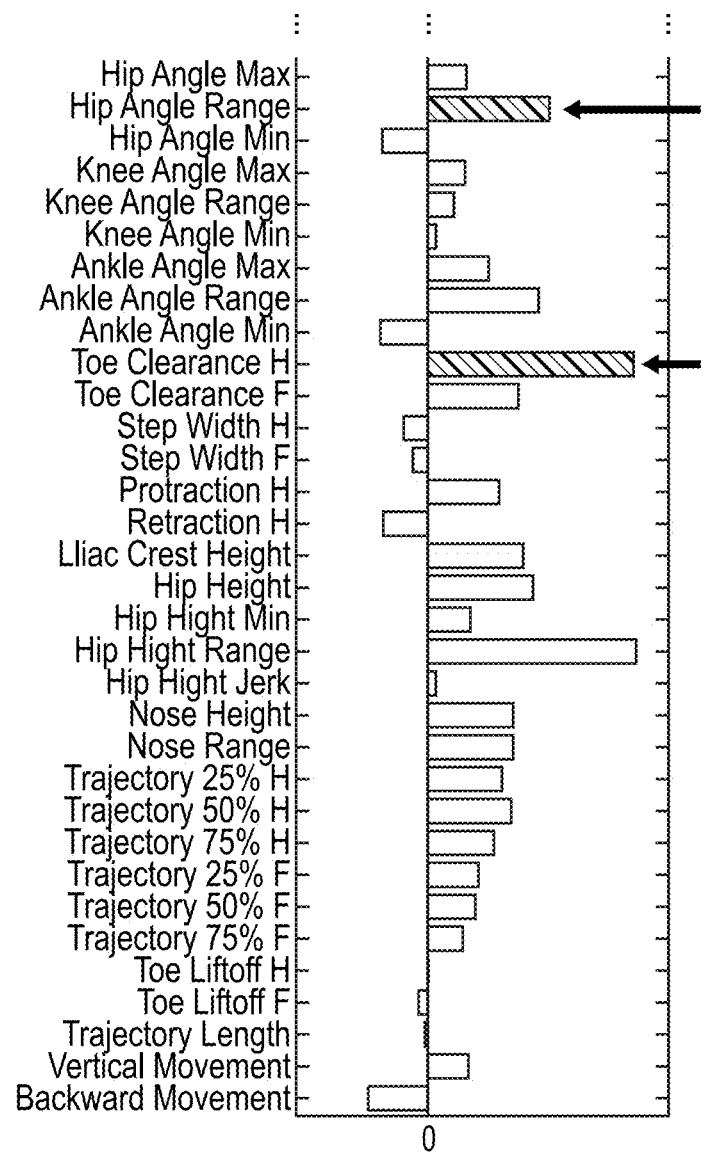

FIG. 10A shows a discriminant vector bar graph presenting SNL induced motor phenotype, based on PCA of BL and D7 differences in all study groups. The original vector graph emphasizes with arrows and differently shaded bars those characteristic gait features, that represent the SNL motor phenotype the most, as highlighted by arrows.

Statistical significances of the adjusted p-values: *$p<0.05$; $p<0.01$, *$p<0.001$, ****$p<0.0001$.

Principal component analysis (PCA) was performed for the parameter data to reduce the number of variables, and to reveal correlations between separate parameters. PCA combines all the parameter data, reveals correlations between them, and provides an overall view of the fine motor and gait characteristics of the SNL-operated rats. Baseline BL and D7 differences in all study groups was presented in the bar graph (FIG. 10A) to illustrate which parameters changed after SNL (zero=BL). The bar length and direction indicate the weight that each parameter is contributed in the overall score. The motor phenotype of SNL model can be characterized and interpreted as the following combination of changes in the gait features (FIG. 10A):

The overall speed is increased which is mainly due to longer stride distance (increased step length).

The interlimb coordination is not dramatically changed, except the asymmetry in the hind limb left-right alternation rhythm is increased (L/R Coupling H)

The overall hip height and vertical range of hip movement are increased (Tail Base mean/max/range, hip height, hip height range, iliac crest height)

Tail tip position is lower (Tail tip min/mean/max)

Hip angle range is increased

Hind limb toe clearance is increased.

This study reports SNL-induced motor phenotype based on PCA and present overall gait score based on between groups and within group comparisons for rats treated with CBD:THC 5:5 mg/kg with 0-5 mg cannabichromene. The groups were compared to vehicle (negative control) and pregabalin (positive control). Further motor phenotype assessment of SNL rats treated with CBD:THC 10:10 mg/kg subset are reported below.

One striking difference between CBD:THC:CBC at 5:5:5 mg/kg ratio treatment and other cannabinoid or Pregabalin treatment groups was a highly improved gait overall score at 5 hours and 9 hours post-dosing ($p<0.05$ and $p<0.0001$, respectively, two-way ANOVA, Dunnett's post hoc) (FIG. 9, Panel A). This finding provides strong evidence for two functional contributions of Cannabichromene.

As displayed in FIG. 9, Panel A, CBD:THC 5:5 mg/kg did not improve gait overall score in rats as compared to vehicle. While, adding Cannabichromene to CBD and Δ9-THC at 1:1:1 ratio markedly augmented the effect of CBD and THC and potently reversed tactile up to 9 hours post-treatment. Notably, these findings indicate that tactile allodynia still existed in all other groups treated with cannabinoids. Therefore, the enhanced mobility and reversing tactile allodynia in SNL rats treated with CBD:THC:CBC 5:5:5 mg/kg is because of addition of CBC and not due to masking psychoactive effect of Δ9-THC. Addition of Cannabichromene to CBD and THC, effectively improved the overall mobility of SNL rats that proves the efficacy of CBD:THC:CBC at 5:5:5 mg/kg ratio in neuropathic pain management.

Another major finding of fine motor kinematic analysis was a markedly significant time-bound effect displayed in the overall gait score of rats treated with CBD:THC:CBC at 5:5:5 mg/kg. These data showed a response to administration in all cannabinoid groups; the score either was decreased close to the baseline, or showed a ceased increase, in contrast to vehicle and pregabalin groups, which continued displaying growing overall score, referring here to moving away from the baseline score (FIG. 9, Panel B). Evidently, at 2 h and 4 h post-dosing, animals treated with CBD+THC+CBC 5:5:5 mg/kg showed an improved gait performance and reversion of tactile compared to pre-dosing test (FIG. 9, Panel B). Increasing the number of rats may improve statistical analysis and test results.

Thus, herein is provided evidence that treatment with CBD:THC:CBC 5:5:5 mg/kg proved to be the most potent compound in reversing tactile over the period of 24 h post-dosing. This formulation effectively reduced mobility impairment in rats up to 9 hours post-dosing ($p<0.0001$). This long-term effect was not observed in SNL-rats treated with Pregabalin or other cannabinoid groups.

Altogether, this study provides a comprehensive behavioral phenotypic assessment of the impact of cannabinoid treatments on chronic neuropathic pain. CBD:THC:CBC at ratio of 5:5:5 mg/kg or 1:1:1 ratio displayed a robust reduction in mechanical hypersensitivity, as well as, a strong reversion of allodynia and a highly improved kinematic performance of SNL-induced neuropathic pain model over 9 hours after a single treatment.

This finding indicate that that adding proper dosage of Cannabichromene to cannabidiol and Δ9-THC may markedly reduce the daily dose in pain patients and also decrease the total intake of CBD and Δ9-THC as painkillers by patients.

Figure 10B:
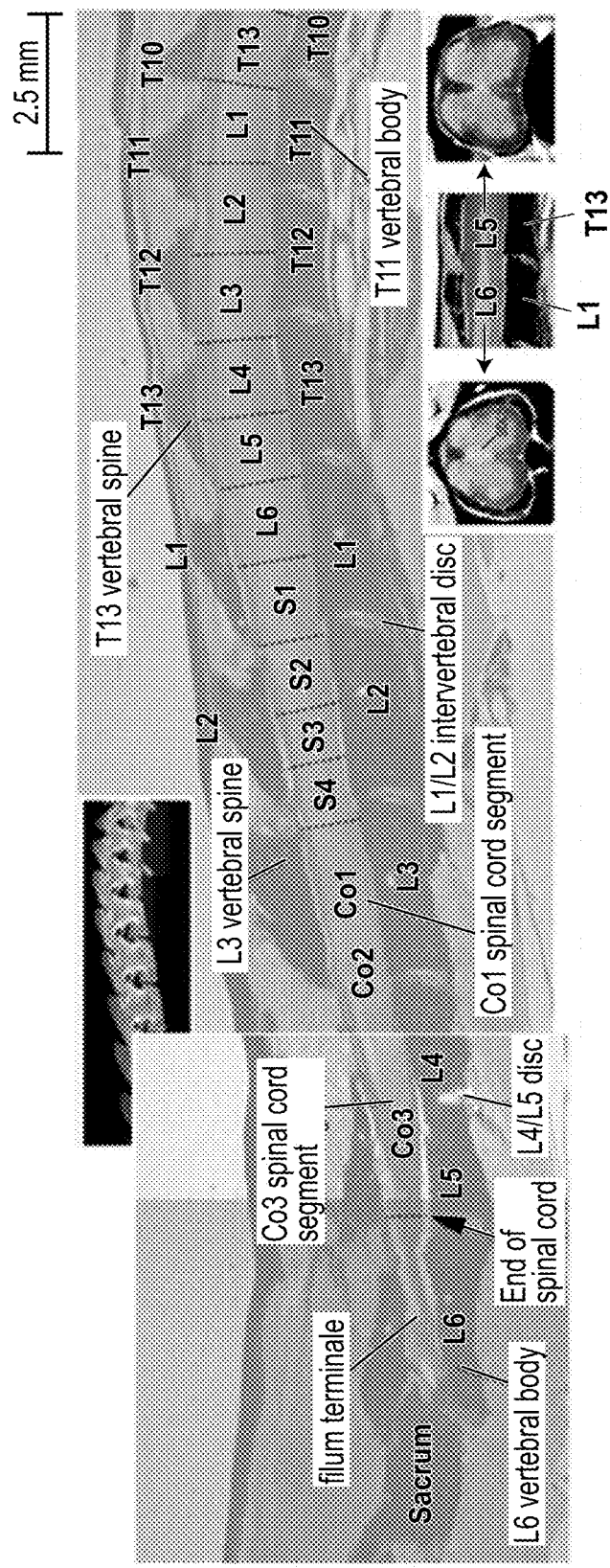
FIG. 10B is an anatomical illustration of the spinal nerve ligation site.

FIG. 10B shows an anatomical illustration of spinal nerve ligation site.

Figure 10C:
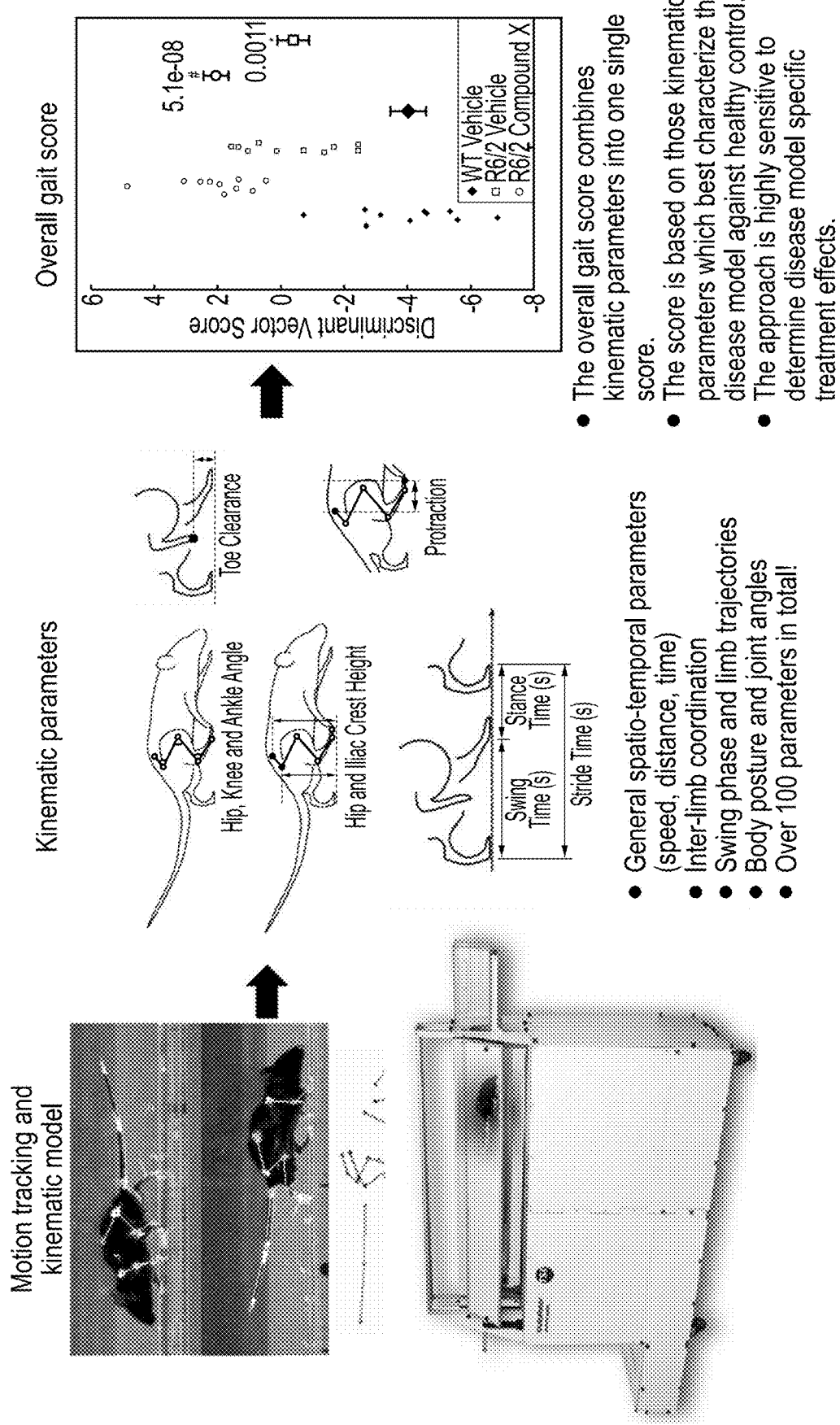
FIG. 10C depicts a flow chart of the fine motor kinematic gait analysis protocol and parameters.

FIG. 10C shows a schematic representation of fine motor kinematic gait analysis. The motion tracking and kinematic model is evaluated for kinematic parameters so as to determine general spatio-temporal parameters (speed, distance, time); Inter-limb coordination; swing phase and limb trajectories; body posture and joint angles, and over 100 parameters in total.

An overall gait score is determined, which combines kinematic parameters into one single score. The score is based on those kinematic parameters which best characterize the disease model against healthy control. This approach is highly sensitive to determine disease model specific treatment effects.

Figure 11:
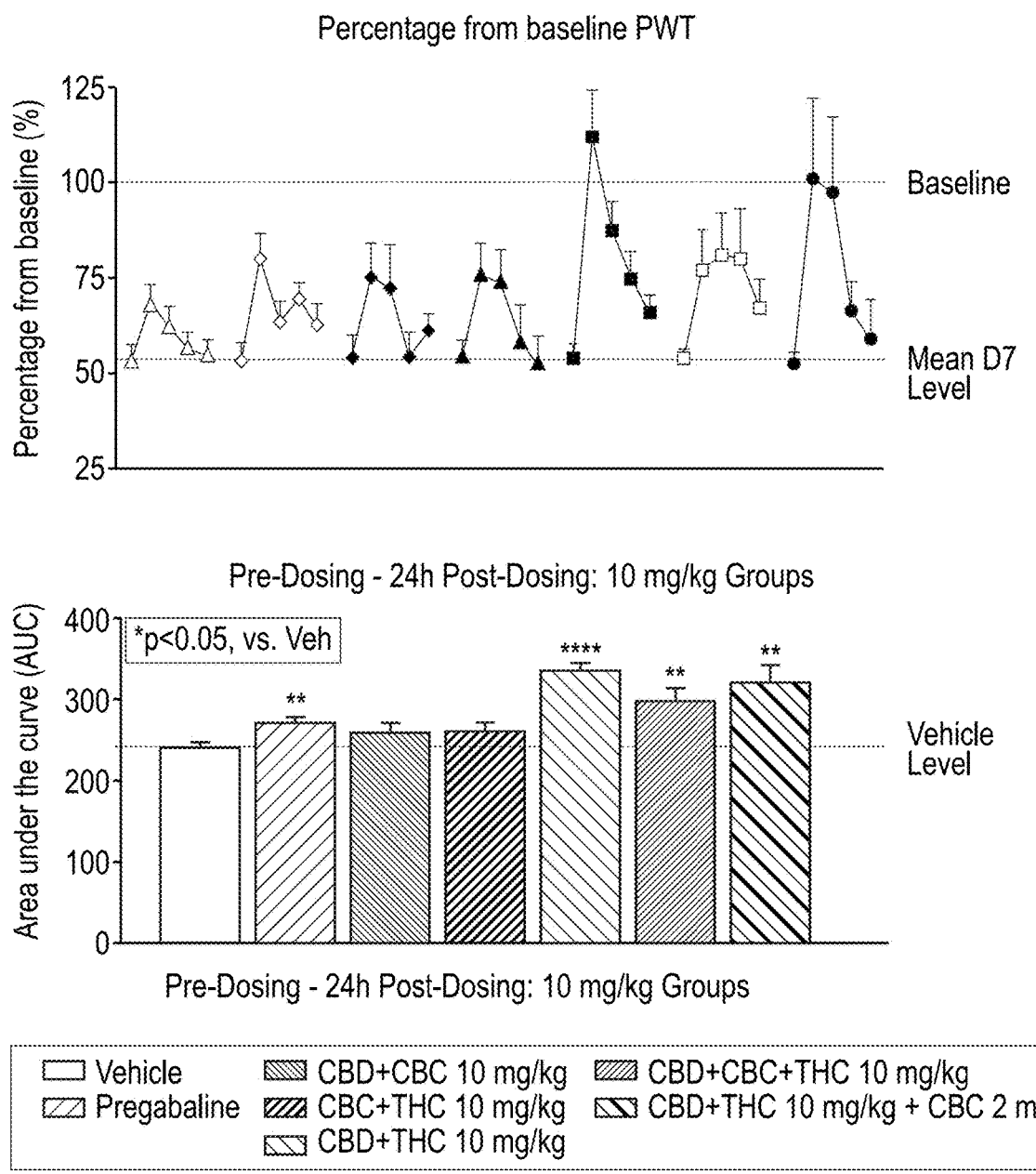
FIG. 11 depicts (upper panel) curves of percentage change from baseline in Paw Withdrawal Threshold (% PWT) over time for different treatment groups versus vehicle for the following curve time points: pre-dosing, 2 h, 4 h, 8 h, and 24 h post-dosing; and (lower panel) Area under the curve (AUC) for a subset of animals taking 10 mg/kg of different cannabinoid formulations.

Results of CBD: THC at 10:10 mg/kg. CBD: THC 10:10 mg/kg—Subset Comparisons. In this subset, the most potent compound in reversing tactile over the period of 24 h post-dosing, was [CBD+THC 10:10 mg/kg]. However, both [CBD+THC+CBC 10:10:10 mg/kg] and [CBD+THC 10 mg/kg+CBC 2 mg/kg or 10:2:10 mg/kg] also displayed highly significant increase of the AUC, compared to the vehicle (FIG. 11, lower panel). Curve points: Pre-dosing 2 h, 4 h, 8 h, and 24 h post-dosing (FIG. 11, upper panel).

FIG. 11 (lower panel) shows AUC for the group subset with 10 mg/kg THC. Data is presented as percentage from baseline PWT+SEM for each group (upper panel), and as AUC for the corresponding curves. (Group sizes [CBD+THC 10 mg/kg], n=9; [CBD+CBC+THC 10 mg/kg], n=9; [CBD+THC 10 mg/kg+CBC 2 mg/kg], n=7). The statistical significances are: $*p<0.05$, $p<0.01$, $*p<0.001$, $****p<0.0001$, vs. Vehicle (Welch's unpaired t-test).

Figure 12:
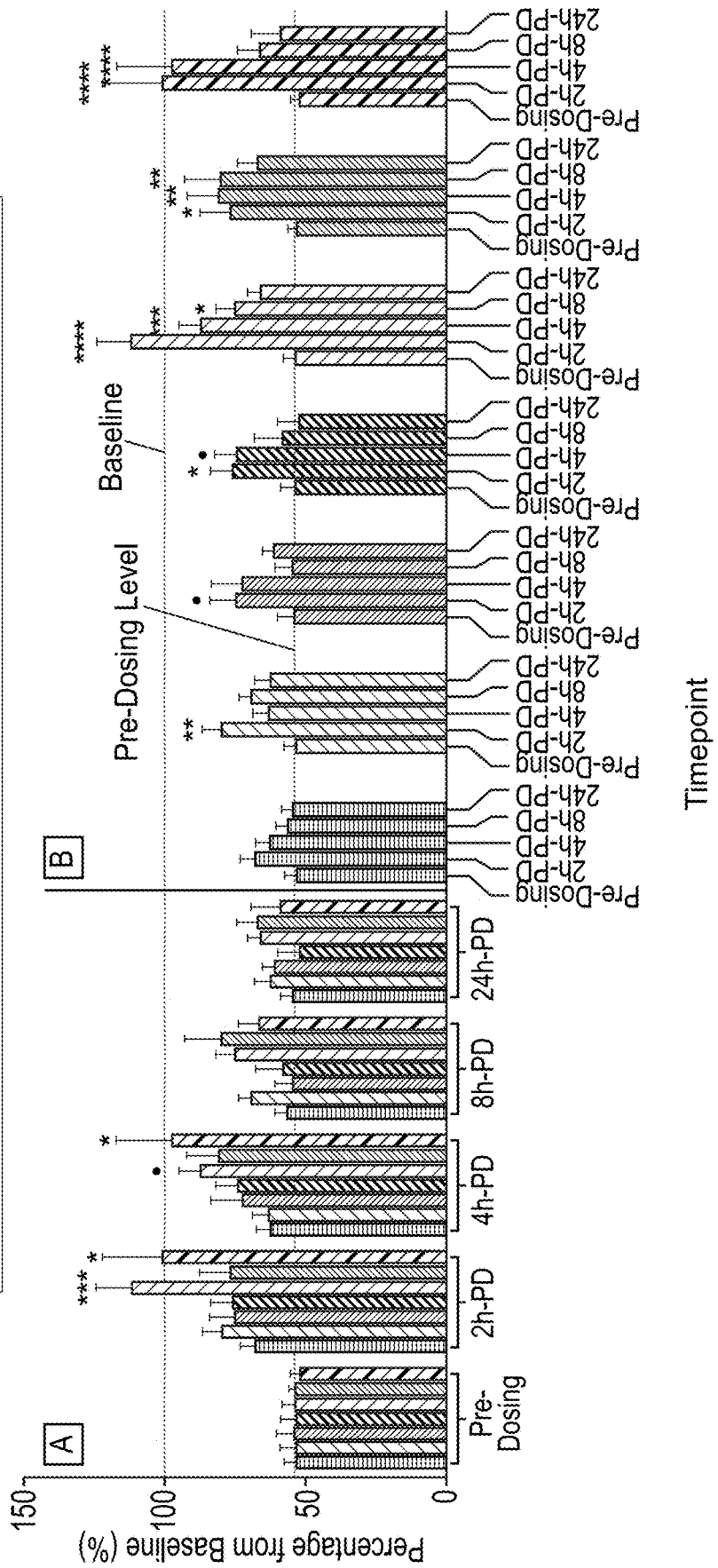
FIG. 12 depicts the effects of multiple distinct doses of cannabinoids on the intensity of SNL-induced mechanical hypersensitivity measured by the evF. Panel A depicts a comparison of different treatments at each time point; Panel B depicts comparisons within a treatment group over time.

FIG. 12 shows the effects of multiple distinct doses of cannabinoids on the intensity of SNL-induced mechanical hypersensitivity measured by the evF. Data is presented as percentage from baseline+SEM for each group. (Group sizes: Vehicle, n=12; Pregabalin, n=12; [CBD+THC 10 mg/kg], n=9; [CBC+THC 10 mg/kg], n=9; [CBD+THC 10 mg/kg], n=9; [CBD+CBC+THC 10 mg/kg], n=9; [CBD+THC 10 mg/kg+CBC 2 mg/kg], n=7). Statistical significances: A) $*p<0.05$, $p<0.01$, $*p<0.001$, $****p<0.0001$, vs. Vehicle; B) $*p<0.05$, $p<0.01$, $*p<0.001$, $****p<0.0001$, vs. D7 (two-way ANOVA, Dunnett's post hoc).

To compare different cannabinoid combinations sharing the dosage of 10 mg/kg THC, a subset of groups were formed and comparisons performed and presented accordingly (FIG. 12).

In this subset, a similar effect was seen as with the formerly presented 5 mg/kg THC-subset. However, with these dose-mixtures, the conducted two-way ANOVA produced highly significant treatment-time interaction effect, based on the pre-selected groups. To further examine these differences, appropriate pairwise post hoc comparisons between Vehicle and both [CBD+THC 10:10 mg/kg] and [CBD+THC 10:10 mg/kg+CBC 2 mg/kg] were performed. Both these groups displayed a significant difference to the Vehicle group at 2 h post-dosing. While the result of [CBD+THC 10:10 mg/kg+CBC 2 mg/kg] at 4 h post-dosing was still significantly higher than Vehicle result, the [CBD+THC 10:10 mg/kg] at this timepoint remained lower, showing a slight trend ($p<0.1$) towards significantly reversed hypersensitivity compared to Vehicle two-way ANOVA, Dunnett's post hoc (FIG. 12).

Within group comparison, displayed a highly significant time-bound effect of the sensitivity level with the 10 mg/kg of THC Subset, showing a similar dynamic response to administration, earlier seen in the 5 mg/kg THC Subset, peaking at 2 hours post-dosing, gradually reverting back to pre-dosing level thereafter. Perceivable statistical significance from pre-dosing to 2 h post-dosing was found in all cannabinoid groups in this subset, as well as in Pregabalin group ($p<0.05$, two-way ANOVA, Dunnett's post hoc) (FIG. 12). Significant or near significant differences to pre-dosing level were also found at 4 h post-dosing for [CBC+THC 10:10 mg/kg], [CBD+THC 10:10 mg/kg], [CBD+THC+CBC 10:10:10 mg/kg] and [CBD+THC 10 mg/kg+CBC 2 mg/kg or 10:10:2 mg/kg]. Even at 8 hours post-dosing, the reversed hypersensitivity was still significant with [CBD+THC 10:10 mg/kg and [CBD+THC+CBC 10:10:10 mg/kg] ($p<0.05$, two-way ANOVA, Dunnett's post hoc) (FIG. 12).

The slight rising trend, found near-significant in the 5 mg/kg THC Subset comparisons, was found non-significant with the 10 mg/kg THC Subset ($p=0.1588$, two-way ANOVA, Dunnett's post hoc) (FIG. 12).

It is noteworthy that the difference between these analyses is merely presenting the nature of statistical modelling, where the confidence intervals and p-values accordingly are based on the overall variance found in all groups included in the analysis, resulting in slight changes in the final p-values, depending on the combination of groups included in the analysis.

Figure 13:
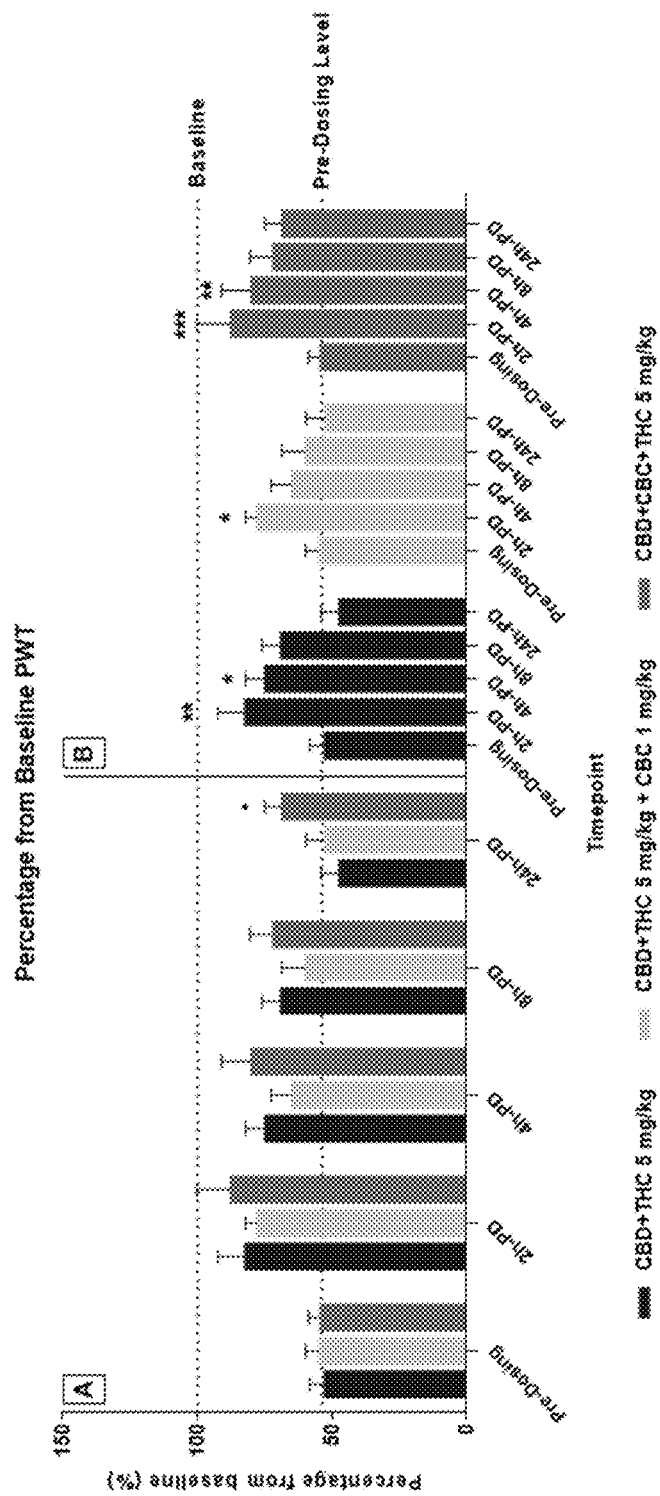
FIG. 13 depicts the effects of multiple distinct doses of cannabinoid formulations, on mechanical hypersensitivity using evF, compared over time. Panel A depicts a comparison between treatment groups, whereas Panel B depicts a comparison within a treatment group over time.
Figure 14:
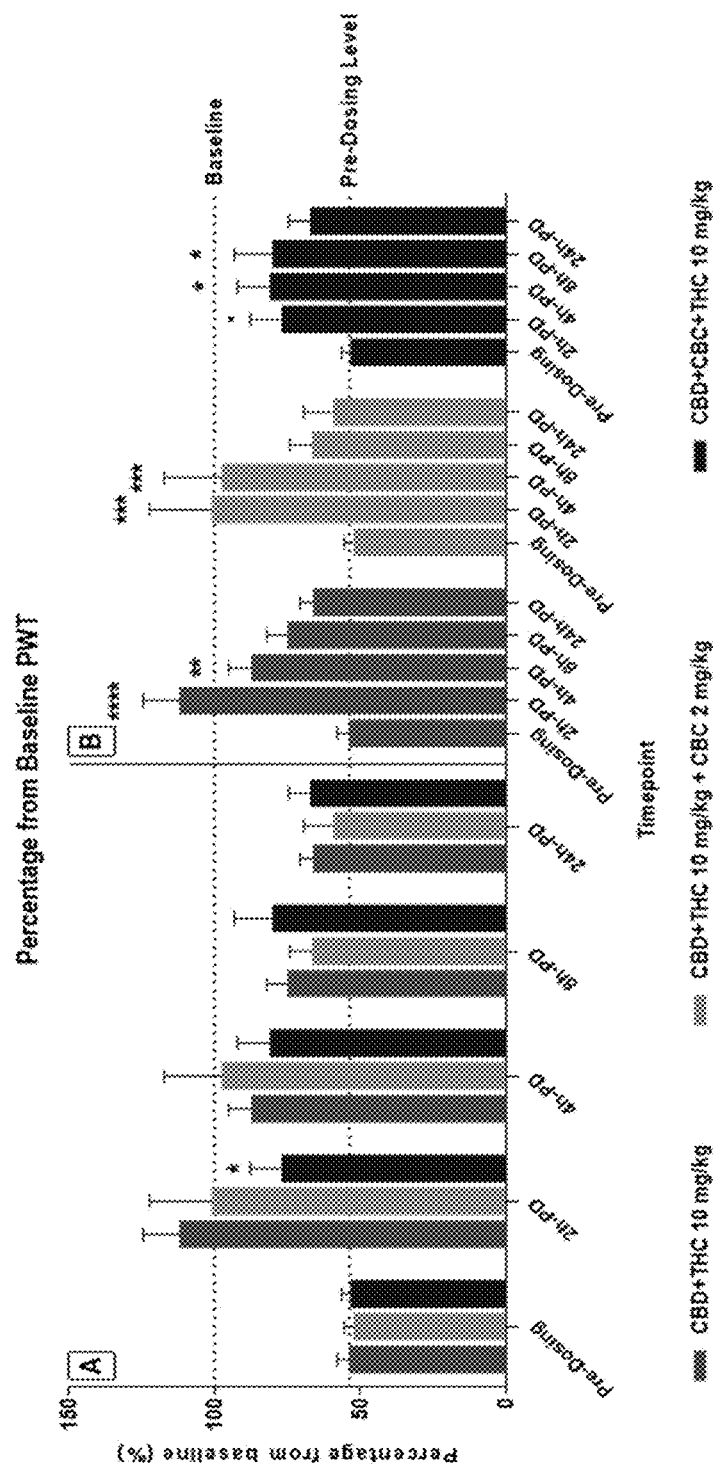
FIG. 14 depicts the effects of multiple distinct doses of cannabinoids on the intensity of SNL-induced mechanical hypersensitivity measured by the evF.

The Effect of Increasing CBC Dose. To examine the effect of increasing CBC dosage, the following subset of groups were formed. CBD+THC 5 mg/kg, CBD+THC 5:5 mg/kg+CBC 1 mg/kg and CBD+THC+CBC 5:5:5 mg/kg (FIG. 13). CBD+THC:10 mg/kg, CBD+THC+CBC 10:10:2 mg/kg and CBD+THC+CBC 10:10:10 mg/kg (FIG. 14).

FIG. 13 illustrates the effects of multiple distinct doses of cannabinoids on the intensity of SNL-induced mechanical hypersensitivity measured by the evF. Data is presented as percentage from baseline+SEM for each group. (Group sizes: [CBD+THC 5 mg/kg], n=8; [CBD+THC 5 mg/kg+CBC 1 mg/kg], n=9; [CBD+THC+CBC 5 mg/kg], n=9). Statistical significances: Panel A) $*p<0.05$, $p<0.01$, $*p<0.001$, $****p<0.0001$, vs. Vehicle; Panel B) $*p<0.05$, $p<0.01$, $*p<0.001$, $****p<0.0001$, vs. D7 (two-way ANOVA, Dunnett's post hoc).

In the first subset (5 mg/kg THC-groups), increased CBC dose appears to show marginally improved reversion of hypersensitivity, when compared to the groups with 0 or 1 mg/kg CBC. Still, no significant treatment effect, or treatment-time interaction effect was present in this subset of groups ($p>0.05$, two-way ANOVA) (FIG. 13). However, with pairwise post hoc comparisons against the group with no CBC, i.e. [CBD+THC 5:5 mg/kg], at 24 h PD there is an "established trend towards significant difference" ($p<0.1$) between [CBD+CBC 5 mg/kg] and [CBD+THC+CBC 5:5:5 mg/kg] ($p=0.0904$, two-way ANOVA, Dunnett's post hoc) (FIG. 13).

Further, highly significant time-bound effect was found in this subset as well. Statistically significant difference between the pre-dosing and 2 h post-dosing value was found in all groups in this subset ($p<0.05$, two-way ANOVA, Dunnett's post hoc) (FIG. 13). Significant differences to pre-dosing level were also found at 4 h PD for [CBD+THC 5:5 mg/kg] and [CBD+THC+CBC 5:5:5 mg/kg] groups ($p<0.05$, two-way ANOVA, Dunnett's post hoc) (FIG. 13).

It is worth noting that at 24 h PD, the result value of the group with highest CBC concentration still is above the Pre-dosing level. The difference from Pre-dosing level at this timepoint however remains non-significant.

FIG. 14 shows the effects of multiple distinct doses of cannabinoids on the intensity of SNL-induced mechanical hypersensitivity measured by the evF. Data is presented as percentage from baseline+SEM for each group. (Group sizes [CBD+THC 10 mg/kg], n=9; [CBD+THC+CBC 10 mg/kg], n=9; [CBD+THC 10 mg/kg+CBC 2 mg/kg], n=7). Statistical significances: Panel A) $*p<0.05$, $p<0.01$, $*p<0.001$, $****p<0.0001$, vs. Vehicle. Panel B) $*p<0.05$, $p<0.01$, $*p<0.001$, $****p<0.0001$, vs. D7 (two-way ANOVA, Dunnett's post hoc).

The comparisons between the second subset of groups: [CBD+THC 10:10 mg/kg], [CBD+THC+CBC 10:10:2 mg/kg], [CBD+THC+CBC 10:10:10 mg/kg] show differences in FIG. 14.

With 10 mg/kg THC, increasing CBC dose appeared to cause marginal reduction of the reversing effectivity of THC+CBD. However, no significant treatment effect or treatment-time interaction was displayed between this subset of groups (p>0.05, two-way ANOVA) (FIG. 14). Yet, by pairwise post hoc comparisons against the [CBD+THC 10:10 mg/kg], at 2 h PD, significantly lower result (=higher hypersensitivity/allodynia) was revealed in [CBD+THC+CBC 10:10:10 mg/kg] (p<0.0264, two-way ANOVA, Dunnett's post hoc) (FIG. 14).

Again, highly significant time-bound effect was shown within this subset of groups. A statistical significance was found in all groups. In this subset displayed significant or near statistical significant allodynia reversion (higher value) at 2 h post-dosing, (p<0.05, two-way ANOVA, Dunnett's post hoc) (FIG. 14). Significant differences to pre-dosing value were further found in all groups at 4 h post-dosing, and in [CBD+THC+CBC 10:10:10 mg/kg] at 8 h post-dosing (p<0.05, two-way ANOVA, Dunnett's post hoc) (FIG. 14).

As with the previous subsets, so with this subset, it is worth noting that at 24 hours post-dosing, the result value of the group with highest CBC concentration still is above the pre-dosing level. The difference from pre-dosing level at this timepoint however remains non-significant.

What is worth noticing here, is the shape of that dynamic response to administration peaking at 2 hours post dosing and gradually reverting back, close to SNL injury level. The response intensity change with time is clearly different in high CBC dose group, compared to low CBC dose groups. Although a similar 2 hours post-dosing peak as seen with the other groups is lacking from [CBD+THC+CBC 10:10:10 mg/kg], a gradual increase (less hypersensitive) is shown through the timepoints of 4 h and 8 h. At 24 hours post-dosing, the level still remains above the pre-dosing value (non-significant difference).

The overall gait scores reflect all of those changes, that were found on PCA analysis, together (using the discriminant direction vector as a "yardstick"), and are presented in a way that the average score at baseline is equal to zero. The average score of all study groups at D7 is equal to 3.107 (z-scores. The decrease of the overall score means that the gait performance has changed towards to the pre-SNL status (BL).

Below, the overall gait scores are presented in subsets as previously described.

CBC Strongly Prolongs the Effect of CBD and THC and Markedly Improved SNL-Induced Mobility Impairment: THC 10 mg/kg—Subset Comparisons. To compare different cannabinoid combinations that share the dosage of THC as 10 mg/kg, the following subset of groups were formed and comparisons performed and presented according to FIG. 15. Vehicle, CBD+THC 10:10 mg/kg, CBD+THC+CBC 10:10:10 mg/kg and CBD+THC+CBC 10:10:2 mg/kg.

Figure 15:
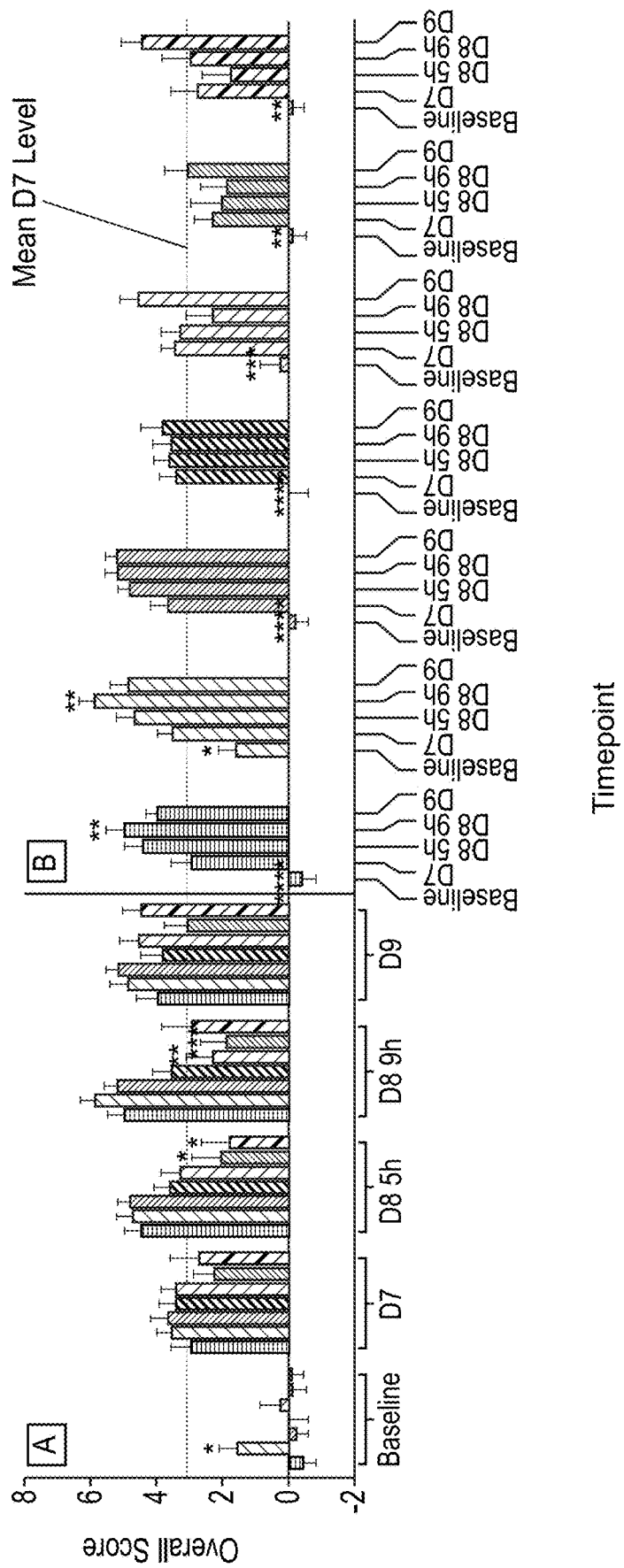
FIG. 15 depicts overall gait scores from animals having SNL. Panel A compares between treatment groups, whereas Panel B compares within a treatment group over time.

FIG. 15 shows overall gait performance (gait overall score) within the THC 10 mg/kg—subset groups. Data is presented as mean score+SEM for each group. Statistical significances: Panel A) *p<0.05, vs. Vehicle; Panel B)•p<0.1; *p<0.05, p<0.01, *p<0.001, ****p<0.0001, vs. D7 (two-way ANOVA, Dunnett's post hoc).

Significant and highly significant treatment effect (towards baseline) were produced within the groups of this subset, when compared to Vehicle group. Further pairwise post hoc comparisons revealed, that at both 5 h and 9 h PD timepoints, both [CBD+THC 10:10 mg/kg] and [CBD+THC+CBC 10:10:10 mg/kg] were competent to yield significant difference to the Vehicle group (p<0.05, two-way ANOVA, Dunnett's post hoc) (FIG. 15, Panel A).

Moreover, highly significant time-bound effect was presented, when comparing the overall gait scores between the timepoints, within each group. Similar to the 5 mg/kg THC subset, in all cannabinoid groups, the score either was decreased close to the baseline, or exhibited a ceased increase. A profoundly different score pattern was displayed by the Vehicle and Pregabalin groups, with increasing score until 9 h PD timepoint, followed by a slight decrease to the 24 h PD timepoint (FIG. 15, Panel B).

Table 3 provides multiple/pairwise comparison of treatment groups in electronic von Frey Area Under the Curve (AUC). Lighter shaded background: p<0.05 by Tukey's multiple comparisons; Darker shaded background: p<0.05 by Fisher's LSD for pairwise comparisons. Diff: Difference. CI: Confidence Interval. SE: Standard Error.

TABLE 3

| Multiple/Pairwise Comparison of Treatment Groups in Electronic von Frey AUC. | | | | | | | | | | | |
|---|---|---|---|---|---|---|---|---|---|---|---|
| Tukey's multiple comparisons test (multiple comparisons) | | | | Uncorrected Fisher's LSD (Pairwise comparisons) | | | | | | | |
| Treatments Compared | Significant? | Summary | P Value | Significant? | Summary | P Value | Mean 1 | Mean 2 | Mean Diff. | n1 | n2 |
| Pregabaline vs. CBD + THC 10 mg/kg | Yes | ** | 0.0032 | Yes | *** | 0.0002 | 270.8 | 334 | −63.2 | 12 | 9 |
| Pregabaline vs. CBD + THC 10 mg/kg + CBC 2 mg/kg | No | ns | 0.0754 | Yes | ** | 0.0054 | 270.8 | 320 | −49.2 | 12 | 7 |
| Pregabaline vs. Vehicle | No | ns | 0.4037 | Yes | * | 0.0462 | 270.8 | 241 | 29.8 | 12 | 12 |
| CBD + CBC 10 mg/kg vs. CBC + THC 10 mg/kg | No | ns | >0.9999 | No | ns | 0.953 | 260 | 261 | −1 | 9 | 9 |
| CBD + CBC 10 mg/kg vs. CBD + THC 10 mg/kg | Yes | *** | 0.0009 | Yes | **** | <0.0001 | 260 | 334 | −74 | 9 | 9 |
| CBD + CBC 10 mg/kg vs. CBD + CBC + THC 10 mg/kg | No | ns | 0.2863 | Yes | * | 0.0282 | 260 | 298 | −38 | 9 | 9 |
| CBD + CBC 10 mg/kg vs. CBD + THC 10 mg/kg + CBC 2 mg/kg | Yes | * | 0.0243 | Yes | ** | 0.0015 | 260 | 320 | −60 | 9 | 7 |
| CBD + CBC 10 mg/kg vs. Vehicle | No | ns | 0.8908 | No | ns | 0.2342 | 260 | 241 | 19 | 9 | 12 |
| CBC + THC 10 mg/kg vs. CBD + THC 10 mg/kg | Yes | ** | 0.0011 | Yes | **** | <0.0001 | 261 | 334 | −73 | 9 | 9 |

TABLE 3-continued

Multiple/Pairwise Comparison of Treatment Groups in Electronic von Frey AUC.

| Treatments Compared | Tukey's multiple comparisons test (multiple comparisons) | | | Uncorrected Fisher's LSD (Pairwise comparisons) | | | | | | | |
|---|---|---|---|---|---|---|---|---|---|---|---|
| | Significant? | Summary | P Value | Significant? | Summary | P Value | Mean 1 | Mean 2 | Mean Diff. | n1 | n2 |
| CBC + THC 10 mg/kg vs. CBD + CBC + THC 10 mg/kg | No | ns | 0.3168 | Yes | * | 0.0325 | 261 | 298 | −37 | 9 | 9 |
| CBC + THC 10 mg/kg vs. CBD + THC 10 mg/kg + CBC 2 mg/kg | Yes | * | 0.0283 | Yes | ** | 0.0018 | 261 | 320 | −59 | 9 | 7 |
| CBC + THC 10 mg/kg vs. Vehicle | No | ns | 0.8649 | No | ns | 0.2108 | 261 | 241 | 20 | 9 | 12 |
| CBD + THC 10 mg/kg vs. CBD + CBC + THC 10 mg/kg | No | ns | 0.3491 | Yes | * | 0.0373 | 334 | 298 | 36 | 9 | 9 |
| CBD + THC 10 mg/kg vs. CBD + THC 10 mg/kg + CBC 2 mg/kg | No | ns | 0.9865 | No | ns | 0.4415 | 334 | 320 | 14 | 9 | 7 |
| CBD + THC 10 mg/kg vs. Vehicle | Yes | **** | <0.0001 | Yes | **** | <0.0001 | 334 | 241 | 93 | 9 | 12 |
| CBD + CBC + THC 10 mg/kg vs. CBD + THC 10 mg/kg + CBC 2 mg/kg | No | ns | 0.8846 | No | ns | 0.2282 | 298 | 320 | −22 | 9 | 7 |
| CBD + CBC + THC 10 mg/kg vs. Vehicle | Yes | * | 0.0108 | Yes | *** | 0.0006 | 298 | 241 | 57 | 9 | 12 |
| CBD + THC 10 mg/kg + CBC 2 mg/kg vs. Vehicle | Yes | *** | 0.0004 | Yes | **** | <0.0001 | 320 | 241 | 79 | 7 | 12 |

These data show an improvement in pain management/pain relief parameters for formulations in which CBD, CBC and THC are all present versus formulations without CBC.

Formulations containing CBD, CBC, and THC in equal quantities were tested against formulations with only CBD and THC, or against vehicle to evaluate kinematic parameters. These data underscores the benefit of having CBC as the third primary cannabinoid in the formulation.

Figure 16:
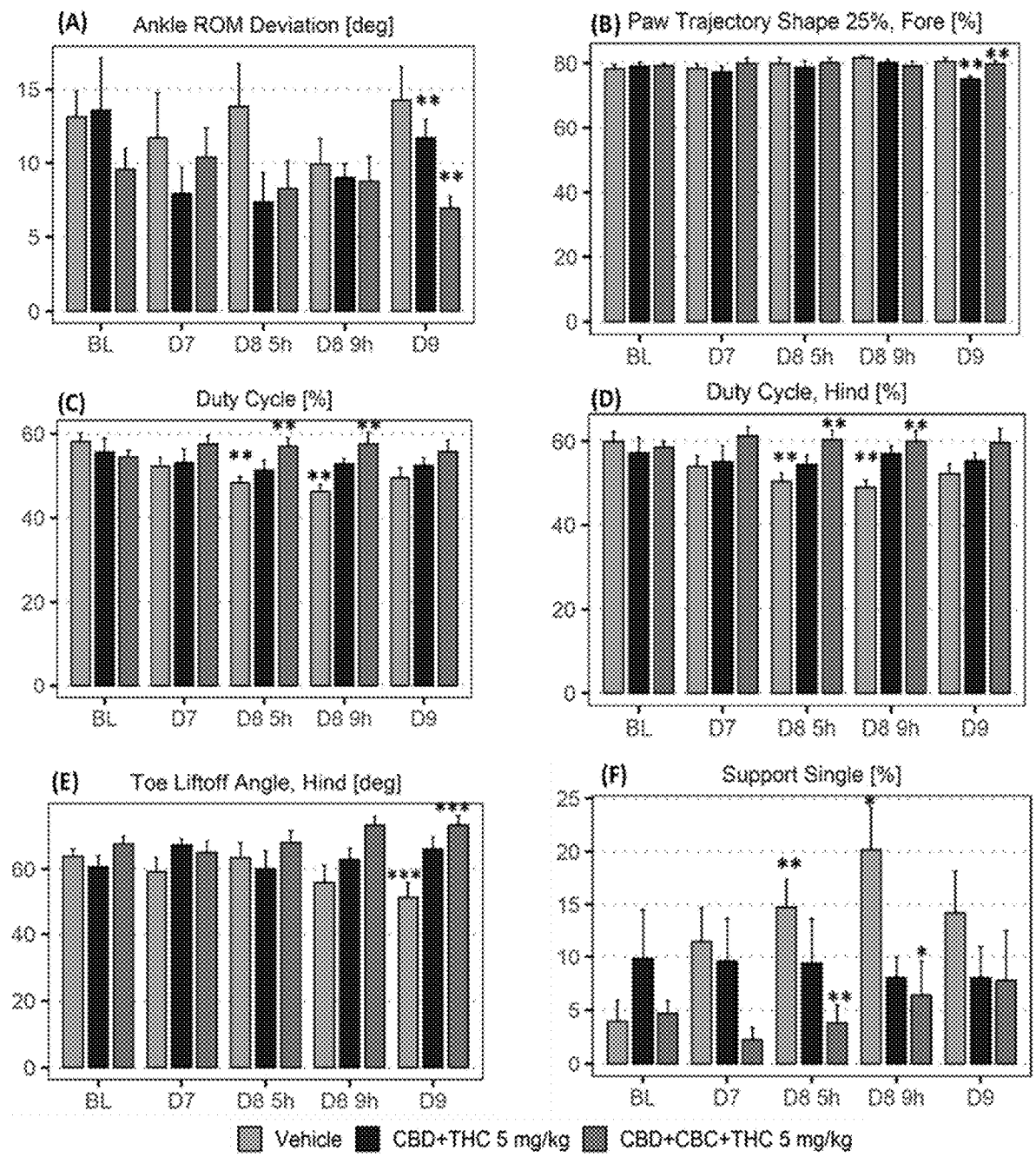
FIG. 16 shows kinematic gait parameter representatives illustrate the impact of adding CBC to CBD+THC at baseline, D7, D8-5 h, D8-9 h and D9 post-dosing.

FIG. 16 shows kinematic gait parameter representatives, which illustrate the beneficial impact of adding CBC to CBD+THC in the formulation. Data are shown at Baseline, D7, D8-5 h, D8-9 h and D9 Post-Dosing. Statistical significances: 0.01 was considered significant based on adjusted p-values.

Panel A—Ankle Range of Motion (ROM)—D9 PD: CBD+THC+CBC (5:5:5 mg/kg) vs. CBD+THC (5:5 mg/Kg): p=0.009. Panel B-Percentage Paw Trajectory Shape (Forelimb)—D9: CBD+THC+CBC (5:5:5 mg/kg) vs. CBD+THC (5:5 mg/Kg): p=0.003. Panel C—Overall % Duty Cycle—D8-5 h AND D8-9 h: CBD+THC+CBC (5:5:5 mg/kg) vs. Vehicle: p=0.003 and p=0.004. Panel D—% Hindlimb Duty Cycle—D8-5 h AND D8-9 h: CBD+THC+CBC (5:5:5 mg/kg) vs. Vehicle: p=0.005 and p=0.003, respectively. Panel E—Toe Liftoff Angle Hindlimb [degree]—D9 PD: CBD+THC+CBC (5:5:5 mg/kg) vs. Vehicle: p=0.000598. Panel F—Support Single: D8-5 h AND D8-9 h: CBD+THC+CBC (5:5:5 mg/kg) vs. Vehicle: p=0.003 and *p=0.014, respectively. N1/N2: Group sizes.

Table 4A and Table 4B show multiple/pairwise comparisons of particular kinematic gait parameters compared pre- and post-dosing. Only significant effects (p≤0.01) are shown, and Adj. sig (Adjusted Significance)=*p<0.05; p<0.01; *p<0.001.

TABLE 4A

Multiple/Pairwise Comparison of Particular Kinematic Gait Parameters Compared Pre- and Post-Dosing

| Timeline | Variable | group1 | group2 | Dose group2 | n1 | n2 |
|---|---|---|---|---|---|---|
| D9 | Toe Liftoff Angle, Hind [degree] | Vehicle | CBD + CBC + THC | 5 mg/kg | 12 | 7 |
| D8 9 h | Mean Speed [cm/s] | Vehicle | CBD + CBC + THC | 5 mg/kg | 12 | 8 |
| D9 | Paw Trajectory Shape 25% Forelimb [%] | CBD + THC 5 mg/kg | CBD + CBC + THC | 5 mg/kg | 8 | 7 |
| D8 5 h | Duty Cycle [%] | Vehicle | CBD + CBC + THC | 5 mg/kg | 12 | 8 |
| D8 9 h | Duty Cycle, Hind [%] | Vehicle | CBD + CBC + THC | 5 mg/kg | 12 | 8 |
| D8 5 h | Support Single [%] | Vehicle | CBD + CBC + THC | 5 mg/kg | 12 | 8 |
| D8 5 h | Retraction, Hind [m] | Vehicle | CBD + CBC + THC | 5 mg/kg | 12 | 8 |
| D8 9 h | Mean Swing Speed, Forelimb [m/s] | Vehicle | CBD + CBC + THC | 5 mg/kg | 12 | 8 |
| D8 9 h | Peak Swing Speed, Forelimb [m/s] | Vehicle | CBD + CBC + THC | 5 mg/kg | 12 | 8 |
| D8 9 h | Duty Cycle [%] | Vehicle | CBD + CBC + THC | 5 mg/kg | 12 | 8 |
| D8 5 h | Duty Cycle, Hindlimb [%] | Vehicle | CBD + CBC + THC | 5 mg/kg | 12 | 8 |
| D7 | Protraction, Hindlimb [m/s] | Vehicle | CBD + CBC + THC | 5 mg/kg | 12 | 8 |
| BL | Swing Speed Metric Hindlimb | Vehicle | CBD + CBC + THC | 5 mg/kg | 12 | 9 |
| D8 9 h | Support Three [%] | Vehicle | CBD + CBC + THC | 5 mg/kg | 12 | 8 |
| D8 9 h | Peak Swing Speed, Hindlimb [m/s] | Vehicle | CBD + CBC + THC | 5 mg/kg | 12 | 8 |
| D8 9 h | Hip Angle, Min [degree] | Vehicle | CBD + CBC + THC | 5 mg/kg | 12 | 8 |
| D7 | Knee Angle, Min [degree] | Vehicle | CBD + CBC + THC | 5 mg/kg | 12 | 8 |

TABLE 4A-continued

Multiple/Pairwise Comparison of Particular Kinematic Gait Parameters Compared Pre- and Post-Dosing

| Timeline | Variable | group1 | group2 | Dose group2 | n1 | n2 |
|---|---|---|---|---|---|---|
| D8 9 h | Duty Cycle, Forelimb [%] | Vehicle | CBD + CBC + THC | 5 mg/kg | 12 | 8 |
| D8 5 h | Duty Cycle, Forelimb [%] | Vehicle | CBD + CBC + THC | 5 mg/kg | 12 | 8 |
| D8 9 h | Double Support [%] | Vehicle | CBD + CBC + THC | 5 mg/kg | 12 | 8 |
| D8 5 h | Mean Speed [cm/s] | Vehicle | CBD + CBC + THC | 5 mg/kg | 12 | 8 |
| D8 9 h | Protraction, Hind [m] | Vehicle | CBD + CBC + THC | 5 mg/kg | 12 | 8 |
| D9 | Ankle ROM Deviation [degree] | Vehicle | CBD + CBC + THC | 5 mg/kg | 12 | 7 |
| D9 | Ankle ROM Deviation [degree] | CBD + THC 5 mg/kg | CBD + CBC + THC | 5 mg/kg | 8 | 7 |
| D8 9 h | Toe Liftoff Angle, Hind [degree] | Vehicle | CBD + CBC + THC | 5 mg/kg | 12 | 8 |
| D8 9 h | Double Support, Forelimb [%] | Vehicle | CBD + CBC + THC | 5 mg/kg | 12 | 8 |
| D8 9 h | Mean Swing Speed, Hindlimb [m/s] | Vehicle | CBD + CBC + THC | 5 mg/kg | 12 | 8 |
| D8 5 h | Double Support, Hindlimb [%] | Vehicle | CBD + CBC + THC | 5 mg/kg | 12 | 8 |
| D8 9 h | Double Support, Hi | Vehicle | CBD + CBC + THC | 5 mg/kg | 12 | 8 |
| BL | Step Width Deviation | Vehicle | CBD + CBC + THC | 5 mg/kg | 12 | 9 |

TABLE 4B

Multiple/Pairwise Comparison of Particular Kinematic Gait Parameters Compared Pre- and Post-Dosing

| Timeline | Variable | statistic | df | p-value | Adj. P-value | Adj. sig |
|---|---|---|---|---|---|---|
| D9 | Toe Liftoff Angle, Hind [degree] | −4.21 | 16.9 | 0.000598 | 0.000598 | *** |
| D8 9 h | Mean Speed [cm/s] | 3.75 | 11.4 | 0.003 | 0.003 | ** |
| D9 | Paw Trajectory Shape 25% Forelimb [%] | −3.73 | 12.6 | 0.003 | 0.003 | ** |
| D8 5 h | Duty Cycle [%] | −3.56 | 13.5 | 0.003 | 0.003 | ** |
| D8 9 h | Duty Cycle, Hind [%] | −3.66 | 13.1 | 0.003 | 0.003 | ** |
| D8 5 h | Support Single [%] | 3.49 | 17.2 | 0.003 | 0.003 | ** |
| D8 5 h | Retraction, Hind [m] | 3.3 | 18 | 0.004 | 0.004 | ** |
| D8 9 h | Mean Swing Speed, Forelimb [m/s] | 3.59 | 11.5 | 0.004 | 0.004 | ** |
| D8 9 h | Peak Swing Speed, Forelimb [m/s] | 3.46 | 13.1 | 0.004 | 0.004 | ** |
| D8 9 h | Duty Cycle [%] | −3.61 | 12.1 | 0.004 | 0.004 | ** |
| D8 5 h | Duty Cycle, Hindlimb [%] | −3.41 | 16.1 | 0.004 | 0.004 | ** |
| D7 | Protraction, Hindlimb [m/s] | −3.24 | 18 | 0.003 | 0.005 | ** |
| BL | Swing Speed Metric, Hindlimb | −3.2 | 18.9 | 0.005 | 0.005 | ** |
| D8 9 h | Support Three [%] | −3.7 | 9.26 | 0.008 | 0.005 | ** |
| D8 9 h | Peak Swing Speed, Hindlimb [m/s] | 3.37 | 12.2 | 0.006 | 0.006 | ** |
| D8 9 h | Hip Angle, Min [degree] | −3.27 | 13.6 | 0.006 | 0.006 | ** |
| D7 | Knee Angle, Min [degree] | 3.12 | 16.9 | 0.006 | 0.006 | ** |
| D8 9 h | Duty Cycle, Forelimb [%] | −3.27 | 12.3 | 0.007 | 0.007 | ** |
| D8 5 h | Duty Cycle, Forelimb [%] | −3.22 | 10.9 | 0.008 | 0.008 | ** |
| D8 9 h | Double Support [%] | −3.45 | 8.6 | 0.008 | 0.008 | ** |
| D8 5 h | Mean Speed [cm/s] | 2.98 | 16 | 0.009 | 0.009 | ** |
| D8 9 h | Protraction, Hind [m] | 2.95 | 16.2 | 0.009 | 0.009 | ** |
| D9 | Ankle ROM Deviation [degree] | 3.05 | 13.5 | 0.009 | 0.009 | ** |
| D9 | Ankle ROM Deviation [degree] | 3.12 | 11.3 | 0.009 | 0.009 | ** |
| D8 9 h | Toe Liftoff Angle, Hind [degree] | −3 | 15.7 | 0.009 | 0.009 | ** |
| D8 9 h | Double Support, Forelimb [%] | −3.41 | 7.97 | 0.009 | 0.009 | ** |
| D8 9 h | Mean Swing Speed Hindlimb [m/s] | 3.2 | 9.78 | 0.01 | 0.01 | ** |
| D8 5 h | Double Support, Hindlimb [%] | −3.1 | 11.3 | 0.01 | 0.01 | ** |
| D8 9 h | Double Support, Hi | −3.16 | 9.17 | 0.011 | 0.011 | * |
| BL | Step Width Deviation | 2.76 | 17.6 | 0.013 | 0.013 | * |

The data presented in FIG. 16 and Tables 4A & 4B illustrate a significant effect of CBC in extending the effect of CBD+THC when the three primary cannabinoids are present in together in a formulation, as indicated by longer-lasting pain management compared to the CBD+THC mixture (absent CBC). For example, rats treated with CBD+THC+CBC (5:5:5 mg/kg) showed a marked improvement in joint angles and paw trajectory up to 24 hours PD (FIG. 16, Panels A, B, E). Furthermore, treatment with CBD+THC+CBC (5:5:5 mg/kg) displayed a significant enhancement in duration of paw contact to surface (% duty cycle) up to 9 hours PD, while CBD+THC in the absence of CBC did not show the prolonged effect compared to vehicle. Treatment of SNL rats with CBD+THC+CBC (5:5:5 mg/kg) substantially improved interlimb coordination as indicated by % support single (FIG. 16, Panel F) up to 9 hours post-dosing compared to vehicle, whereas, CBD+THC did not improve interlimb coordination and pain management as effectively.

Example 5

Formulation for Pain Management: Effects on Human TRPA1 Channel Expressed in Mammalian Cells
Summary
Formulations for pain management were tested for effects on the human TRPA1 channel, expressed in mammalian cells using the ScreenPatch® assay (IonWorks™ Barracuda Based Assay): agonist mode. The data presented confirming a synergistic effect of cannabinoids (CBD:THC:CBC) at the ion channel level.

Material and Methods

Test Articles. The test articles, also referenced herein as test formulations, were evaluated in an 8-point concentration-response format (4 replicate wells/concentration, Table 4A & Table 4B). The test articles were dissolved and initially serially diluted in dimethyl sulfoxide (DMSO). The final dilution was made in extracellular solution. The final DMSO concentration was 0.6% (v/v).

Positive Control Treatment Groups. Stock solutions of positive control articles were prepared in batches, aliquoted for individual use. The positive control test solutions were prepared fresh on the day of experiment. The final DMSO concentration was 0.6% (v/v). In this study, the TRPA1 agonist mustard oil (MO) was used a positive control agonist. Reference antagonist, ruthenium red (0-10 µM), was used for both TRPA1.

Figure 17:
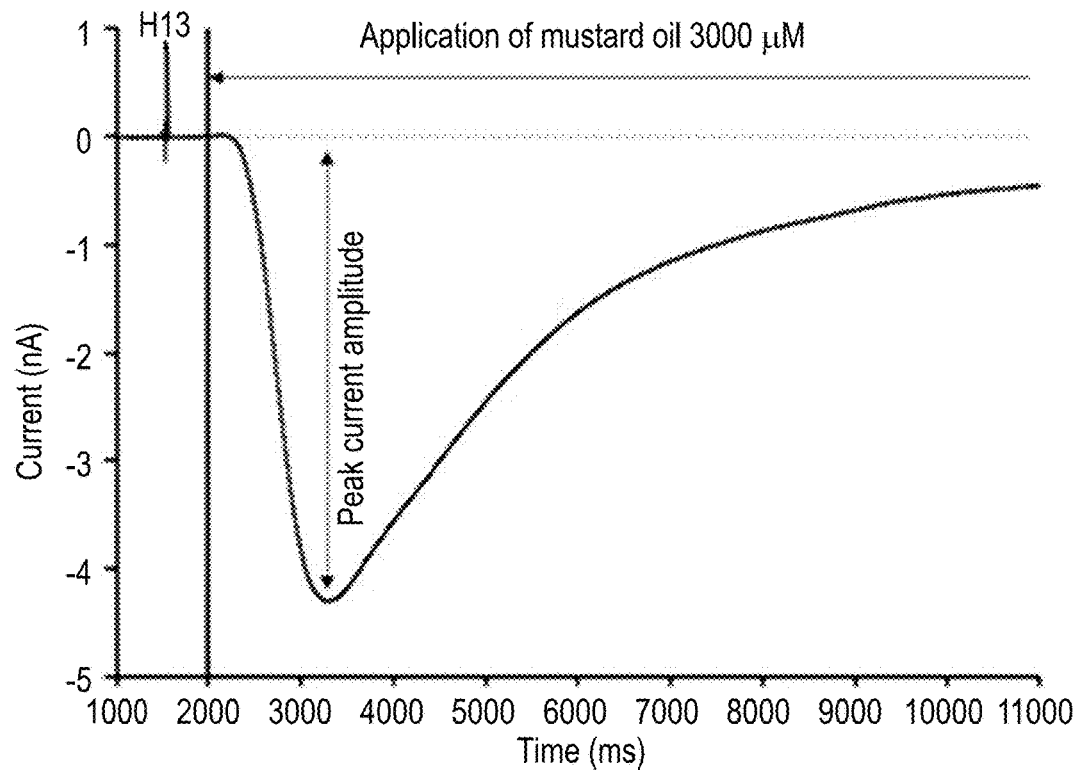
FIG. 17 depicts a representative trace of current produced by application of 3000 µM mustard oil.

Measurements. FIG. 17 shows representative example of currents produced by application of 3000 µM mustard oil and measurements of maximum currents at the peak current amplitude.

FIG. 17 shows a representative trace of current produced by application of 3000 µM of mustard oil to cells expressing TRPA1 receptors. The vertical line shows start of application. The vertical two headed arrow shows points where measurements were done (~4 nA).

TRPA1 Channels.

Test System: TRPA1 ionotropic receptors expressed in CHO cells.

Test Platform: Ionworks Barracuda™

Electrophysiological Procedures. Intracellular solution (mM): 50 mM CsCl, 90 mM CsF, 2 mM $MgCl_2$, 5 mM EGTA, 10 mM HEPES. Adjusted to pH 7.2 with CsOH. This solution was prepared in batches and stored at room temperature. In preparation for a recording session, the intracellular solution was loaded into the intracellular compartment of the PPC planar electrode.

Extracellular solution, HB-PS (composition in mM): NaCl, 137; KCl, 1.0; $MgCl_2$, 2; $CaCl_2$, 2; HEPES, 10; Glucose, 10; pH adjusted to 7.4 with NaOH (refrigerated until use). Holding potential: −70 mV, potential during agonist/antagonist application: −70 mV.

Recording procedure. Extracellular buffer was loaded into the PPC plate wells (11 µL per well). Cell suspension was pipetted into the wells (9 µL per well) of the PPC planar electrode.

Whole-cell recording configuration was established via patch perforation with membrane currents recorded by on-board patch clamp amplifiers.

Single application (scan) protocol was used.

Test Article Administration. The application consisted of the addition of 20 µL of 2× concentrated test article solution at 10 µL/s (2 second total application time).

TRPA1 Positive Control—Agonist. 0-3000 µM mustard oil (8 concentration dose-response, 4 replicates, half log scale).

Positive Control—Antagonist. 0-10 µM Ruthenium Red (8 concentrations, 4 replicates, half log scale).

Control Articles.

Figure 18:
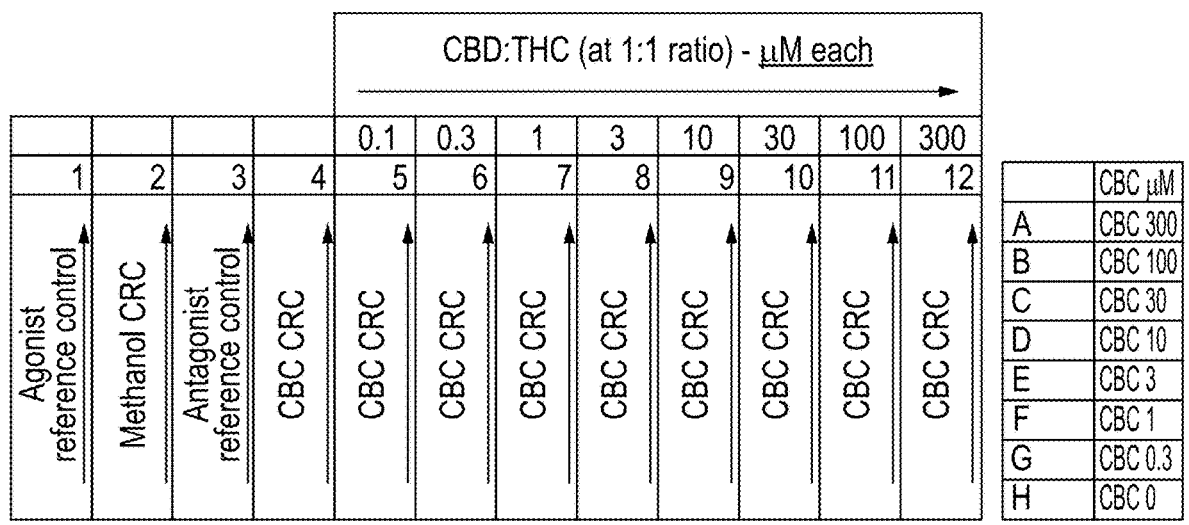
FIG. 18 provides a schematic of certain aspects of ion channel study design.

TRPA1 receptor agonist:
Name: Allyl isothiocyanate (mustard oil)
Source: Sigma-Aldrich
M.W. 99.15
Rationale for Selection: Allyl isothiocyanate is agonist of the TRPA1 receptor TRPA1 receptors antagonist:
Name: Ruthenium Red
Source: Sigma-Aldrich
M.W. 786.35
Rationale for Selection: Ruthenium red is antagonist of the TRPA1 receptor Plates Load Map An exemplary plates load map as used in the study is illustrated in the schematic shown in FIG. 18.

Agonist and antagonist reference control: TRPA1 0-3000 µM mustard oil and Ruthenum Red 0-10 µM, respectively, performed with 1× concentrations.

Results

Agonist properties of cannabichromene (CBC) and mixture of cannabidiol (CBD) and Δ9-THC were examined using an HTS electrophysiology-based approach, Ion Work Barracuda (IWB). A single-application protocol was employed.

Agonist Activity of CBC and CBD+THC Mixture at TRPA1 Receptors.

Reference agonist, mustard oil, produced activation of TRPA1 receptors with $EC_{50}$=479 µM. Non-selective inhibitor, ruthenium red, inhibited TRPA1 receptors with $IC_{50}$=1.79 µM. Both $EC_{50}$ and $IC_{50}$ values were consistent with historical data.

Figure 19A:
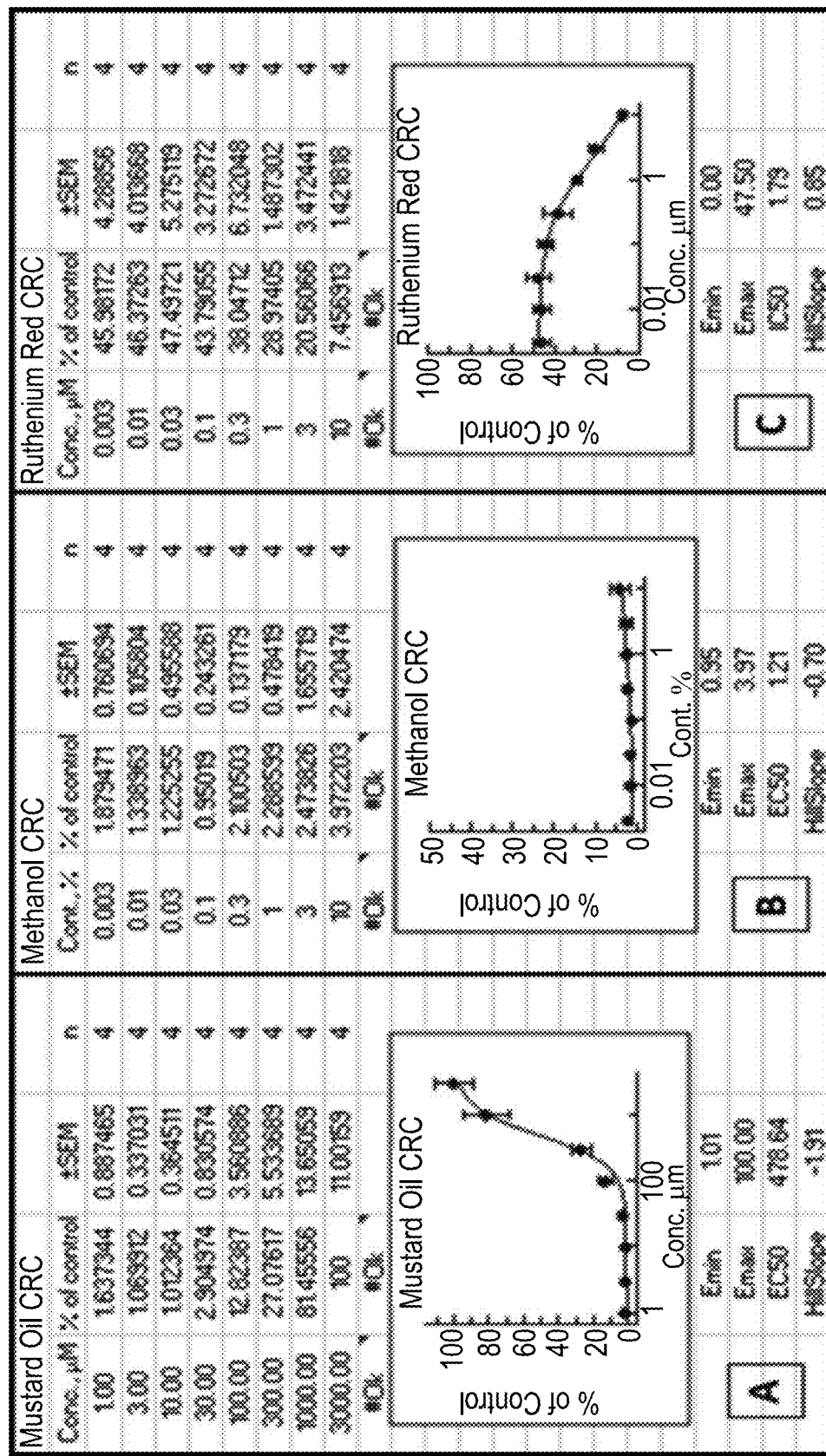
FIG. 19A provides plot representation and numeric information of activity of compounds at TRPA1 receptors showing a CBD+THC concentration response curve of agonist effects in Panels A to F.
Figure 19A:
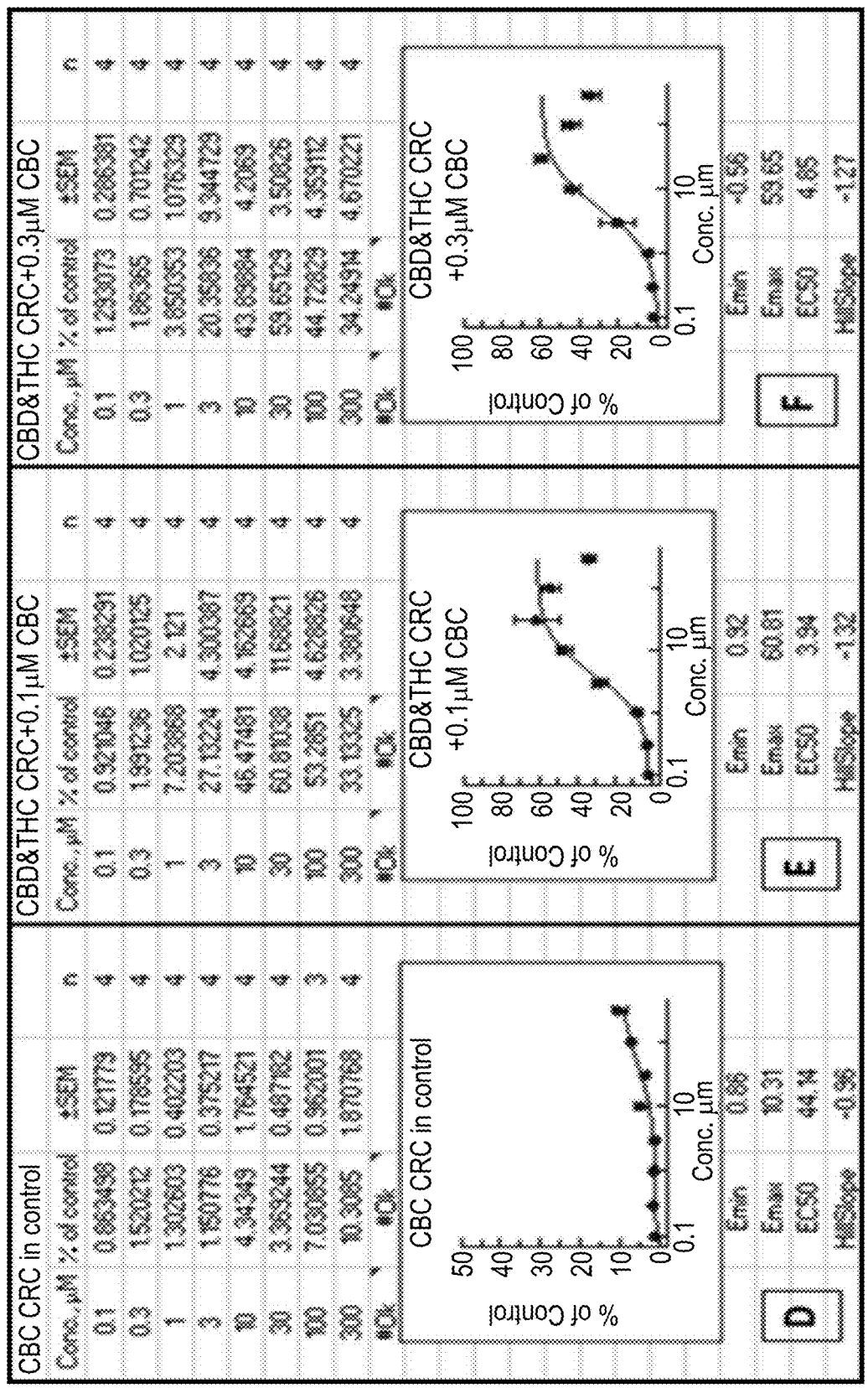
Figure 19B:
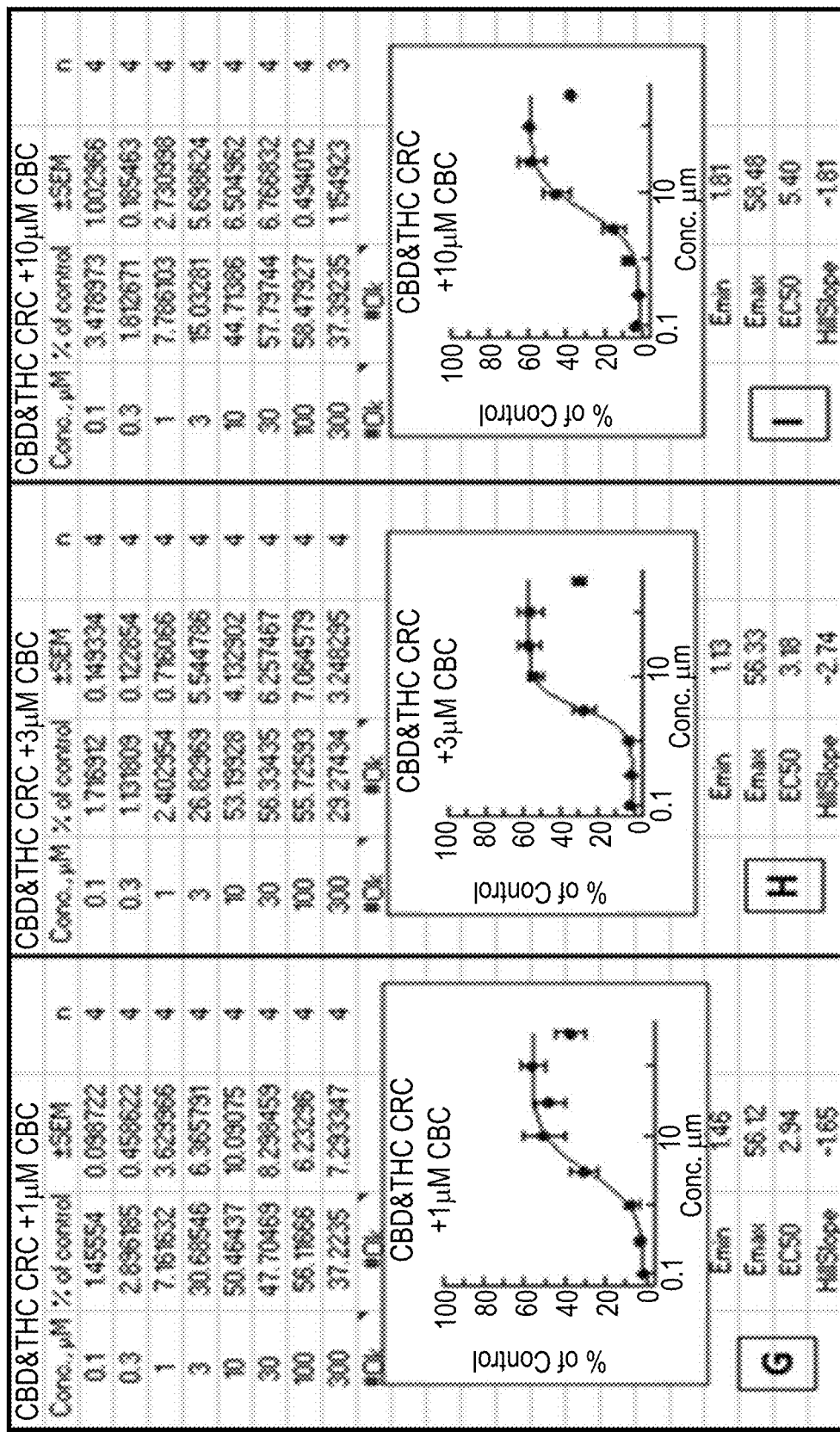
FIG. 19B provides plot representation and numeric information of activity of compounds at TRPA1 receptors showing a CBD+THC concentration response curve of agonist effects in Panels G to L.
Figure 19B:
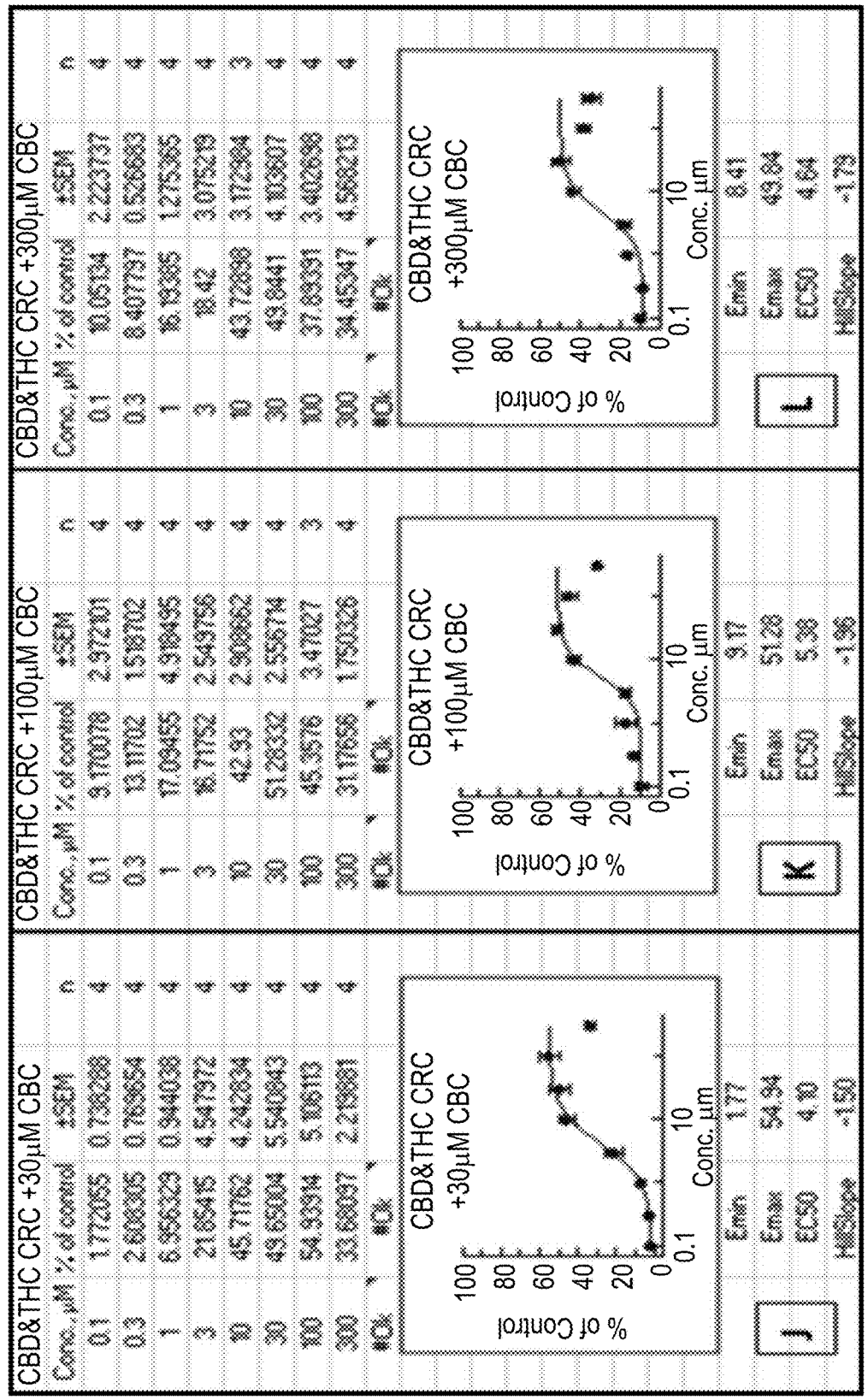
Figure 20A:
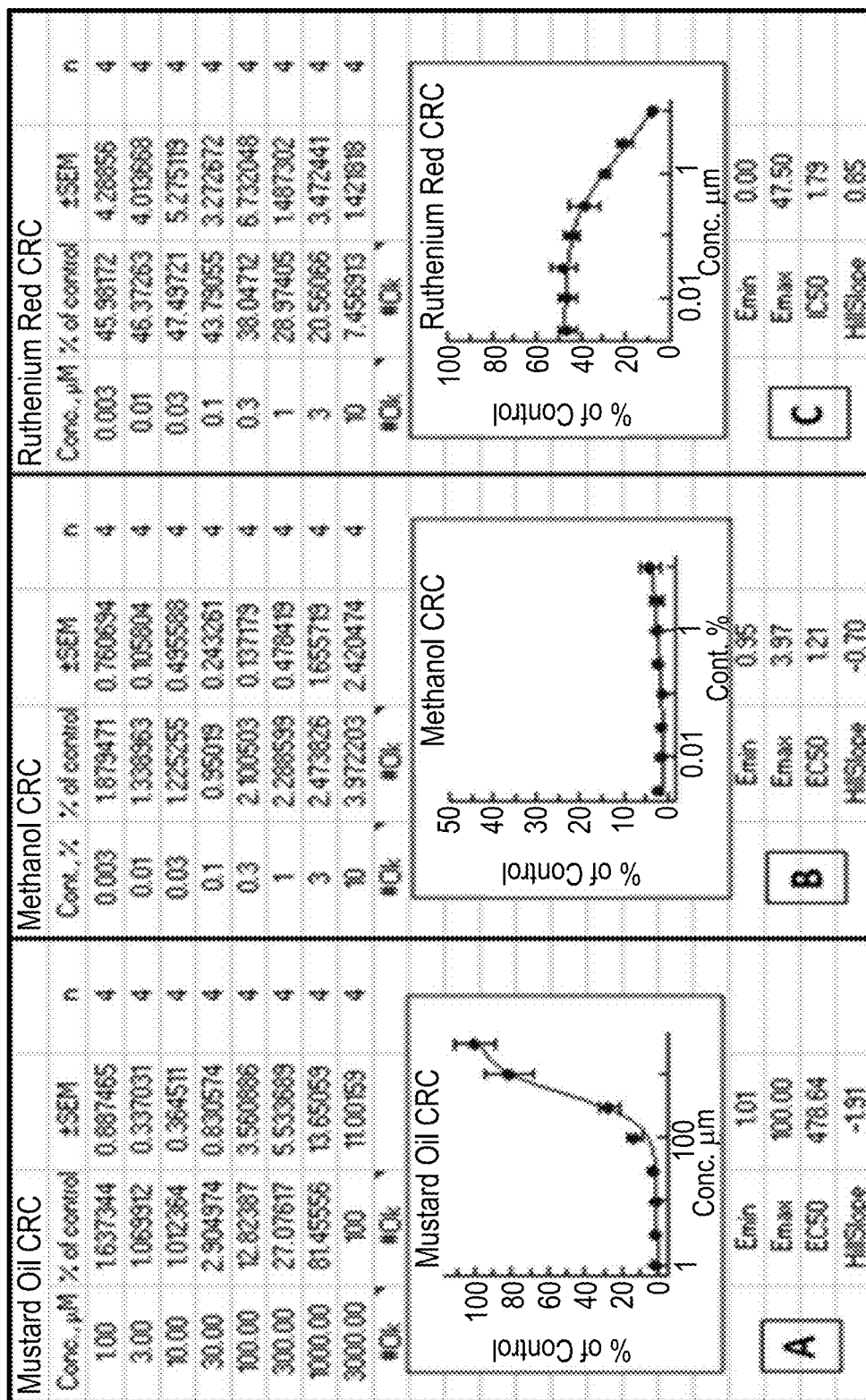
FIG. 20A shows plots and numeric information of activity of compounds at TRPA1 receptors for a CBC response curve of agonist effects in Panels A to F.
Figure 20A:
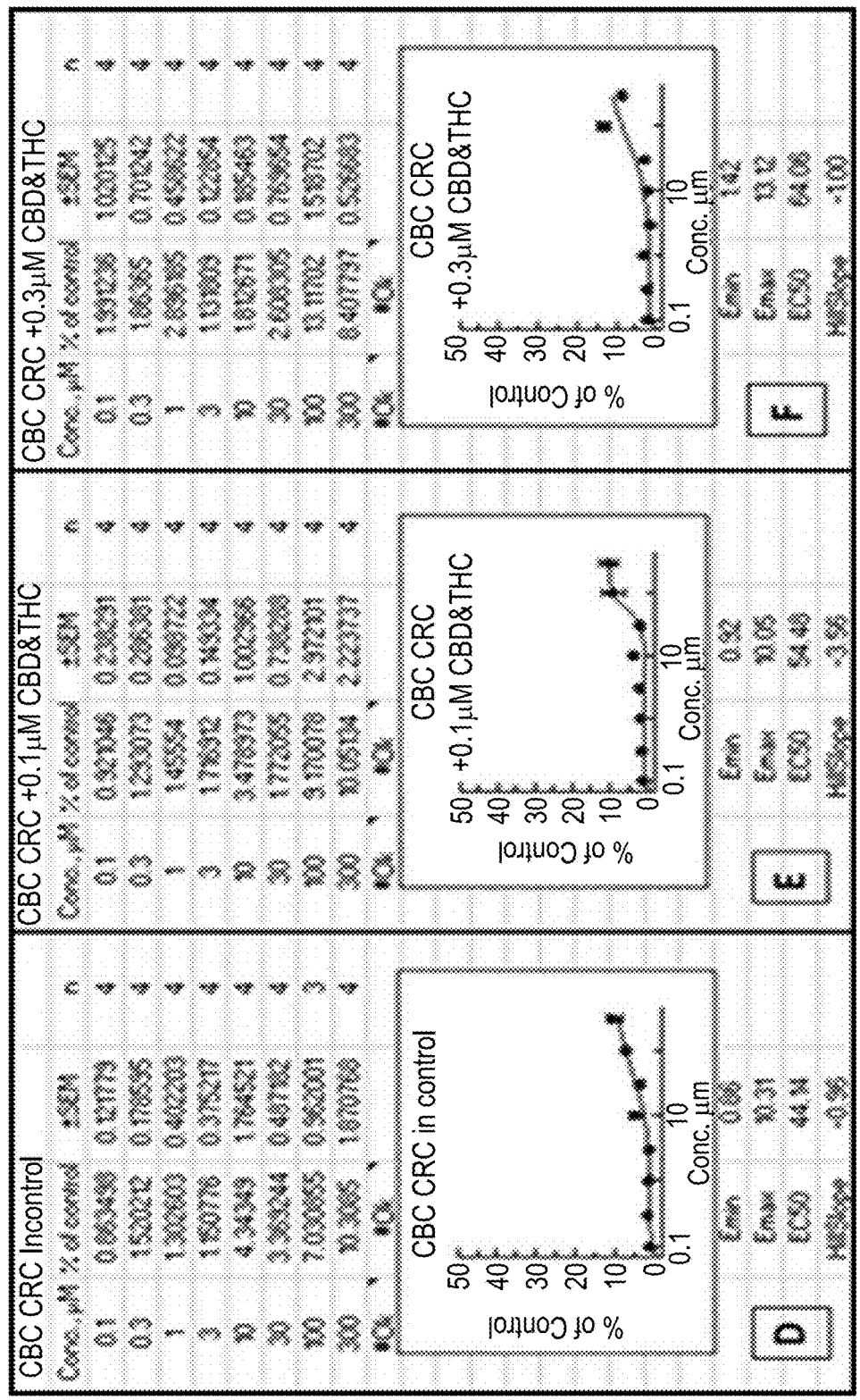
Figure 20B:
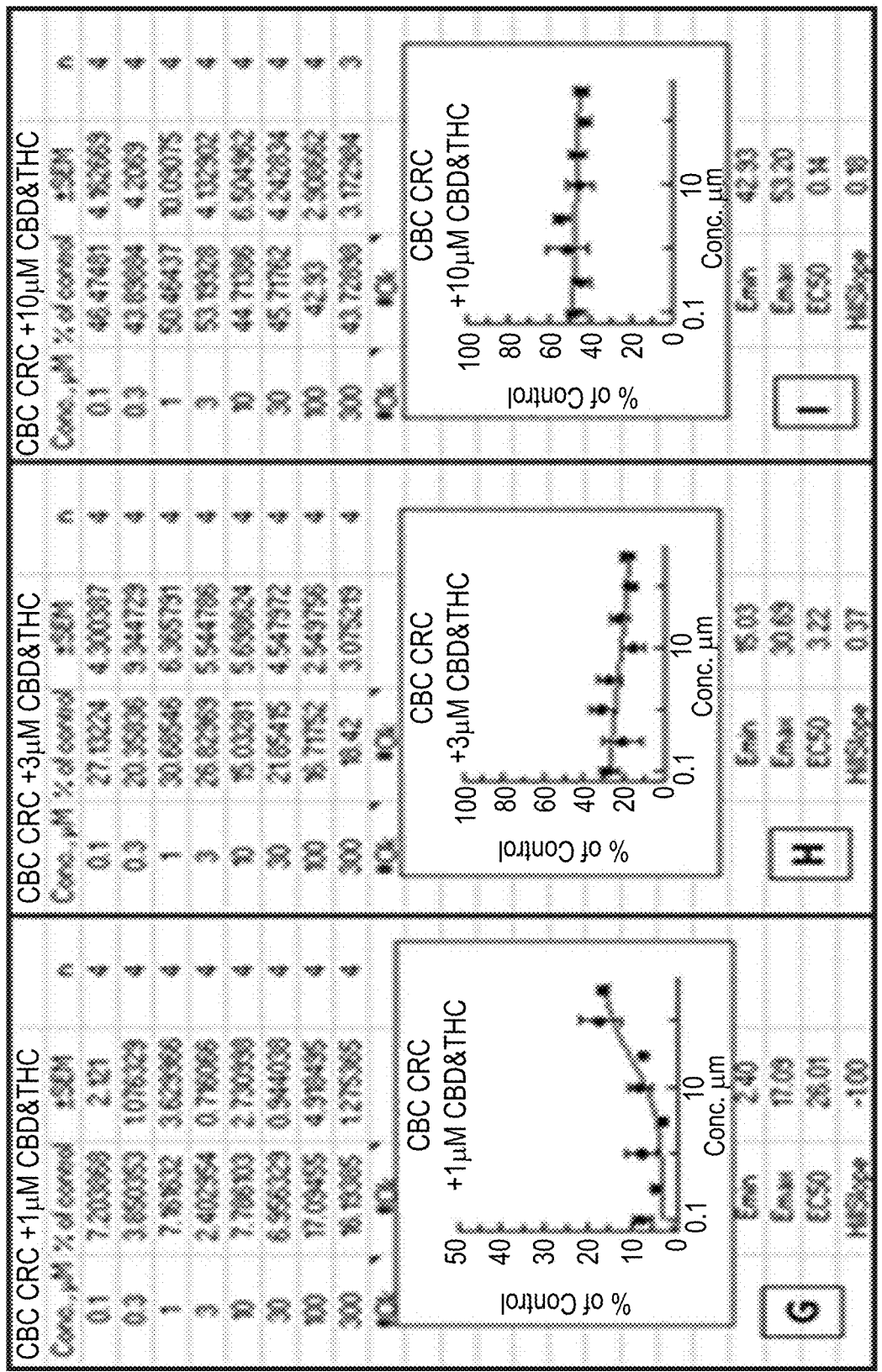
FIG. 20B provides plots and numeric information of activity of compounds at TRPA1 receptors for a CBC response curve of agonist effects in Panels G to L.
Figure 20B:
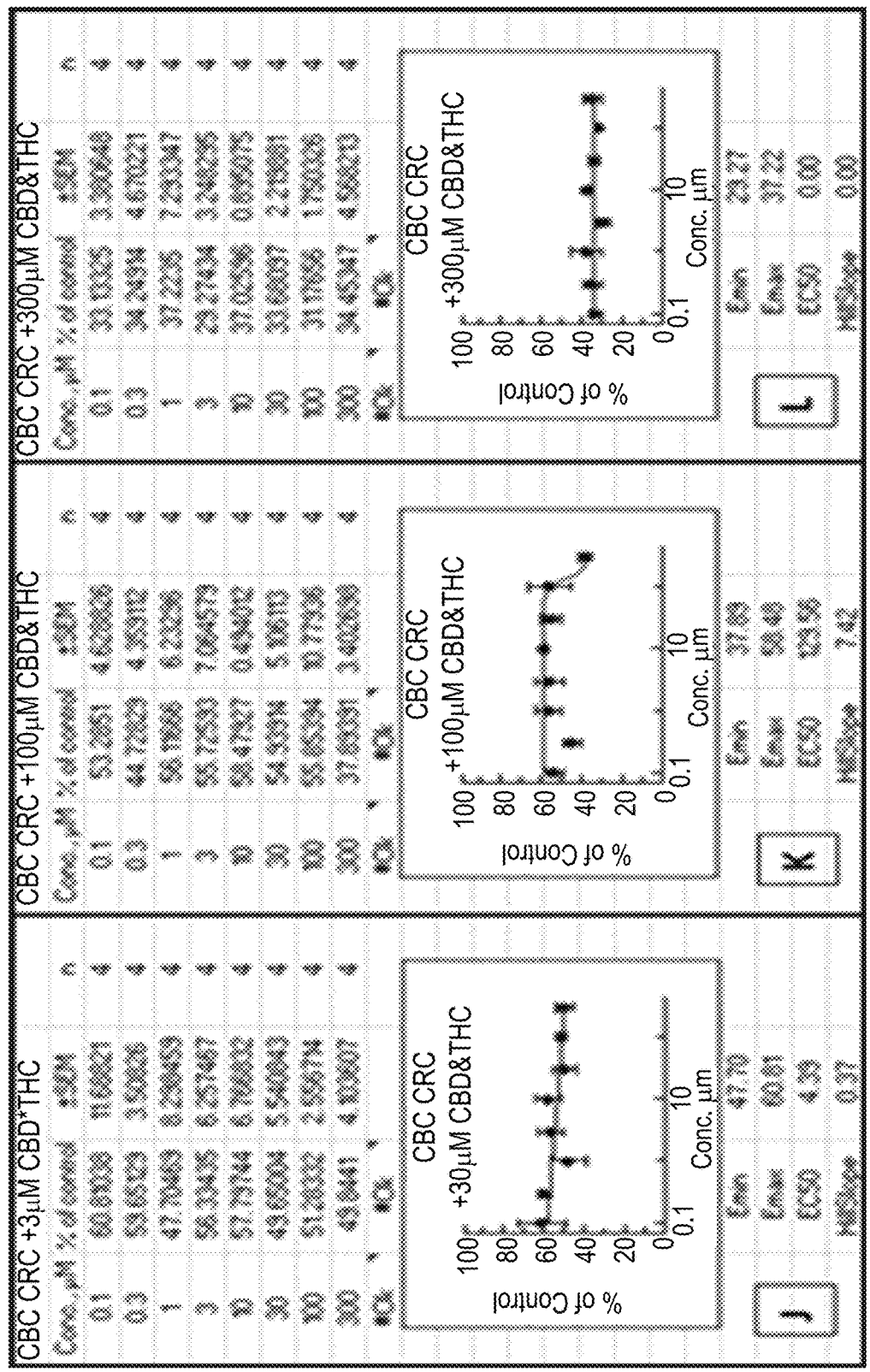

As shown in FIG. 19A and FIG. 19B, as well as in FIG. 20A and FIG. 20B, the percent of activation was calculated relative to currents produced by application of 3000 µM mustard oil.

FIG. 19A illustrates plot representation and numeric information of activity of compounds at TRPA1 receptors. Plots represent CBD+THC concentration response curve (CRC). Panel A: mustard oil CRC. Panel B: methanol CRC 0-10% half log scale. Panel C: ruthenium red CRC 0-10 µM, half log scale. Panel D: CBC CRC 0-300 µM. for Panel E (+0.1 µM CBC) and Panel F (+0.1 µM CBC): CBD+THC mixture concentration response curves in the presence of increasing concentration of CBC (0.1 and 0.3 µM). X-axis on E and F shows the concentration of CBD+THC (0.1 to 300 uM of each). All values are calculated relatively to current produced by 3000 µM mustard oil set as 100% (% of control).

FIG. 19B illustrates plot representation and numeric information of activity of compounds at TRPA1 receptors. Plots represent CBD+THC concentration response curve (CRC). Panels G to Panel L: CBD+THC mixture concentration response curves in the presence of increasing concentration of CBC (1-300 µM). X-axis on Panel G through Panel L shows the concentration of CBD+THC (1 to 300 µM of each). All values are calculated relatively to current produced by 3000 µM mustard oil set as 100% (% of control).

FIG. 20A shows plot representation and numeric information of activity of compounds at TRPA1 receptors. Plots represent CBC concentration response curve (CRC). Panel A: mustard oil CRC. Panel B: methanol CRC 0-10% half log scale. Panel C: ruthenium red CRC 0-10 µM, half log scale. Panel D: CBC CRC 0-300 µM. Panel E and Panel F: CBC CRC in the presence of increasing concentration of CBD+ THC mixture (0.1 and 0.3 µM each). All values are calculated relatively to current produced by 3000 µM mustard oil set as 100% (% of control).

FIG. 20B shows plot representation and numeric information of activity of compounds at TRPA1 receptors. Plots represent CBC concentration response curve (CRC). Panel G to Panel L: CBC CRC in the presence of increasing concentration of CBD+THC mixture (1-300 µM each). All values are calculated relatively to current produced by 3000 µM mustard oil set as 100% (% of control).

CBC showed a weak partial agonist activity at TRPA1 receptors with $EC_{50}$~40 µM and $E_{MAX}$~10%. CBD+THC mixture showed more potent, and more pronounced partial agonist activity with $EC_{50}$ ranged from 2.94 µM to 5.4 µM (at different concentrations of CBC) and $E_{MAX}$ equal 50%-60% relative to maximum current produced by 3000 µM mustard oil.

Data analysis were performed in two ways: First way: Table 5 and FIGS. 19A and 19B show CBD+THC mixture CRC in the presence of increasing concentration of CBC (0-300 µM). Second way: Table 6 and FIGS. 20A and 20B show CBC CRC in the presence of increasing concentration of CBD+THC mixture (0-300 µM each).

Table 5 shows numeric information of agonist activity of CBD+THC mixture (0-300 µM each) in the presence of increasing concentrations of CBC (0-300 µM). Note that CBC produced concentration response as a weak partial agonist which did not have significant effect on concentration response to CBD+THC mixture, but showed a trend towards agonist effect of all three cannabinoids together.

TABLE 5

Agonist Activity
CBD + THC CRC (% of 3000 µM Mustard Oil)

| # | CBC concentrations, µM | Agonist EMIN, % | EMAX, % | EC50, µM | Hill Slope |
|---|---|---|---|---|---|
| 1 | 0.1 | 0.92 | 60.81 | 3.94 | -1.32 |
| 2 | 0.3 | -0.56 | 59.65 | 4.85 | -1.27 |
| 3 | 1 | 1.46 | 56.12 | 2.94 | -1.65 |
| 4 | 3 | 1.13 | 56.33 | 3.18 | -2.74 |
| 5 | 10 | 1.81 | 58.48 | 5.40 | -1.81 |
| 6 | 30 | 1.77 | 54.94 | 4.10 | -1.50 |
| 7 | 100 | 9.17 | 51.28 | 5.38 | -1.96 |
| 8 | 300 | 8.41 | 49.84 | 4.64 | -1.79 |
| 1 | Mustard Oil | 1.01 | 100.00 | 478.64 | -1.91 |
| 2 | Methanol | 0.95 | 3.97 | 1.21 | -0.70 |
| 3 | Ruthenium Red* | 0.00 | 47.50 | 1.79 | 0.85 |
| 4 | CBC CRC | 0.86 | 10.31 | 44.14 | -0.96 |

*IC50 is shown

Table 6 shows numeric information of agonist activity of CBC in control (0-300 µM) and in the presence of increasing concentrations of CBD+THC mixture (0.1-300 µM). Note that CBD+THC mixture, in concentrations 3 µM, produced concentration own response, which occluded concentration response to CBC. Note that at threshold activation of TRPA1 receptors by CBD+THC mixture (1 µM), concentration response of TRPA1 receptors increased in potency and efficacy (shown as bold text).

TABLE 6

Agonist Activity
CBC CRC (% of 3000 µM Mustard Oil)

| # | CBD + THC concentrations, µM | Agonist $E_{MIN}$, % | $E_{MAX}$, % | $EC_{50}$, µM | Hill Slope |
|---|---|---|---|---|---|
| 1 | 0.1 | 0.92 | 10.05 | 54.48 | -3.56 |
| 2 | 0.3 | 1.42 | 13.12 | 64.06 | -1.00 |
| 3 | 1 | 2.40 | 17.09 | 26.01 | -1.00 |
| 4 | 3 | 15.03 | 30.69 | ND | ND |
| 5 | 10 | 42.93 | 53.20 | ND | ND |
| 6 | 30 | 47.70 | 60.81 | ND | ND |
| 7 | 100 | 37.89 | 58.48 | ND | ND |
| 8 | 300 | 29.27 | 37.22 | ND | ND |
| 1 | Mustard Oil | 1.01 | 100.00 | 478.64 | -1.91 |
| 2 | Methanol | 0.95 | 3.97 | 7.20 | -0.34 |
| 3 | Ruthenium Red* | 0.00 | 47.50 | 1.79 | 0.85 |
| 4 | CBC CRC control | 0.86 | 10.31 | 44.14 | -0.96 |

*IC50 is shown

CBC CRC has been occluded by increasing concentrations of CBD+THC mixture and starting with 3 µM CBD+THC mixture CBC CRC was masked.

CBC has no effect on CBD+THC mixture CRC $EC_{50}$ and $E_{Max}$. At highest concentrations CBC tested, initial portion of CBD+THC mixture CRC was increased, which resulted in marginal rightward shift of $EC_{50}$ for CBD+THC mixture CRC. It can be concluded that CBC and CBD+THC mixture produce receptors activation with different degree of partial agonism by acting at the same binding site of TRPA1 receptors.

Positive modulation of concentration response to CBC (synergy) was observed at the near threshold concentration of CBD+THC mixture (1 µM, Table 6 and FIG. 20A, Panel D and FIG. 20B, Panel G) and consisted of: (1) Leftward shift of concentration response curve to CBC from $EC_{50}$=44.1 µM (FIG. 20A, Panel D) to $EC_{50}$=26.0 µM (FIG. 20B, Panel G); and (2) Increased in efficacy from 10.3±1.9% (n=4) up to 16.2±1.3% (n=4) at 300 µM CBD+THC mixture.

Observed synergy of these two partial agonists can be attributable to the existence of two identical binding sites on TRPA1 receptor and positive cooperativity in binding of two ligand moieties to the receptors (orthosteric modulation). For example, binding of one ligand moiety to first binding site prime receptor or increase affinity of binding to the second binding site. An alternative explanation is an existence of positive allosteric modulation site. Without being limited to the mechanism of action, these synergistic effects were observed.

Conclusion

These data confirm direct activation of CBC on TRPA1 (Transient receptor potential Ankyrin 1) ion channel, as an important sensor of nociception in human.

The partial agonistic activity of CBC with CBD+THC mixture at the TRPA1 receptors was also confirmed.

The agonist activity of CBC with CBD+THC was presumably mediated via the same binding site.

At the near threshold activation of TRPA1 receptors with CBD+THC mixture (1 µM each), CBC activated TRPA1 receptors with greater efficacy and potency. Cannabichromene $E_{MAX}$ (efficacy) increased from 10±2% up to 16±1% and its potency from $EC_{50}$=44 µM to $EC_{50}$=26 µM (FIGS. 20A and 20B).

This study also confirms the synergistic effect between CBC and CBD+THC.

Observed synergy of these two partial agonists could be theoretically explained by existing of two identical binding sites on TRPA1 receptor and positive cooperativity in binding of two ligand moieties to the receptors (orthosteric modulation). For example, binding of one ligand moiety to first binding site would prime receptor or increase affinity of the second binding site. Alternative explanation is an existence of specific positive allosteric modulation site. Additional experiments must be designed to address an exact mechanism of these synergistic effects.

Altogether, direct effect of cannabichromene on activation of TRPA1 ion channels and the increase in potency of cannabichromene with CBD+THC further confirm that CBC has pain management properties. Therefore, addition of CBC to CBD and Δ9-THC can lower the intake of CBD and THC in patients for pain management.

Example 6

Data Mining Based on Multivariate Kinematic Gait Data

In this Example, data mining was performed to extend the multivariate kinematic data analysis and capture (a) Parameters indicative of analgesia vs. sedation phenotypes (analgesic or sedation 'fingerprint') (b) Quantitative measurement of parameters attributed to the temporal aspects of motion to evaluate temporal aspects of motion, such as positions, angles, velocities, and accelerations of body segments and joints during motion. Briefly, Contrastive Principal Component Analysis (cPCA) was utilized to identify different combinations of original variables which were linked to model effect, learning effect, and sedative effects. An orthogonalization procedure was used to make the obtained effects independent. cPC scores corresponding to identified cPCs were computed. In order to evaluate the analgesic and sedative effects of CBD:CBC:THC 5:5:5 mg/kg group, separate comparisons were performed with vehicle and pregabalin as controls, CBD+THC 10:10 mg/kg as positive control for sedation and CBC 10 mg/kg as negative control for sedation. The results of these comparisons were obtained by using all the previously identified components: model effect, learning effect and model orthogonal to learning, sedation orthogonal to model, and finally, the sedation orthogonal to both model and learning. The final sedative effect was also orthogonalized against both model and learning (speed effects), restricting to combination of gait changes which was associated with sedation. The sedative effect was carefully identified by using CBD:THC 10:10 mg/kg group at D8 9 h and was not linked to SNL model or learning effects. The parameters indicative of sedation were mostly associated with decreased overall speed, including increased stance and swing time, increased double support and decreased swing speed, as well as, decreased tail base height.

Regarding statistics, reference is made to a statistical method of Contrastive Principal Component Analysis (cPCA) (see Abid et al., 2018); a cPCA based analysis framework implemented by R environment (R version 3.6.3); and statistical analysis with lme4 (Bates et al., 2015) and emmeans (R version 1.4.5), R Foundation for Statistical Computing, Vienna, Austria.

Figure 21:
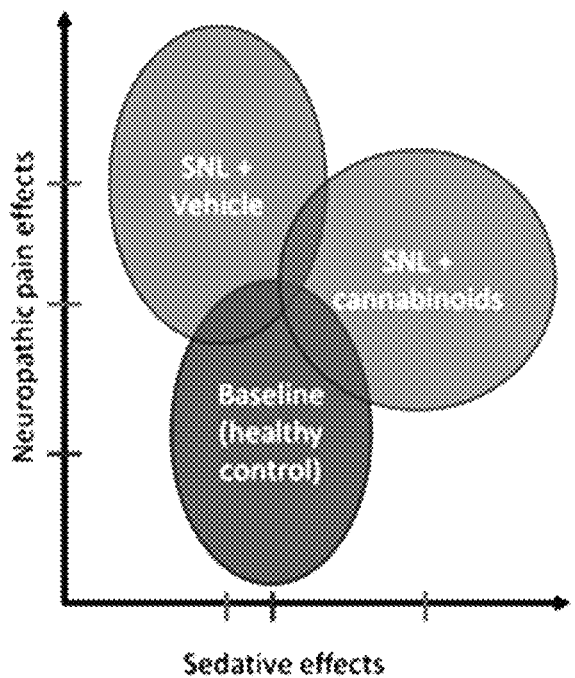
FIG. 21 shows a model of the neuropathic pain effects versus sedative effects on different axes. Cannabinoid groups may demonstrate treatment effects in the pain axis (Y-axis), while simultaneously, there might be a change in sedative effects (X-axis).

FIG. 21 shows a model of the neuropathic pain effects versus sedative effects on different axes. Cannabinoid groups may demonstrate treatment effects in the pain axis (Y-axis), while simultaneously, there might be a change in sedative effects (X-axis). The groups shown are: SNL+Vehicle (as a control for SNL-induced pain score); SNL+Cannabinoids versus Baseline (BL—healthy control).

Figure 22:
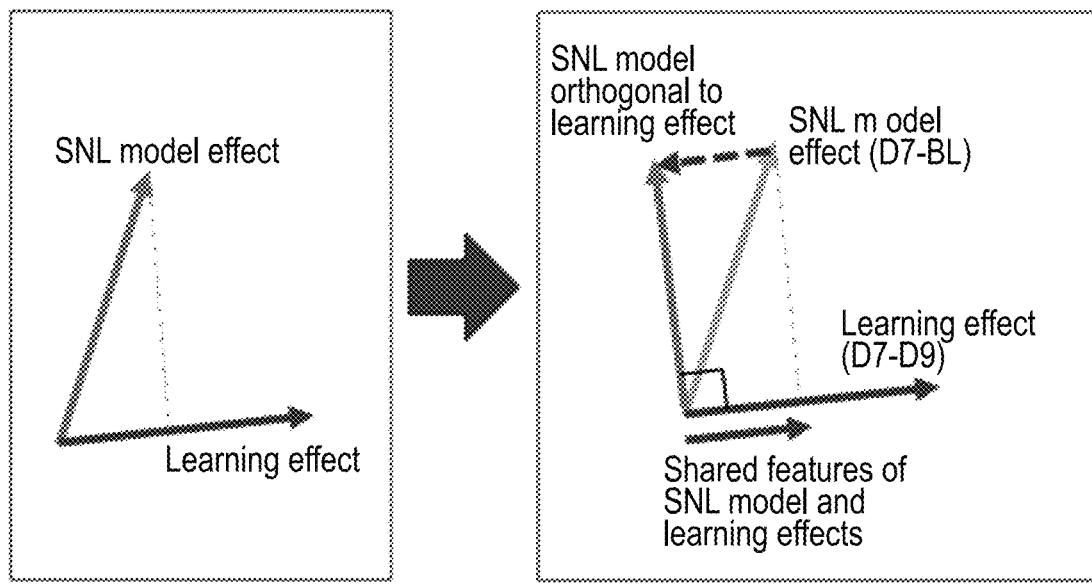
FIG. 22 depicts the orthogonalization of two components: Spinal Nerve Ligation (SNL) model effect and learning effect.

FIG. 22 depicts the orthogonalization of two components: Spinal Nerve Ligation (SNL) model effect and learning effect. The SNL Model effect and Learning effect share some common features (Left) and following the orthogonalization (Right), the learning effect (D7-D9) is "cleaned" from the SNL model effect (D7-BL), illustrating the shared features of SNL Model effect and Learning effect. The SNL Model orthogonal to the Learning effect is shown with the dashed arrow.

Results

SNL model score indicated a significant analgesic effect of CBD:CBC:THC 5:5:5 mg/kg that was comparable with that of CBD:THC combination when given at double the dose.

Figure 23:
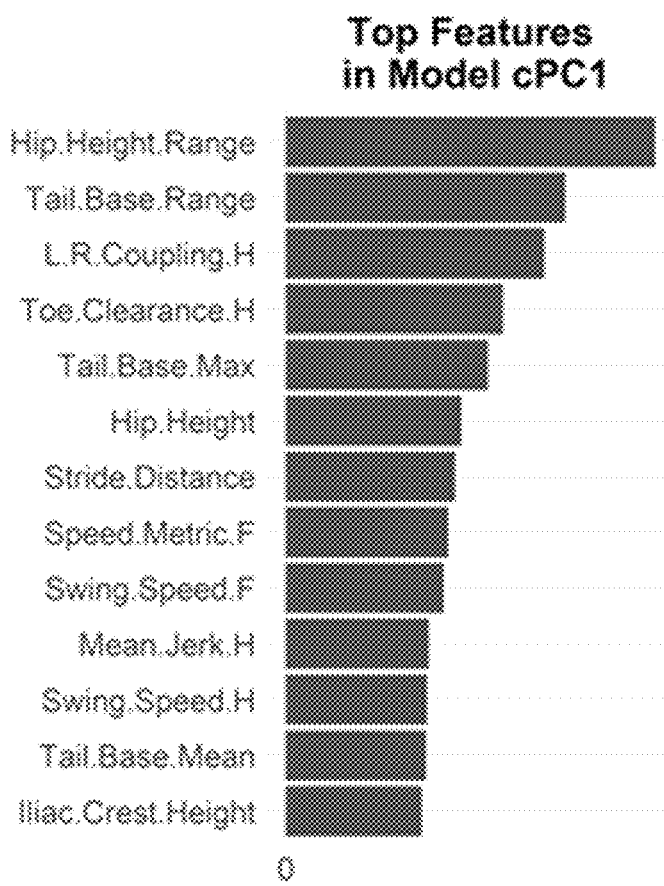
FIG. 23 shows the SNL model Contrastive Principal Components (cPC) and learning effect, with the bars indicating the rank-ordered most significant kinematic gait parameters associated with the SNL model.

FIG. 23 shows the SNL model Contrastive Principal Components (cPC) and learning effect, with the bars indicating the rank-ordered most significant kinematic gait parameters associated with the SNL model.

Figure 24:
FIG. 24 shows the SNL model cPC and learning effect, with the bars indicating the top parameters attributed to learning.

FIG. 24 shows the SNL model cPC and learning effect, with the bars indicating the top parameters attributed to learning.

Figure 25:
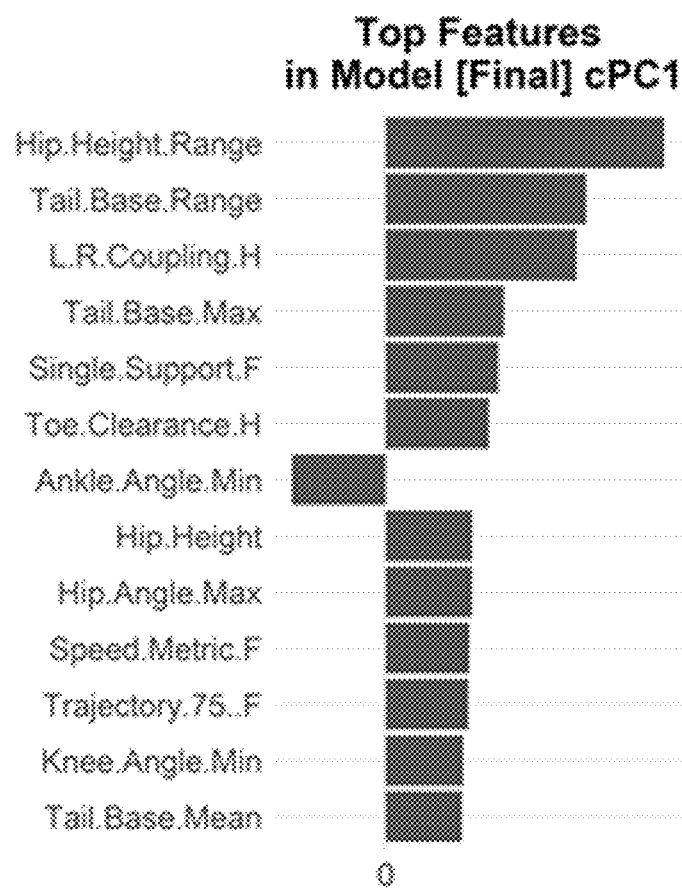
FIG. 25 shows the SNL model cPC and learning effect, with bars indicating the final SNL model score orthogonalized to learning.

FIG. 25 shows the SNL model cPC and learning effect, with bars indicating the final SNL model score orthogonalized to learning.

Figure 26:
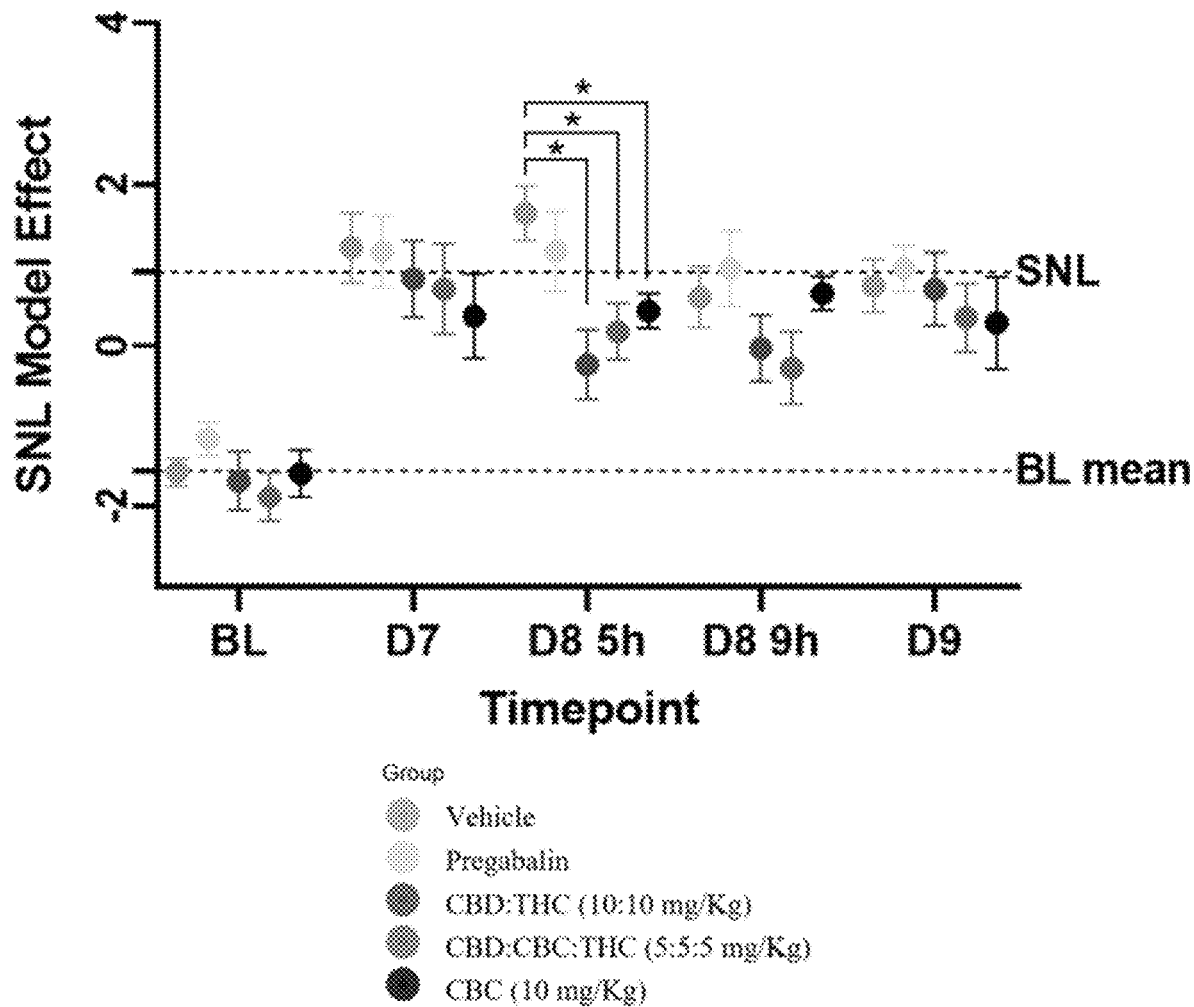
FIG. 26 provides final SNL Model scores based on SNL model effects orthogonalized against the learning effects. Data are presented as mean±SEM. Statistical significances: *p<0.05 (two-way mixed ANOVA followed by Dunnett's test). BL: Baseline; D8 5 h: Day 8 post-surgery at 5 hours post-treatment; D8 9 h: Day 8 post-surgery at 9 hours post-treatment; D9: Day 9.

FIG. 26 shows the effect of treatments on the final SNL-induced pain score (final SNL Model scores based on SNL model effects orthogonalized against the learning effects). Data are presented as mean±SEM. Statistical significances: *p<0.05 (two-way mixed ANOVA followed by Dunnett's test). BL: Baseline; D8 5 h: Day 8 post-surgery at 5 hours post-treatment; D8 9 h: Day 8 post-surgery at 9 hours post-treatment; D9: Day 9.

The SNL model score indicated a significant analgesic effect of CBD: CBC: THC at a level of 5:5:5 mg/kg and also showed reversal of SNL-induced pain at Day 8, 5 h post-dosing compared to vehicle group (FIG. 26). While CBD:THC with low doses of CBC (CBD:THC:CBC at 5:5:1 mg/kg) did not improve tactile allodynia in eVF (FIG. 6 and FIG. 7), CBD:CBC:THC at 5:5:5 mg/kg demonstrated a significant analgesic effect in eVF assay and improved kinematic performance 5 hours post-dosing. The improvement in motor skills of rats treated with CBD:CBC:THC formulation at 5:5:5 mg/Kg was comparable with that of THC:CBD combination when given at double the dose (THC:CBD at 10:10 mg/kg). These findings are suggestive of a potential synergistic effect of CBC with CBD and THC. This analgesic effect of CBD:CBC:THC at 1:1:1 ratio was not significant 9 hours post-dosing, which could be due to short half-life of cannabinoids (FIG. 26). The independent sedation effect scores (orthogonal to both SNL model and learning effects) are illustrated in FIG. 26.

Figure 27:
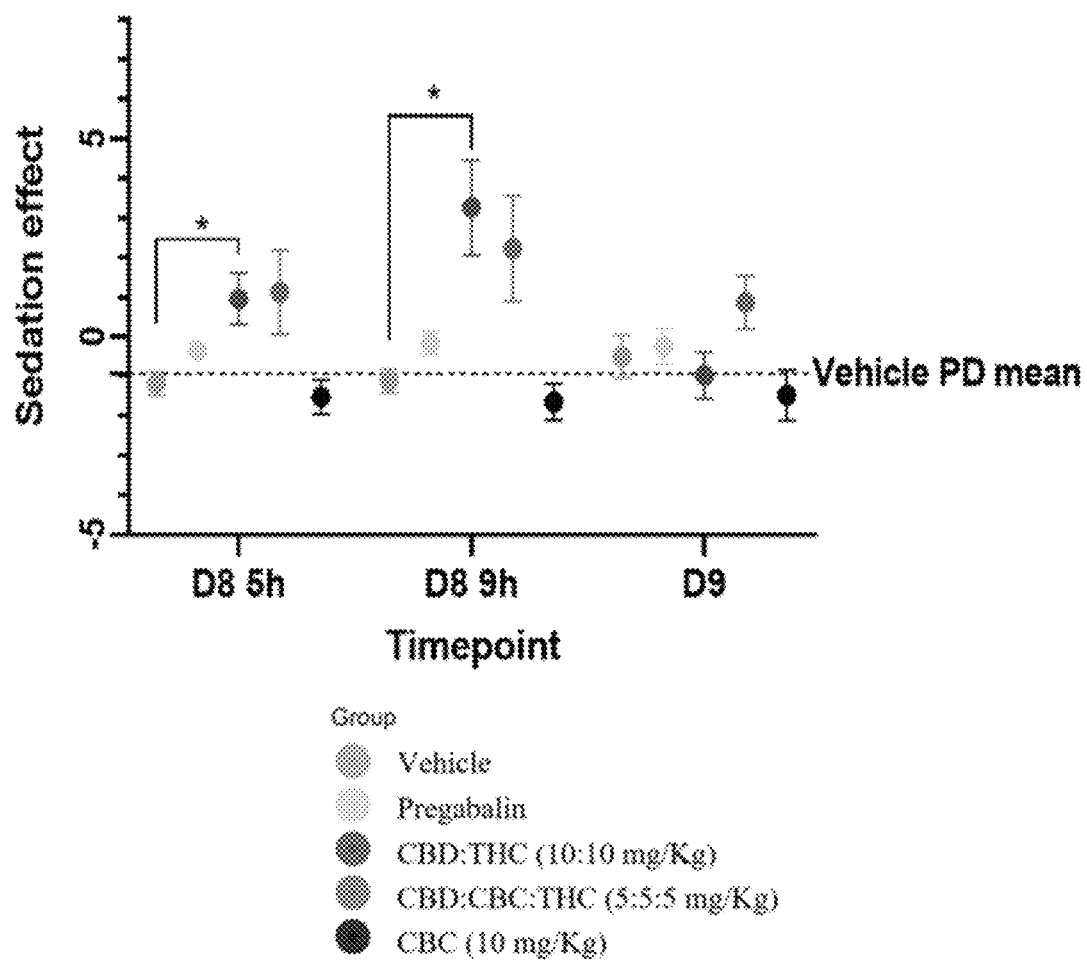
FIG. 27 shows final independent sedation effect scores, orthogonal to both SNL model and learning effects. Data are presented as mean±SEM. Statistical significances: *p<0.05 (two-way mixed ANOVA followed by Dunnett's test). BL: Baseline; D8 5 h: Day 8, 5 hours post-treatment; D8 9 h: Day 8, 9 hours post-treatment; D9: Day 9; PD: Post-dosing.

FIG. 27 shows final independent sedation effect scores, orthogonal to both SNL model and learning effects. Data are presented as mean±SEM. Statistical significances: *p<0.05 (two-way mixed ANOVA followed by Dunnett's test). BL: Baseline; D8 5 h: Day 8, 5 hours post-treatment; D8 9 h: Day 8, 9 hours post-treatment; D9: Day 9; PD: Post-dosing. This score captures significant sedative effects only in the CBD:THC 10:10 mg/kg treatment group at D8, 5 h and D8, 9 h post-dosing (FIG. 27). This finding was consistent with the evF assay outcome.

Figure 28:
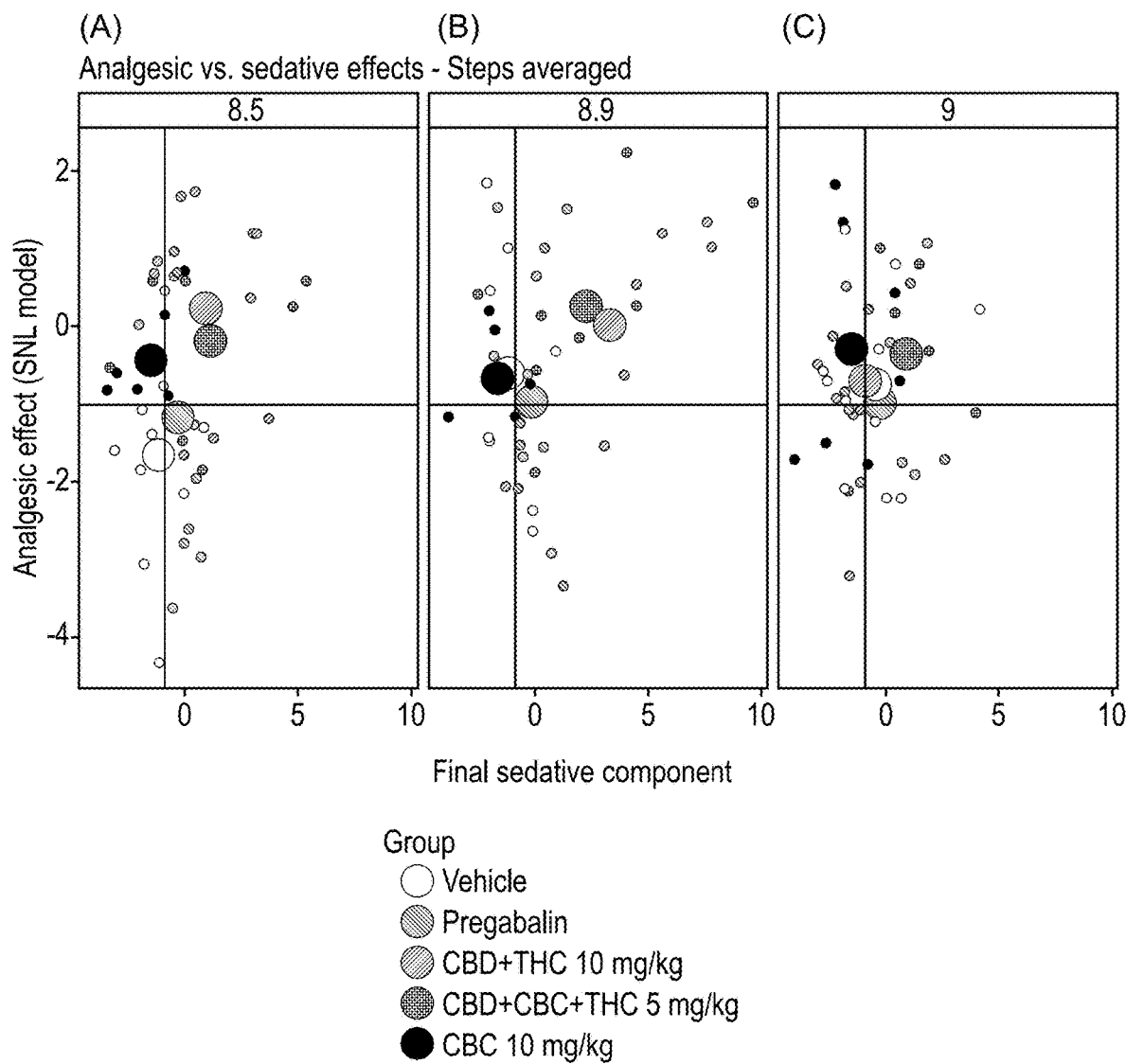
FIG. 28 depicts analgesic vs. sedative effect scores presented as XY-plot. The final independent sedation score is presented on X-axis and final analgesic score (inverted final SNL model score) on Y-axis. Each small dot represents one animal (average of analyzed gait cycles). Large dots illustrate the group means: (Panel A) D8 5 h post-dosing; (Panel B) D8 9 h post-dosing; (Panel C) Day 9 post-dosing.

FIG. 28 depicts analgesic vs. sedative effect scores presented as XY-plot. The overall analgesic vs. sedative effect of each treatment 5-24 hours post-dosing (gait cycles averaged) is shown. The final independent sedation score is presented on X-axis and final analgesic score (inverted final SNL model score) on Y-axis. Each small dot represents one animal (average of analyzed gait cycles). Large dots illustrate the group means: (Panel A) D8 5 h post-dosing; (Panel B) D8 9 h post-dosing; (Panel C) Day 9 post-dosing.

Conclusion

Data mining successfully determined the analgesic effect and sedative effect of multiple treatments by comparing 97 different gait parameters in each animal.

The final SNL model effect was most distinctively associated with the following parameters: increased vertical hip movement, gait asymmetries, and increased hind limb toe clearance.

The parameters indicative of sedation were mostly linked to decreased overall speed (increased stance and swing times, increased double support and decreased swing speeds) or decreased tail base height.

The data mining indicated that Pregabalin treatment at 50 mg/kg exhibited no analgesic or sedative effect in the kinematic data. This lack of efficacy of Pregabalin in pain management was consistent with the results of the evF test when the time points were analyzed separately. The only significant effect of Pregabalin was found in the area under curve (AUC) analysis of evF. However, evF analyses revealed a marked analgesic effect of CBD:CBC:THC at a level of 5:5:5 mg/kg has superior analgesic effect when compared to Pregabalin (50 mg/kg), a GABA analogue that is among the first-line treatment choices for neuropathic pain (p=0.0186). Analysis of fine motor kinematic parameters further confirmed that Pregabalin treatment exhibited no analgesic or sedative effect on the kinematic gait performance Significant recovery in SNL model effect score were found in CBD:THC 10:10 mg/kg and CBD:CBC:THC 5:5:5 mg/kg treatment groups at D8 5 h post-dosing, while no analgesic effect was indicated at 9 h post-dosing. This finding indicates that recovery in the SNL model score is associated with the analgesic treatment effect.

The CBD:CBC:THC formulation at a level of 5:5:5 mg/kg demonstrated a significant analgesic effect at D8 5 h post-dosing. This analgesic effect was comparable with that of a CBD:THC combination when given at double the dose, suggesting a potential synergy in the analgesic effect of CBC when used in combination with CBD:THC.

Final independent sedative effect was found only in the CBD+THC 10 mg/kg group at both D8 5 h and D8 9 h post-dosing.

Utilizing CBD:CBC:THC at a level of 5:5:5 mg/kg demonstrated a marked reversal of SNL-induced pain as indicated by improvement in interlimb coordination, enhanced body posture, and rectified knee and ankle angles.

Overall, CBD:CBC:THC at a level of 5:5:5 mg/kg exhibited a marked reversal of motor impairments indicated by changes in motor skill parameters associated with improvement in interlimb coordination, enhanced body posture, and rectified knee and ankle angles. This finding might offer a practical guide to study motors skill changes in clinical setting in patients with chronic pain. This study also identified that parameters associated with sedation are attributed to decreased overall speed, such as increased stance and swing time, increased double support and decreased swing speed, and decreased tail base height. These finding may offer clinically translatable solutions in human clinical trials.

These results affirm that a formulation comprising CBD:CBC:THC 5:5:5 can effectively achieve pain management in the Spinal Nerve Ligation (SNL) model.

Example 7

The Effects of Single- and Repeated-Dose Treatment with CBD:CBC:THC at 1:1:1 Ratio on Management of Chemotherapy-Induced Polyneuropathy In this Example, a pain model was used to compare efficacy of a multi-cannabinoid formulation and a known pain relieving medication, Duloxetine. Duloxetine is medicine within a class of drugs referred to as serotonin-norepinephrine reuptake inhibitors (SNRIs) for use in treatment of pain.

Methods

Model Induction—Mouse Oxaliplatin-induced polyneuropathy (OIPN) model was induced over a three-week period. The day of first Oxaliplatin (OXP) injection is referred to as day 0 (D0). OXP was administered as six separate intraperitoneal injections at 4.5-mg/kg (10 mL/kg, i.p.) to Groups 2, 3, and 4 on D0, D4, D8, D12, D16, and D20. The cumulative OXP dose was thus 27 mg/kg. The in-life procedures, such as observations, tests, and/or measurements were performed by Charles River Discovery Services with blinded methods. The mice were distributed into 4 groups (n=8 for Vehicle Control; n=10 OXP Control; n=20 CBD:CBC:THC; n=15 Duloxetine).

TABLE 8

Planned and Accomplished Group Sizes (N)

| Group # | Group | Planned N | Actual N |
|---|---|---|---|
| 1 | Veh.-Veh | 8 | 8 |
| 2 | OXP-Veh. | 10 | 10 |
| 3 | OXP-CBD:CBC:THC at 5:5:5 mg/kg | 20 | 19 |
| 4 | OXP-Dulx. | 15 | 13 |

Measurement of Plasma Bile Acid Concentration—A significant percentage of C57BL/6J mice have a portosystemic liver shunt, which results in major alteration of brain morphometry, brain metabolites, physiological readouts (such as body weight and liver enzymes), and cognitive deficits. Prior to study initiation, plasma bile acid measurement was performed to exclude animals with abnormally high bile acid concentration (>15 µmol/L), which is a surrogate marker of the portosystemic liver shunt (Cudalbu et al. 2013). The bile acid concentrations were analyzed by an outsourced third-party, using Thermofisher Konelab Xti 20™ according to manufacturer's instructions.

Body Weight—Animal body weights were measured before assigning the treatment groups and then on each day of the study. The last body weight measurement was performed upon endpoint sampling. Terminal body weights were not collected from animals found dead or euthanized moribund.

Treatments—Following exposure to OXP for 20 days, Groups 3 and 4 were treated with CBD:CBC:THC (5:5:5 mg/kg, p.o.) and Duloxetine (25 mg/kg, i.p.), respectively, for 10 consecutive days. In a similar regimen Groups 1 and 2 (Vehicle Control and OXP-Vehicle Control, respectively) received a corresponding volume of 5% glucose solution at an administration volume of 10 mL/kg.

Acetone Cooling Test (ACT)—To produce a measurable cooling sensation, 10-15 µL of acetone was applied onto the medial area of the plantar hind paw with a 0.5 ml insulin syringe. Responses of a mouse to acetone were monitored for 20 s, and a score given based on a four-point scale (0-3 points), according to the response intensity, continuation, and briskness. The higher the score, the greater the cool allodynia sensed by the mouse.

Within one test timepoint, a total of 3 trials were performed per paw with a minimum gap of 5 min between testing. The three individual scores were added up to obtain a single score over a cumulative period of 60 s. Thus, for one test, the minimum score of one paw is 0 (no cool allodynia), while the maximum possible score is 9 (intensive cool allodynia). The total scores for the left and right paws were averaged to accomplish a single result value per mouse at each timepoint.

The Acetone Cooling Test was performed prior to OXP administration (Baseline), following the last OXP injection (D21), one day after the first CBD:CBC:THC, Duloxetine, or Vehicle treatment (D22), and after a 10-day daily dosing of CBD:CBC:THC, Duloxetine, or Vehicle treatment (D31). Taken together, the ACT was used to assess chemotherapy-induce cool allodynia as stated in the schedule:

Test days: Baseline, D21, D22, D31 (D0=day of first OXP injection).

Baseline: Measure cool allodynia as a baseline in healthy animals.

On D21: Test for accomplished cool allodynia level after OXP challenge.

On D22: At 60 min after the first Vehicle/CBD:CBC:THC dose and 120 min. after Dulx dose.

On D31: At 60 min after the last Vehicle/CBD:CBC:THC and 120 min after Dulx dose.

Prior to the ACT, mice underwent 30-60 min habituation in the test room and approximately 30-60 min habituation in the test chambers. Before baseline ACT, mice were pre-handled for 2 min on two consecutive days in their maintenance room for the purpose of decreasing false oversensitivity.

Results

These data illustrate that the formulation CBD:CBC:THC is effective in pain management.

Body Weight and Welfare—Out of a total of 90 mice, 76 were accepted for the baseline tests as they displayed normal plasma bile acid contents—i.e. 24 mice were disqualified from the study due to very high BA concentration in plasma, indicating the portosystemic shunt. Seven mice were disqualified from further study due to showing too mild cool allodynia. Furthermore, the welfare observations made upon testing found that Duloxetine caused the most adverse effects, as 30% of the group displayed enlarged staring eyes and clearly decreased activity.

Oxaliplatin chemotherapy does not dramatically affect the body weight (BW) development. The raw BW values were normalized by the baseline weight, to obtain % BW Change from Baseline. The group means of this value are shown in FIG. 29.

Figure 29:
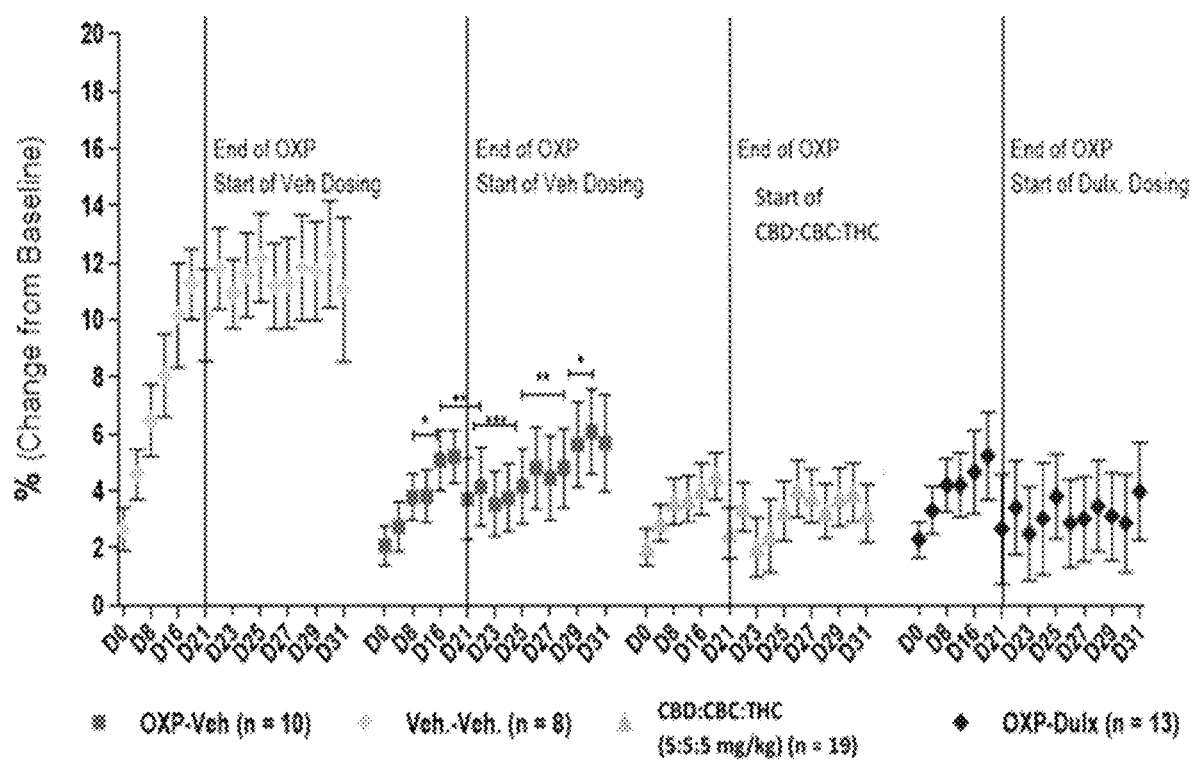
FIG. 29 shows body weight development presented as Mean % BW change from baseline for Example 7.

FIG. 29 shows body weight development presented as Mean % BW Change from Baseline. Data are presented as mean±SEM. Two-way ANOVA, Sidak's multiple comparisons test is used for comparisons to Vehicle-Vehicle vs. OXP-Vehicle *$p<0.001$; $p<0.01$; *$p<0.05$ Base=Baseline. The x-axis indicates the mean baseline BW. For simplicity, the vertical lines indicate the end of OXP exposure (D21) and the beginning of the Veh./CBD:CBC:THC/Dulx dosing (D22).

During the OXP exposure period, a slight weight gain of a few percentages is seen (compared to approximately 10% on Veh.-Veh. group). From D22 onwards, all groups display a slight decrease in body weight that starts increasing—depending on the group. A slower increase in body weight observed in CBD:CBC:THC and duloxetine—treated groups may be due to the loss of appetite that can potentially be due to the treatment.

Figure 30:
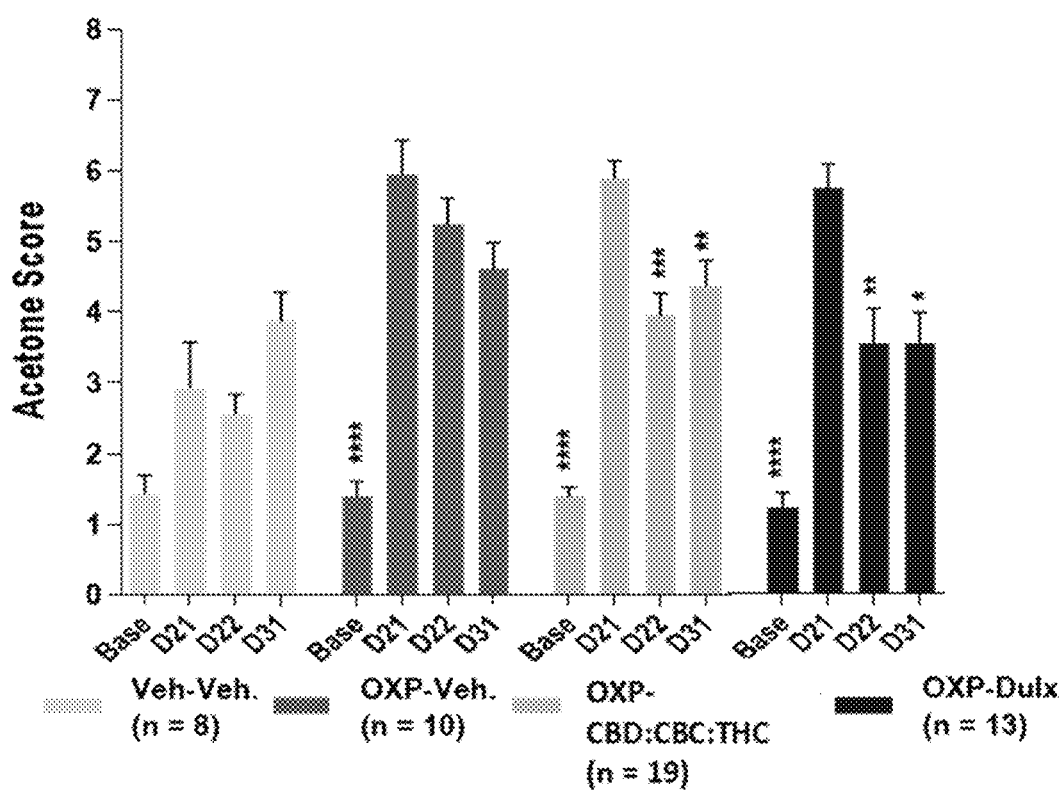
FIG. 30 shows within treatment group comparison of mean ACT scores at indicated timepoints for Example 7.

Acetone Cooling Test—FIG. 30 shows timepoint-comparison of ACT scores within each treatment group. Highly significant cool allodynia was induced by OXP in all treatment groups (FIG. 30; Baseline vs. D21). Upon the single dose treatment (D22) test timepoint, CBD:CBC:THC (5:5:5: mg/kg) treatment group showed the most significant reversion of chemotherapy-induced cool allodynia compared to D21 pre-treatment ($p<0.001$). Although Duloxetine induced a significant reversion of cool allodynia, it did not reach the same significance level as the CBD:CBC:THC treatment group (at 5:5:5: mg/kg; $p<0.01$).

FIG. 30 shows a within treatment group comparison of mean ACT scores at indicated timepoints. Data are presented as mean+SEM. Two-way ANOVA, Dunnett's multiple comparisons test is used for comparisons to D21 (pre-treatment). **$p<0.0001$; *$p<0.001$; **$p<0.01$; *$p<0.05$ Base=Baseline.

Moreover, 10-day repeated dosing with CBD:CBC:THC at 5:5:5 mg/kg showed significant reversion of chemotherapy-induced cool allodynia (D31 vs. D21). Similarly, repeated dosing with Duloxetine showed a significant reduction of cool allodynia (D31 vs. D21) (FIG. 30).

Figure 31:
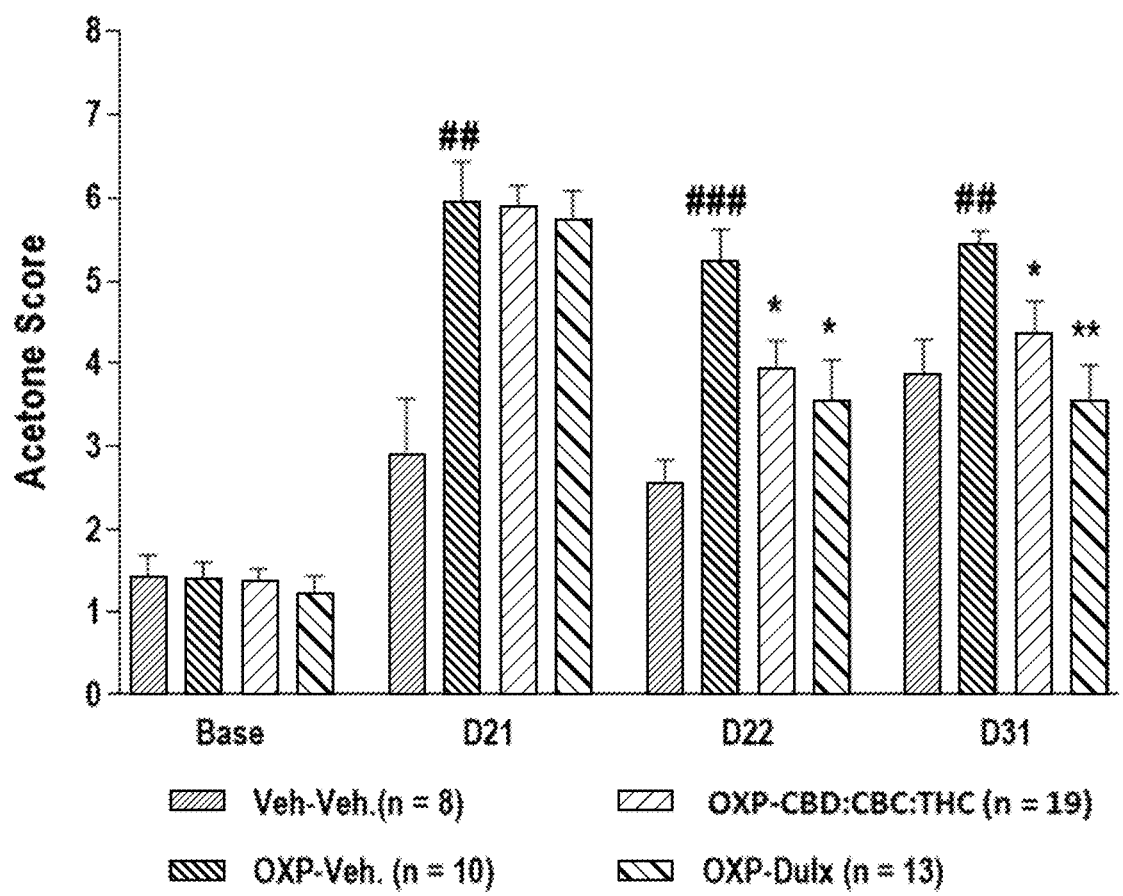
FIG. 31 shows between treatment group comparison of mean ACT scores at indicated timepoints in Example 7.

In addition, FIG. 31 shows between treatment group comparison of mean ACT scores after an acute single dose (D22) or chronic repeated dosing (D31). Acute dosing with CBD:CBC:THC at 5:5:5 mg/kg or Duloxetine showed a statistically significant and comparable reduction in cool allodynia as compared with the OXP-Vehicle control. At the chronic dosing timepoint (D31), CBD:CBC:THC (5:5:5 mg/kg) or Duloxetine maintained a significant reduction in cool allodynia (FIG. 31).

FIG. 31 shows a between treatment group comparison of mean ACT scores at indicated timepoints. Data are presented as mean±SEM. **$p<0.01$; *$p<0.05$, compared to the OXP-Veh. at the same timepoint (Mann-Whitney test); ###$p<0.001$; ##$p<0.01$, OXP-Veh. compared to Veh-Veh. at the same timepoint (Mann-Whitney test).

Conclusion

The CBD:CBC:THC (5:5:5 mg/kg) formulation was shown to be as effective at managing pain as a known pain relieving medication.

After the Oxaliplatin (OXP) exposure period, all OXP-treated groups displayed highly robust OIPN model induction as confirmed by the acetone cooling test (ACT).

CBD:CBC:THC (5:5:5 mg/kg) or Duloxetine (25 mg/kg) showed a comparable and significant reversion in polyneuropathy (chemotherapy-induced pain) upon single-dose treatment as measured by the ACT.

Upon chronic multiple-dose treatment for 10 days, CBD:CBC:THC (at 5:5:5 mg/kg) and Duloxetine caused a significant reduction in polyneuropathy (chemotherapy-induced pain) as measured in the ACT, as compared to the corresponding Vehicle control (Veh-OXP) group.

Of note, Duloxetine is the only recommended treatment for chemotherapy-induced peripheral neuropathy (CIPN) by the American Society of Clinical Oncology and the systematic review of treatments for CIPN show evidence for a moderate benefit of duloxetine (Hou et al. 2018). However, Duloxetine therapy causes significant side-effects. In accordance, in this study pronounced adverse effects were observed in 30% of the Duloxetine group, which included enlarged staring eyes and obvious decreased overall activity. Similar manifestations were observed following CBD:CBC:

THC treatment at 5:5:5 mg/kg, however, the effects were notably very mild by comparison.

These results affirm efficacy of a formulation comprising CBD:CBC:THC 5:5:5 in pain management.

Example 8

Formulation Pairing for Day and Night Multi-Dose Pain Management Regime

In this Example, a regime involving a day and night pairing of formulations is described for use in pain management. Individuals wishing to achieve pain management, but who may nevertheless wish to avoid any psychoactive effect of $\Delta^9$-THC (tetrahydrocannabinol, herein THC) during daytime or waking hours may utilize a formulation pairing in which THC is only present in the evening or bed time doses of the regime. THC can exert psychoactive activity, which may or may not be desirable to an individual at certain times of day, while such effects in the evening or at bedtime may be desirable. Other primary cannabinoids, such as cannabichromene (CBC) and cannabidiol (CBD), can exert the pain managing effects but without psychoactive activity.

A regime comprising taking a CBC:CBD formulation by day or at desired times, combined with a THC:CBC:CBD formulation in the evening or at bedtime or at desired times can address the varied needs of individuals wishing to achieve pain management.

In a multi-dose daily regime, for which an individual takes a morning dose (or breakfast dose), a mid-day dose (lunch time dose), an evening dose (dinner/supper time dose), and/or a night time (bedtime) dose, a formulation pairing may involve a CBC:CBD 1:5 to 5:5 (weight ratio) formulation that is taken at 8:00 am and 1:00 pm, followed by a THC:CBC:CBD 5:5:5 to 5:1:5 (weight ratio) formulation at 6:00 pm and 11:00 pm. By reserving the effect of the THC for the evening and bedtime doses, the THC effect can be reserved for certain times of day when an individual has no reservation regarding possible psychoactive effects.

(a) An exemplary pain management formulation may involve a paired formulation regime of: a first formulation at 7:30 am and 12:00 noon of comprising CBC:CBD 5:5; and a second formulation at 5:00 pm and 10:00 pm comprising THC:CBC:CBD 5:5:5, with sleep occurring between 11:00 pm and 7:00 am.

(b) An exemplary pain management formulation may involve a paired formulation regime of: a first formulation at 8:00 am, 1:00 pm, and 6:00 pm comprising CBC:CBD 3:5; and a second formulation at bedtime only (approximately 11:00 pm) comprising THC:CBC:CBD 5:3:5, with sleep occurring between 11:00 pm and 8:00 am.

(c) An exemplary pain management formulation for an individual working a night shift from 11:00 pm to 7:00 am may involve a paired formulation regime of: a first formulation upon waking at 5:00 pm; prior to the start of a night shift at 9:00 pm; and while on shift at 3:00 am, which first formulation comprises CBC:CBD 1:5. The second formulation may be taken at bedtime (approximately 9 am) comprising THC:CBC:CBD 5:3:5, with sleep occurring between 9:00 am and 5:00 pm.

(a) An exemplary pain management formulation may involve a paired formulation regime wherein a dose is taken every 4 hours until bedtime, wherein the first doses of the day comprise: a first formulation comprising CBC:CBD 5:5 every 4 hours until bedtime; and a second formulation is taken at bedtime only, and comprises THC:CBC:CBD 5:5:5, with sleep occurring at the individual's preferred time of day.

Conclusion

The formulation pairing permits flexibility for individuals who may wish to defer or delay the THC-containing formulation for the evening or sleeping hours, to promote maximum alertness and/or avoid psychoactive effects during certain times of day.

In the preceding description, for purposes of explanation, numerous details are set forth in order to provide a thorough understanding of the embodiments. However, it will be apparent to one skilled in the art that these specific details are not required. References cited herein are incorporated by reference.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

The following documents are herein incorporated by reference.

WO2016/044370 A1
WO2013/165251 A1
WO2012/144892 A1
WO2012/160358 A1
WO2007/083098 A1
US2016/0106705
US2016/0360721
US2018/0193304

Abid et al. "Exploring patterns enriched in a dataset with contrastive principal component analysis." *Nature Communications* 9.1 (2018): 1-7.

Bates, Douglas; Martin Maechler; Ben Bolker; Steve Walker (2015). Fitting Linear Mixed-Effects Models Using lme4. *Journal of Statistical Software,* 67(1), 1-48. doi:10.18637/jss.v067.i01.

Bouhassira D, 2008 "Prevalence of chronic pain with neuropathic characteristics in the general population." *Pain,* June; 136(3):380-7.

Crippa J A, Crippa A C, Hallak J E, Martin-Santos R, Zuardi A W. 2016. "Δ9-THC intoxication by cannabidiol-enriched *cannabis* extract in two children with refractory epilepsy: full remission after switching to purified cannabidiol." *Front. Pharmacol.* 7:35.

Crippa J A, Guimaraes F S, Campos A C, Zuardi A W. 2018. "Translational Investigation of the Therapeutic Potential of Cannabidiol (CBD): Toward a New Age." *Fron. Immunol. September* 21; 9:02009.

Cudalbu C, McLin V A, Lei H, et al. "The C57BL/6J mouse exhibits sporadic congenital portosystemic shunts." *PLoS One.* 2013; 8(7):e69782. Published 2013 Jul. 23. doi: 10.1371/journal.pone.0069782.

De Petrocellis L, Ligresti A, Moriello A S, Allara M, Bisogno T, Petrosino S, Stott C G, Di Marzo V. 2011. "Effects of cannabinoids and cannabinoid-enriched *Cannabis* extracts on TRP channels and endocannabinoid metabolic enzymes." Br J Pharmacol 163:1479.

Guimaraes F S, Chiaretti T M, Graeff F G, Zuardi A W. 1990. "Antianxiety effect of cannabidiol in the elevated plus-maze". Psychopharmacology (1990) 100:558-9.

Hou S, Huh B, Kim H K, Kim K H, Abdi S. "Treatment of Chemotherapy-Induced Peripheral Neuropathy: Systematic Review and Recommendations". *Pain Physician.* 2018; 21(6):571-592

Izzo A A, Borrelli F, Capasso R, Di Marzo V, Mechoulam R. 2009. "Non-psychotropic plant cannabinoids: new therapeutic opportunities from an ancient herb." *Trends Pharmacol Sci* 30:515.

Izzo, A A, and Aviello G, Borrelli F, Romano B, Piscitelli F, Gallo L, Capasso F, Orlando P, Di Marzo V Capasso R. 2012. "Inhibitory effect of cannabichromene, a major non-psychotropic cannabinoid extracted from *Cannabis sativa*, on inflammation-induced hypermotility in mice." *Br J Pharmacol* 166(4):1444-60.

Kim, S H, and Chung J M. 1992 "An experimental model for peripheral neuropathy produced by segmental spinal nerve ligation in the rat." *Pain.* September; 50(3):355-63.

Lewis M A, Russo E B, and Smith K M. 2017. "Pharmacological foundations of *cannabis* chemovars." *Planta Med.* 84: 225-233.

Maione S, Piscitelli F, Gatta L, D. Vita, L. De Petrocellis, E. Palazzo, V. de Novellis, V. Di Marzo. 2011. "Non-psychoactive cannabinoids modulate the descending pathway of antinociception in anaesthetized rats through several mechanisms of action." *Br. J. Pharmacol.* 162: 584-596.

Mandolini G M, Lazzaretti M, Pigoni A, Oldani L, et al. 2018. "Pharmacological properties of cannabidiol in the treatment of psychiatric disorders: a critical overview." *Epidemiol Psychiatr Sci.* 27(4):327-335.

Morales P, Hurst, D. P., and Reggio, P. H. 2017. "Molecular targets of the phytocannabinoids-a complex picture." *Prog. Chem. Org. Nat. Prod.* 103-131.

Musty, R. E. and Deyo, R. A. (2003) "Cannabichromene (CBC) extract alters Behavioral Despair on the Mouse Tail Suspension test of depression", *Proceedings* 2003 *Symposium on the Cannabinoids*, Burlington, Vt. International Cannabinoid Research Society, p. 146.

Patel, S., Hill, M. N., Cheer, J. F., Wotjak, C. T., and Holmes, A. 2017. "The endocannabinoid system as a target for novel anxiolytic drugs." *Neurosci. Biobehav. Rev.* 76: 56-66.

Reithmeier D, Tang-Wai R, Seifert B, Lyon A W, Alcorn J, Acton B, Corley S, Prosser-Loose E, Mousseau D D, Lim H J, Tellez-Zenteno J, Huh L, Leung E, Carmant L and Huntsman R J. 2018. "The protocol for the Cannabidiol in children with refractory epileptic encephalopathy (CARE-E) study: a phase 1 dosage escalation study." *BMC Pediatrics* 18:221.

Russo, E B. 2011. "Taming THC: potential *cannabis* synergy and phytocannabinoid-terpenoid entourage effects." *Br J Pharmacol* 163:1344.

Shinjyo N, Di Marxo V. 2013. "The effect of cannabichromene on adult neural stem/progenitor cells." *Neurochemistry International* 63(5): 432-437.

Wolf S A, Bick-Sander A, Fabel K, Leal-Galicia P, Tauber S, Ramirez-Rodriguez G, et al. 2010. "Cannabinoid receptor CB1 mediates baseline and activity-induced survival of new neurons in adult hippocampal neurogenesis." *Cell Commun Signal.* 8:12.

What is claimed is:

1. A formulation pairing for use in a method of pain management by a subject in need thereof, said formulation pairing comprising a first formulation and a second formulation for use at different times of a multi-dose daily regimen;

wherein the first formulation comprises cannabichromene (CBC), and cannabidiol (CBD) as primary cannabinoids, and an excipient; wherein the primary cannabinoids in the first formulation comprise or consist of, on a weight % basis: 17%-54% CBC; and 46%-83% CBD; and wherein the second formulation comprises tetrahydrocannabinol (THC), cannabichromene (CBC), and cannabidiol (CBD) as primary cannabinoids, and an excipient; wherein the primary cannabinoids in the second formulation comprise or consist of, on a weight % basis: 30%-45% THC; 9%-35% CBC; and 30%-45% CBD.

2. The formulation pairing of claim 1, wherein the pain management comprises treatment of pain due to cancer, injury, accident, surgery, inflammation, tissue damage, arthritis, joint pain, pain from infection, gastrointestinal pain, diabetes, diabetes neuropathy, post-shingles neuralgia, neuropathic pain, peripheral neuropathy or multiple sclerosis.

3. The formulation pairing of claim 1, wherein:
the primary cannabinoids are present in the first formulation in amounts according to a ratio of CBC:CBD ranging from 1:5 to 5:5, and
the primary cannabinoids are present in the second formulation in amounts according to a ratio of THC:CBC:CBD ranging from 5:5:5 to 5:1:5.

4. The formulation pairing of claim 1, wherein the first and second formulations are prepared in a dosage form selected from the group consisting of a pill, tablet, gel capsule, syrup, oil-based spray, and liquid oil form.

5. The formulation pairing of claim 1, wherein the first and second formulations provide a total amount of from about 1 mg to about 25 mg of primary cannabinoid per dose.

6. The formulation pairing of claim 1, provided as a kit comprising instructions for use in a multi-dose daily regimen.

* * * * *